US009409973B2

(12) United States Patent
Saelens et al.

(10) Patent No.: US 9,409,973 B2
(45) Date of Patent: Aug. 9, 2016

(54) RESPIRATORY SYNCYTIAL VIRUS VACCINE

(75) Inventors: Xavier Saelens, Ypres (BE); Bert Schepens, Ghent (BE); Walter Fiers, Destelbergen (BE)

(73) Assignees: VIB VZW, Ghent (BE); Universiteit Gent, Ghent (BE)

(*) Notice: Subject to any disclaimer, the term of this patent is extended or adjusted under 35 U.S.C. 154(b) by 186 days.

(21) Appl. No.: 13/885,388

(22) PCT Filed: Nov. 15, 2011

(86) PCT No.: PCT/EP2011/070161
§ 371 (c)(1),
(2), (4) Date: Aug. 7, 2013

(87) PCT Pub. No.: WO2012/065997
PCT Pub. Date: May 24, 2012

(65) Prior Publication Data
US 2013/0315916 A1 Nov. 28, 2013

Related U.S. Application Data

(60) Provisional application No. 61/458,012, filed on Nov. 15, 2010.

(30) Foreign Application Priority Data

Nov. 15, 2010 (GB) .................................. 1019240.9

(51) Int. Cl.
*A61K 39/155* (2006.01)
*C07K 16/10* (2006.01)
*A61K 39/12* (2006.01)
*C12N 7/02* (2006.01)
*C07K 7/06* (2006.01)
*C07K 14/005* (2006.01)
*C07K 14/78* (2006.01)
*A61K 39/385* (2006.01)
*A61K 39/00* (2006.01)

(52) U.S. Cl.
CPC ............ *C07K 16/1027* (2013.01); *A61K 39/12* (2013.01); *A61K 39/385* (2013.01); *C07K 7/06* (2013.01); *C07K 14/005* (2013.01); *C07K 14/78* (2013.01); *C12N 7/02* (2013.01); *A61K 2039/5258* (2013.01); *A61K 2039/543* (2013.01); *A61K 2039/55505* (2013.01); *A61K 2039/55544* (2013.01); *A61K 2039/55566* (2013.01); *A61K 2039/6075* (2013.01); *A61K 2039/6081* (2013.01); *C07K 2317/76* (2013.01); *C12N 2760/18534* (2013.01)

(58) Field of Classification Search
None
See application file for complete search history.

(56) References Cited

U.S. PATENT DOCUMENTS

| | | |
|---|---|---|
| 7,510,863 B2 * | 3/2009 | Samal et al. ............... 435/235.1 |
| 2007/0184069 A1 | 8/2007 | Buchholz et al. |
| 2009/0285853 A1 | 11/2009 | Cheng et al. |

FOREIGN PATENT DOCUMENTS

| | | |
|---|---|---|
| WO | 2008/106980 A2 | 9/2008 |
| WO | 2008/133663 A2 | 11/2008 |
| WO | 2009/092113 A2 | 7/2009 |
| WO | WO 2012-065997 A1 | 5/2012 |

OTHER PUBLICATIONS

Collins et al., J Gen Virol 1993 vol. 74, pp. 1445-1450.*
Pringle C R et al: Immunogenicity and Pathogenicity of a Triple Temperature-Sensitive Modified Respiratory Syncytial Virus in Adult Volunteers, Vaccine. Elsevier Ltd. GB, vol. 11, No. 4. Mar. 1, 1993, pp. 473-478.
Power U F et al: Induction of Protective Immunity in Rodents by Vaccination with a Prokaryotically Expressed Recombinant Fusion Protein Containing a Respiratory Syncytial Virus G Protein Fragment, Virology. Academic Press. Orlando. US, vol. 230, No. 2. Apr. 14, 1997, pp. 155-166.
Bastien N et al: Complete protection of mice from respiratory syncytial virus infection following mucosal delivery of synthetic peptide vaccines, Vaccine. Elsevier Ltd. GB, vol. 17, No. 7-8. Feb. 26, 1999, pp. 832-836.
Singh et al: Immunogenicity and efficacy of recombinant RSV-F vaccine in a mouse model, Vaccine. Elsevier Ltd. GB, vol. 25. No. 33. Jul. 24, 2007, pp. 6211-6223.
Edward E. Walsh: Respiratory Syncytial Virus Vaccine, Encyclopedia of Molecular Cell Biology and Molecular Medicine. 2nd Edition, vol. 12, 2005, pp. 297-322.
Woo W-P et al: Hepatitis B Surface Antigen Vector Delivers Protective Cytotoxic T-Lymphocyte Responses to Disease-Relevant Foreign Epitopes, Journal of Virology. The American Society for Microbiology. US, vol. 80, No. 8. Apr. 1, 2006, pp. 3975-3984.
Schmidt A C et al: Mucosal immunization of Rhesus monkeys against respiratory syncytial virus subgroups A and B and human parainfluenza virus type 3 by using a live eDNA-derived vaccine based on a host range-attenuated bovine parainfluenza virus type 3 vector backbone, Journal of Virology. The American Society for Microbiology. US, vol. 76, No. 3. Feb. 1, 2002, pp. 1089-1099.
Yoshihiko Murata: Respiratory Syncytial Virus Vaccine Development, Clinics in Laboratory Medicine, vol. 29, No. 4, Dec. 1, 2009, pp. 725-739.

(Continued)

*Primary Examiner* — Shanon A Foley
*Assistant Examiner* — Myron Hill
(74) *Attorney, Agent, or Firm* — Lathrop & Gage LLP; James H. Velema

(57) ABSTRACT

Described is a vaccine against Respiratory Syncytial Virus (RSV). More specifically, described is a recombinant subunit vaccine comprising the ectodomain of the RSV-encoded Small Hydrophobic (SH) protein. The ectodomain of SH is referred to as SHe. The ectodomain is typically presented as an oligomer, or a pentamer. Further described are antibodies, raised against the ectodomain or specific for the ectodomain, and their use for protecting a subject against RSV infection and/or for treatment of an infected subject.

12 Claims, 31 Drawing Sheets

(56) References Cited

OTHER PUBLICATIONS

Figure 2:
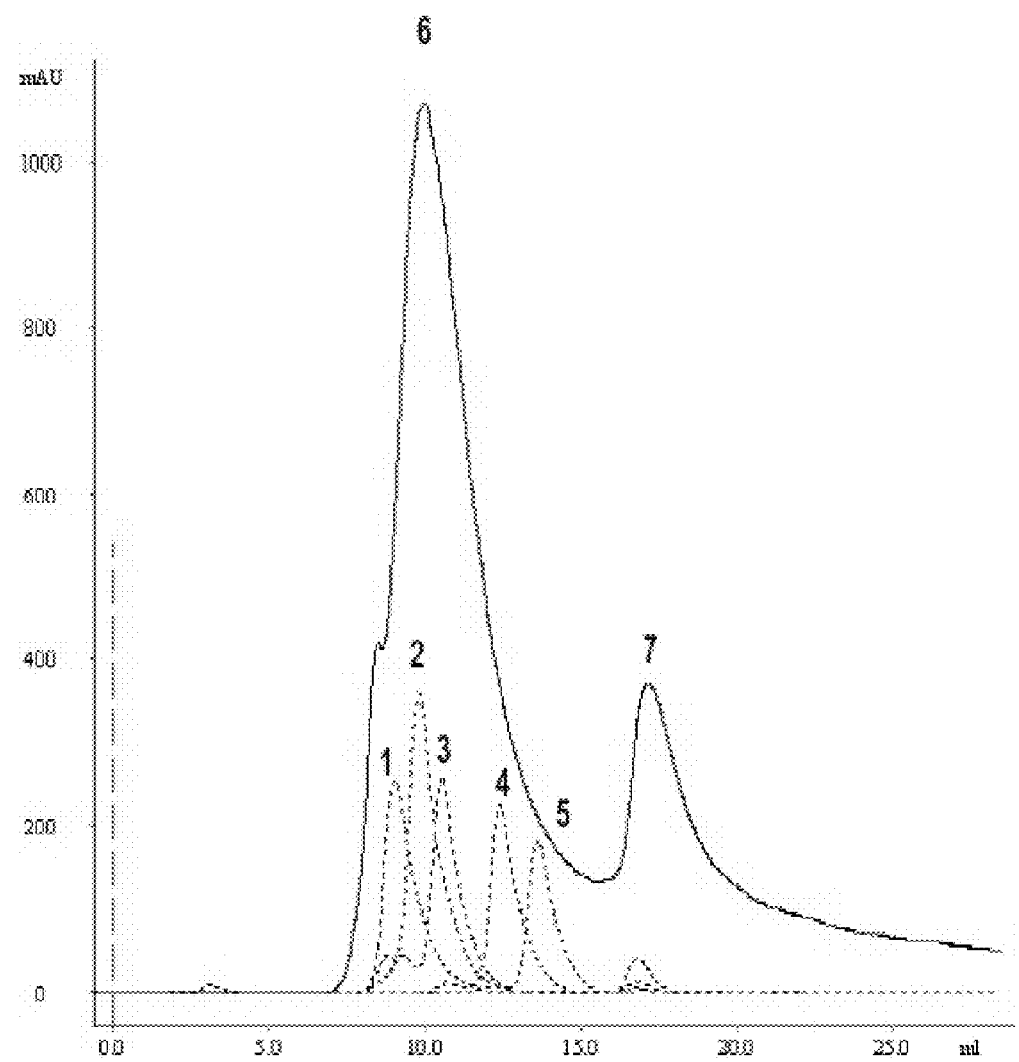
Figure 2:
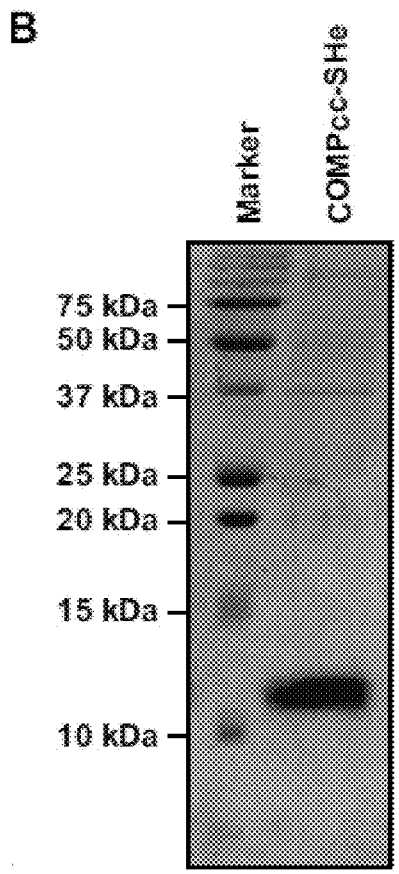
Figure 2:
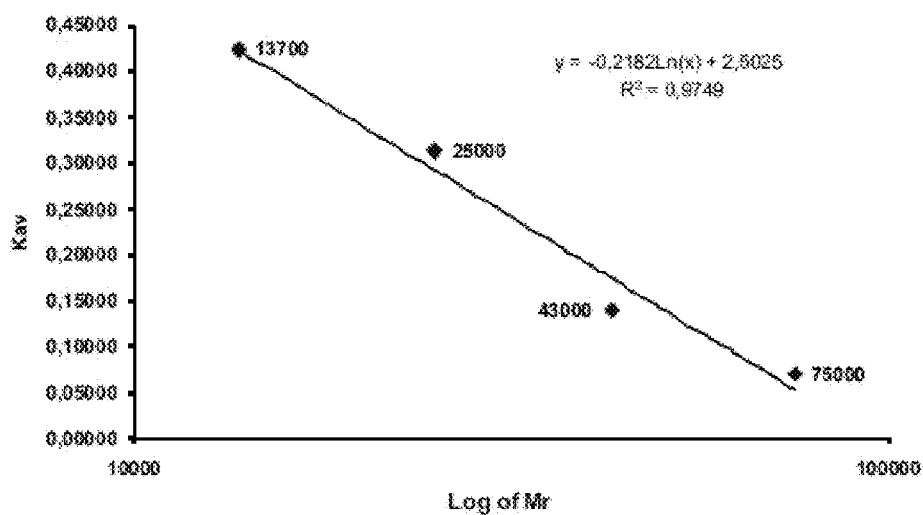
Figure 3:
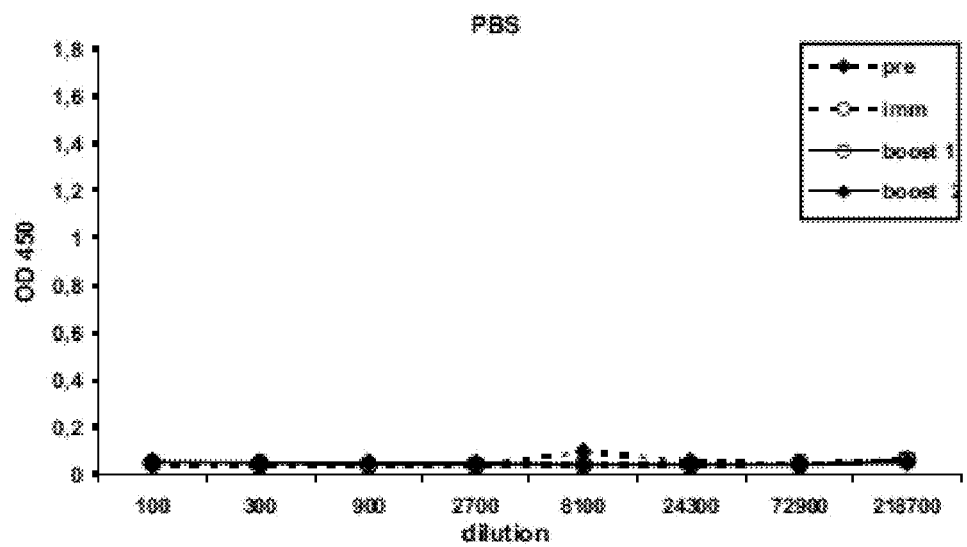
Figure 3:
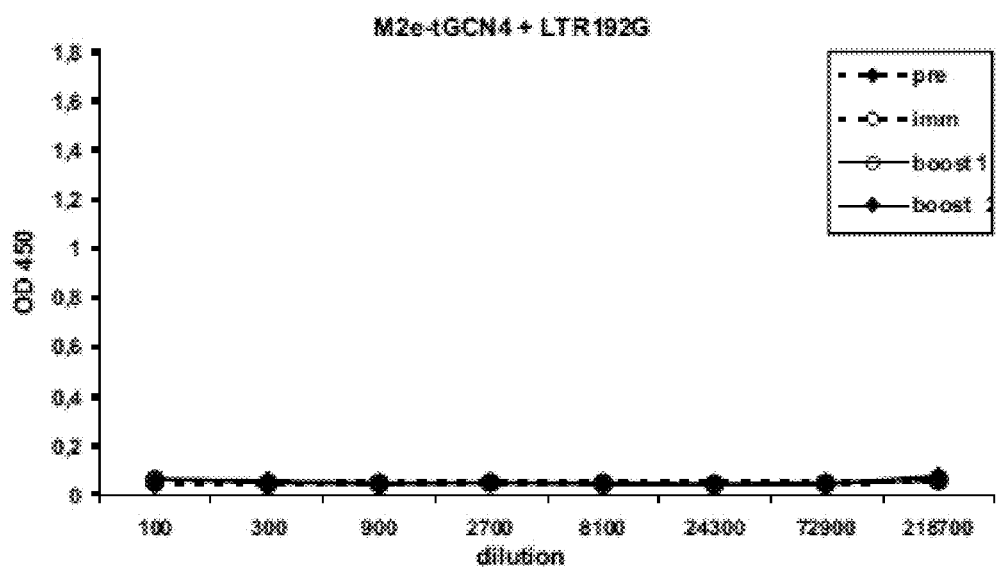
Figure 3:
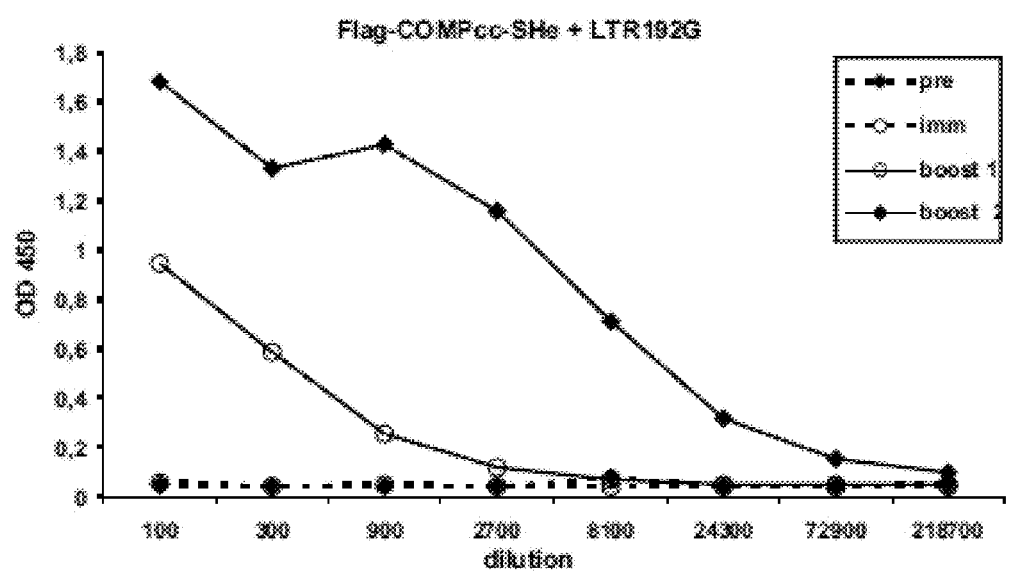
Figure 3:
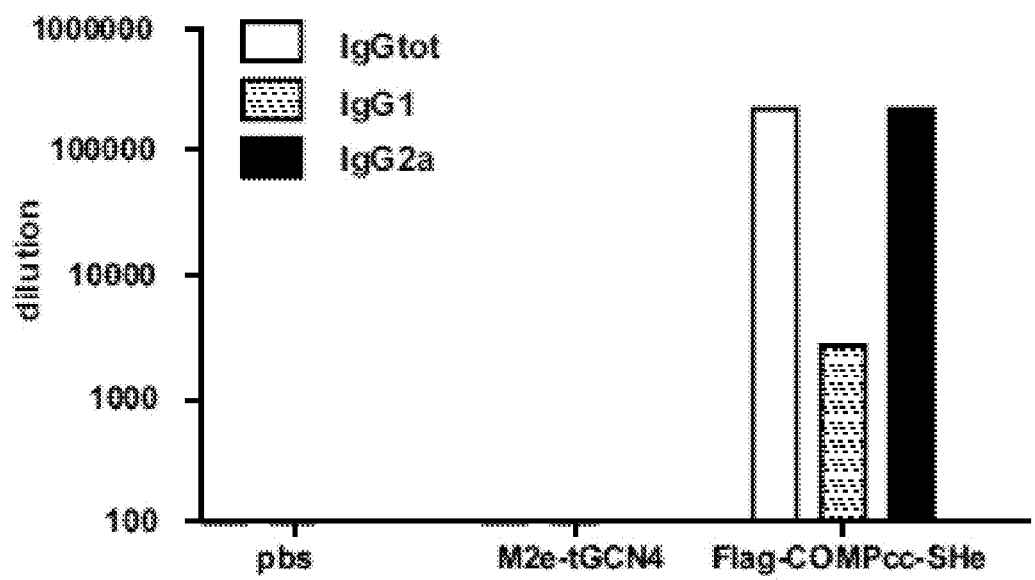

Initiative for Vaccine Research (IVR), Acute Respiratory infections (Update Sep. 2009) available at http://www.who.int/vaccine_research/diseases/ari/en/index2.html, printed May 14, 2013.

PCT International Search Report, PCT/EP2011/070161, dated Mar. 9, 2012.

Fuentes et al. (2007) "Function of the Respiratory Syncytial Virus Small Hydrophobic Protein," Journal of Virology. 81(15):8361-8366.

Office Action corresponding to Japanese Patent Application No. 2013-538235, mailed Sep. 29, 2015—with English translation.

Gan et al. (2008) "Structure and Ion Channel Activity of the Human Respiratory Syncytial Virus (hRSV) Small Hydrophobic Protein Transmembrane Domain," Protein Science. 17:813-820.

Olmsted et al. (1989) "The 1A protein of respiratory syncytial virus is an integral membrane protein present as multiple, structurally distinct species," J. Virol. 63(5):2019-2029.

Rixon et al. (2004) "The small hydrophobic (SH) protein accumulates within lipid-raft structures of the Golgi complex luring respiratory syncytial virus infection," J. Gen. Virol. 85:1153-1165.

Rixon et al. (2005) "The respiratory syncytial virus small hydrophobic protein is phosphorylated via a mitogen-activated protein kinase p38-dependent tyrosine kinase activity during virus infection," J. Gen. Virol. 86:375-384.

Examination Report corresponding to Australian Patent Application No. 2011331251, issued Apr. 15, 2016.

\* cited by examiner

A

HRSV A SH ectodomain : NKLCEYNVFHNKTFELPRARVNT (SEQ ID NO:1)

HRSV B SH ectodomain : NKLSEHKTFCNNTLELGQMHQINT (SEQ ID NO:2)

BRSV SH ectodomain: NKLCDFNDHHTNSLDIRTRLRNDTQLITRAHEGSINQSSN (SEQ ID NO:17)

B

MDYKDDDDK *DLAPQMLRELQETNAALQDVRELLRHQVKEITFLKNTVMECDACG* NKLCEYNVFHNKTFELPRARVNT (SEQ ID NO:35)

C

D

FIG. 1

B

| peak | protein | Mr (kDa) | Ve (ml) | Kav = (Ve-V0)/Vtot-V0 |
|---|---|---|---|---|
| Peak 1 | Aldolase | 158 | 9.05 | 0.000 |
| Peak 2 | Conalbumin | 75 | 9.85 | 0.070 |
| Peak 3 | Albumin | 43 | 10.5 | 0.138 |
| Peak 4 | Chymatrypsinagen | 25 | 2.4 | 0.312 |
| Peak 5 | Ribonuclease A | 13.7 | 13.6 | 0.423 |
| Peak 6 | Flag-COMPcc-SHe | 63.0 | 10.3 | 0.091 |

C

RESPIRATORY SYNCYTIAL VIRUS VACCINE

CROSS-REFERENCE TO RELATED APPLICATIONS

This application is a national phase entry under 35 U.S.C. §371 of International Patent Application PCT/EP2011/070161, filed Nov. 15, 2011, designating the United States of America and published in English as International Patent Publication WO 2012/065997 A1 on May 24, 2012, which claims the benefit under Article 8 of the Patent Cooperation Treaty to Great Britain Patent Application Serial No. 1019240.9, filed Nov. 15, 2010, and under Article 8 of the Patent Cooperation Treaty and under 35 U.S.C. §119(e) to U.S. Provisional Patent Application Ser. No. 61/458,012, filed Nov. 15, 2010.

TECHNICAL FIELD

The disclosure relates generally to biotechnology and medicine and more particularly to a vaccine against Respiratory Syncytial Virus (RSV). More specifically, it relates to a recombinant subunit vaccine comprising the ectodomain of the RSV-encoded Small Hydrophobic (SH) protein. The ectodomain of SH is referred to as SHe. The ectodomain may be presented as an oligomer, even more preferably, as a pentamer. The disclosure relates further to antibodies, raised against the ectodomain or specific for the ectodomain, and their use for protecting a subject against RSV infection and/or for treatment of an infected subject.

BACKGROUND

RSV infection is the leading cause of infant hospitalization in industrialized countries. Following primary RSV infection, which generally occurs under the age of 2 years, immunity to RSV remains incomplete, and reinfection can occur. Furthermore, RSV can cause serious disease in the elderly and is, in general, associated with higher mortality than influenza A in non-pandemic years (Falsey et al., 1995). The WHO-estimated global annual infection rate in the human population is estimated at 64 million cases, with a mortality figure of 160000; in the US alone, from 85000 to 144000 infants are hospitalized each year as a consequence of RSV infection (on the World Wide Web at who.int/vaccine_research/diseases/ari/en/index2.html update 2009).

RSV belongs to the family Paramyxoviridae, subfamily Pneumovirinae, genus *Pneumovirus*; in human, there are two subgroups, A and B. Apart from the human RSV, there is a bovine variant. The genome of human RSV is approximately 15200 nucleotides long and is a negative-sense RNA molecule. The RSV genome encodes 11 known proteins: Glycoprotein (G), Fusion protein (F), Small hydrophobic protein (SH), Nucleoprotein (N), Phosphoprotein (P), Large protein (L), Matrix protein (M), M2 ORF-1 protein (M2-1), M2 ORF-2 protein (M2-2), Nonstructural protein 1 (NS1) and Nonstructural protein 2 (NS2). G, F and SH are transmembrane surface proteins; N, P, L, M, M2-1 are nucleocapsid associated proteins; and NS1 and NS2 are non-structural proteins. The status of M2-2 as a structural or nonstructural protein is unknown. (Hacking and Hull, 2002.) The RSV subgroups show differences in the antigenic properties of the G, F, N and P proteins (Ogra, 2004).

RSV infection is followed by the formation of specific IgG and IgA antibodies detectable in the serum and some other body fluids. Several studies have demonstrated that antibody responses are mainly directed to the major RSV transmembrane proteins F and G; only F- and G-specific antibodies are known to have in vitro RSV-neutralizing activity. Antibody responses to the F protein are often cross-reactive between the A and B subgroups, whereas antibody responses to the G protein are subgroup specific (Orga, 2004). Contrary to F and G, the transmembrane protein SH is considered as non-immunogenic (Gimenez et al., 1987; Tsutsumi et al., 1989) and in some vaccine candidates, SH has even been deleted in order to obtain a non-revertible attenuated vaccine (Karron et al., 2005).

Development of vaccines to prevent RSV infection has been complicated by the fact that host immune responses appear to play a significant role in the pathogenesis of the disease. Early attempts at vaccinating children with formalin-inactivated RSV showed that vaccinated children experienced a more severe disease on subsequent exposure to the virus as compared to the unvaccinated controls (Kapikian et al., 1969). Live attenuated vaccines have been tested, but show often over- or underattenuation in clinical studies (Murata, 2009).

Subunit vaccines using one immunogenic protein or a combination of immunogenic proteins are considered safer, because they are unable to revert or mutate to a virulent virus. Candidate vaccines based on purified F protein have been developed and were tested in rodents, cotton rats, and humans, and were shown to be safe, but only moderately immunogenic (Falsey and Walsh, 1996; Falsey and Walsh, 1997; Groothuis et al., 1998). In a similar vein, clinical trials with a mixture of F-, G- and M-proteins have been discontinued in phase II (ADISinsight Clinical database). An alternative approach consisted of a recombinant genetic fusion of the antigenic domain of human RSV G protein to the C-terminal end of the albumin-binding domain of the streptococcal G protein (BBG2Na; Power et al., 2001). BBG2Na was investigated up to a phase III clinical trial in healthy volunteers, but the trial had to be stopped due to the appearance of unexpected type 3 hypersensitivity side effects (purpura) in some immunized volunteers (Meyer et al., 2008).

A recent development is the use of chimeric recombinant viruses as vector for RSV antigens. A chimeric recombinant bovine/human parainfluenzavirus type 3 (rB/HPIV-3) was engineered by substituting in a BPIV-3 genome the F and HN genes by the homologous genes from HPIBV-3. The resulting chimeric rB/HPIV-3 strain was then used to express the HRSV F and G genes (Schmidt et al., 2002). This vaccine is currently under clinical investigation.

Only a limited number of prevention and treatment options are available for the severe disease caused by RSV. The most widely used intervention is based on passive immunoprophylaxis with a humanized monoclonal antibody that is derived from mouse monoclonal antibody 1129 (Beeler and van Wyke Coelingh, 1989). This antibody is specific for RSV F protein and neutralizes subgroup A and B viruses. The recombinant humanized antibody 1129 is known as palivizumab (also known as Synagis) and is used for prophylactic therapy of infants that are at high risk of developing complications upon RSV infection. The antibody is administered intramuscularly on a monthly basis in order to lower the risk of RSV infection in infants at risk due to prematurity, chronic lung disease, or hemodynamically significant congenital heart disease (Bocchini et al., 2009). Some studies have reported acceptable cost-effectiveness ratios for RSV prophylaxis with palivizumab (Prescott et al., 2010).

SUMMARY OF THE DISCLOSURE

As there is no approved vaccine on the market, there is still an unmet need for development and availability of a safe and efficient RSV vaccine. Surprisingly, we found that the extracellular part (ectodomain) of the small hydrophobic protein SH, referred to as SHe, can be used safely for vaccination against RSV infection, especially when it is presented on a carrier as an oligomer, such as a pentamer. Furthermore, polyclonal or monoclonal antibodies, directed against SHe, can also be used prophylactically or therapeutically for prevention or treatment of RSV infection, respectively.

Described is an immunogenic composition comprising the ectodomain of the small hydrophobic (SH) protein of a Respiratory Syncytial Virus (RSV), and a carrier. In one embodiment, RSV is either a human subgroup A or a human subgroup B strain; in another embodiment, RSV is bovine RSV. The SH protein is known to the person skilled in the art, and contains 64 (RSV subgroup A), 65 (RSV subgroup B) amino acid residues or 81, 77 or 72 amino acid residues for bovine RSV. In one embodiment, the ectodomain of SH(SHe) consists of the 23 carboxy terminal amino acids for subgroup A (SEQ ID NO:1), and of the 24 carboxy terminal amino acids for subgroup B (SEQ ID NO:2). The sequence of the ectodomain may be selected from the group consisting of SEQ ID N° 1 (ectodomain subgroup A) and SEQ ID N° 2 (ectodomain subgroup B), or a variant thereof. A "variant," as used herein, means that the sequence can carry one or more mutations, such as deletions, insertions or substitutions. In certain embodiments, the mutations are substitutions. Even more preferably, the variant has 80% identities, preferably 85% identities, even more preferably, 90% identities, most preferably 95% identities, as measured in a BLASTp alignment (Altschul et al., 1997). Preferably, the variant comprises the sequence NKL C/S E Y/H K/N XF (SEQ ID NO:3). Preferred variants are listed in SEQ ID NO:4-SEQ ID NO:16. In another preferred embodiment, the ectodomain consists of SEQ ID NO:17 (ectodomain of Bovine RSV SH) or a variant thereof, as defined above. Preferably, the variant comprises the sequence NKLCXXXXXHTNSL (SEQ ID NO:18). Preferred variants are listed in SEQ ID NOS:19-30.

A carrier molecule is a molecule that is heterologous to the SH protein; a carrier can be any carrier known to the person skilled in the art as suitable for the presentation of an antigen and includes, but is not limited to, virus-like particles such as HBcore (Whitacre et al., 2009), and other VLPs derived from assembling virus capsid or coat proteins. Any other molecular construct can also be used, provided it can efficiently present antigens to the immune system, such as the pentameric Cartilage Oligomeric Matrix Protein (comp; McFarlane et al., 2009), Thromobospondins 3 and 4 (Malashkevich et al., 1996), the B subunit of bacterial AB5 type toxins (e.g., subunit of Cholera toxin or *E. coli* heat labile toxin; Williams et al., 2006), a pentameric tryptophan-zipper (Liu et al., 2004), a pentameric phenylalanine-zipper (Liu et al., 2006) or a tetrameric GCN4-derived leuzine zipper (tGCN4, De Filette et al., 2008) and Lpp-56 (Shu et al., 2000). The carrier can be of a proteinaceous nature, as well as of a non-proteinaceous nature. Examples of non-proteinaceous nature carriers are, as a non-limiting example, liposomes, CLIPS™ constructs (Timmerman et al., 2007) and trimethyl chitosan (Sliitter et al., 2010). Preferably, the carrier presents the SHe as an oligomer, even more preferably, as a pentamer, by presenting multiple SHe molecules on one scaffold, by presenting one SHe on a multimerizing scaffold, or by a combination of both. The SHe oligomer may be presented as a linear repeated structure, or as individual SHe units forming an oligomeric complex, or as a combination of both. The carrier may be an oligomeric carrier (dimeric, up to decameric) or a pentameric carrier. In one specific embodiment, the transmembrane domain of SH, which may be without the cytoplasmic domain, can be used as oligomerizing domain, optionally further fused or linked to a carrier.

Not all carrier molecules should be loaded by SHe. Indeed, as a non-limiting example, one can imagine that only 5 units of a hexameric carrier are loaded with SHe, thereby presenting a pentameric SHe complex on a hexameric carrier complex. The ectodomain can be genetically linked to the carrier, aiming a fusion protein; both domains may be directly fused, or they may be linked by a hinge sequence or a spacer sequence. As used here, in a genetically fused construct, a hinge sequence is an amino acid sequence that links two domains together; the sequence links the two domains in a flexible way; the hinge sequence is shorter than 150 amino acids, even more preferably, shorter than 100 amino acids, even more preferably, shorter than 50 amino acids, most preferably, shorter than 20 amino acids. A "spacer," as used herein, indicates a short hinge sequence shorter than 15 amino acids. In one embodiment, a hinge sequence comprises the sequence $(Gly-Ser)_n$ with n equal to one, 2, 3, . . . 20. In another embodiment, the hinge of immunoglobulin genes, such as the hinge region of human IgG1, is used as a hinge sequence. In the case of a genetic linkage, the linkage may occur at the amino terminal end of the SHe, as well as at the carboxy terminal end.

Alternatively, the ectodomain is chemically linked to the carrier. Chemical linkage is known to the person skilled in the art, and includes, but is not limited to, peptides that are conjugated to the carrier by covalently joining peptides to reactive sites on the surface of the carrier. The resulting structure is a conjugate. A reactive site on the surface of the carrier is a site that is chemically active or that can be activated and is sterically accessible for covalent joining with a peptide. A preferred reactive site is the epsilon nitrogen of the amino acid lysine. Covalently joined refers to the presence of a covalent linkage that is stable to hydrolysis under physiological conditions. The covalent linkage may be stable to other reactions that may occur under physiological conditions including adduct formation, oxidation, and reduction. Often, the linkage of an antigenic peptide to a carrier is achieved using bifunctional reagents (Hermanson, 1996). Any suitable residue in the SHe may be used for linkage to the chemical carrier; preferably, SHe is linked to the carrier by its amino terminal or carboxy terminal end.

In still another embodiment, the ectodomain is linked to the carrier by a non-covalent interaction, such as, but not limited to, hydrophobic interactions, cooperative H-bond interactions, or Van der Waals interactions.

Also described is the use of an immunogenic composition hereof as a vaccine. Still further described is the use of an immunogenic composition hereof for the preparation of a vaccine for the protection against RSV infection. The RSV may be selected from the group consisting of RSV subgroup A and RSV subgroup B. The vaccine can be administrated to the subject to be treated by any route known to the person skilled in the art including, but not limited to, intranasal, intraperitoneal, intramuscular and intradermal administration. Preferably, there is no enhancement of the disease symptoms upon RSV infection after vaccination. The vaccine can be for animal or for human use. A preferred animal use is for protection of cattle or other Bovidae by vaccination against bovine respiratory viruses related to human RSV, such as, but not limited to, Bovine RSV. Protection against RSV infection covers both prophylactic and therapeutic uses. More particularly, a preferred use of the vaccine is for prophylactic purposes. "Preparation of a vaccine," as used herein, means that the immunogenic composition hereof may be optimized by addition of suitable excipients, or it may be formulated for, as a non-limiting example, increasing the shelf life or improving the pharmaceutical characteristics of the vaccine.

Described is a vaccine comprising an immunogenic composition hereof, or a combination of immunogenic compositions hereof. Indeed, as a non-limiting example, immunogenic compositions comprising SHe of RSV subgroup A and SHe of RSV subgroup B may be mixed to obtain a vaccine with a broader specificity. The vaccine can be for human or for veterinary use. Apart from the immunogenic composition, the vaccine may comprise one or more other compounds, such as an adjuvant. The vaccine may be a vaccine for the protection of humans against RSV infection or, in animals, against animal respiratory viruses related to human RSV, such as, but not limited to, bovine RSV.

Described is the use of an immunogenic composition hereof for the detection and/or purification of antibodies, directed against the ectodomain of RSV. Such antibodies may be isolated after vaccinating a subject with the immunogenic composition of the invention; alternatively, similar antibodies and/or antibody-producing cells can also be obtained from an RSV-infected human or animal subject, and, after proper development known in the art, used for production of SHe-specific antibodies, preferably human-type antibodies that can be used for prophylactic or therapeutic purposes as described above.

Described is a method for the production of blood, plasma and/or serum from an animal, the blood, plasma and/or serum comprising one or more antibodies or cells producing antibodies against the SHe domain of RSV, the method comprising (a) delivering an immunogenic composition hereof to the animal and (b) obtaining blood, plasma and/or serum from the animal, wherein the blood, plasma and/or serum comprises one or more antibodies or cells producing antibodies against the SHe domain of RSV, or cells producing the antibodies. Preferably, the animal is a non-human animal. As used herein, "plasma" is the liquid fraction of the blood after removal of the blood cells; serum is plasma after removal of fibrinogen and other blood clotting factors. As indicated above, specific anti-SHe antibodies may be isolated using the immunogenic composition hereof.

Described is the use of blood, plasma and/or serum containing RSV-antibodies and obtained with the method hereof for protection against RSV infection and/or treatment of RSV infection. As mentioned above, protection against RSV infection covers both the prophylactic and therapeutic use. Indeed, the antibody-comprising serum can be administered to a human or an animal, thereby providing passive immunity against the RSV infection. The serum may be part of a pharmaceutical composition comprising the serum, wherein the serum is formulated and/or mixed with a suitable excipient. Described is a pharmaceutical composition comprising a serum obtained with the method hereof.

Described is an RSV-inhibiting monoclonal antibody, directed against the ectodomain of the RSV SH-protein. "RSV-inhibiting," as used herein, means that, upon infection, the lung virus titer is lower in treated animals compared to the non-treated animals, as measured in a suitable animal model. Preferably, the monoclonal antibody is a human or humanized monoclonal antibody.

Described is a pharmaceutical composition comprising a monoclonal antibody directed against the ectodomain of the RSV SH-protein, hereof. Indeed, an organ of an immunized non-human animal, preferably the spleen of the animal, or a blood sample from an immunized animal or human subject, can be used as starting material for the production of monoclonal antibodies and derivatives such as, but not limited to, single-chain antibodies, multivalent antibodies, or antibodies linked to antiviral compounds. The monoclonal antibodies and derivatives are used for passive immunization or for treatment of RSV infection.

BRIEF DESCRIPTION OF THE DRAWINGS

FIG. 1: Panel A, The amino acid sequences of the subtype A human RSV (hRSV) SH ectodomain (SEQ ID NO:1), of the subtype B human RSV SH ectodomain (SEQ ID NO:2), and of the bovine RSV (bRSV) SH ectodomain (SEQ ID NO:17). Panel B, The amino acid sequence of Flag-COMPcc-SHe (SEQ ID NO:35). The first nine amino acids represent the N-terminal Flag-tag. The amino acids (AA) in italic font represent the coiled coil domain of rat COMP (AA 25-72). The underlined AA represent the ectodomain of the RSV A small hydrophobic protein (SHe). Panel C, Schematic representation of Flag-COMPcc-SHe pentameric protein. Panel D, Schematic representation of COMPcc-SHe pentameric protein.

FIG. 2: Purification and determination of the relative molecular mass of Flag-COMPcc-SHe. Panel A, Elution curves of aldolase (1), conalbumin (2), albumin (3), chymotrypsinogen (4), ribonuclease A (5) and Flag-COMPcc-SHe (6 en 7) upon gel filtration on a Superdex 75 column. Panel B, Coomassie blue staining of a SDS-PAGE analysis of Flag-COMPcc-SHe after gel filtration (peak 6 of panel A). Panel C, overview of the proteins used to calibrate the gel filtration column, their relative molecular weight (Mr), the Volume at which they eluted from the column (Ve) and the calculated Kay (Kay=(Ve−V0)/(Vtot−V0), with V0=the column void volume=9.05 and Vtot=the column bed volume=19.816). The Mr of Flag-COMPcc-SHe present in peak 6 was calculated based on its Ve and the calibration curve presented in panel D. Panel D, The calibration curve of the Superdex 75 gel filtration column used to purify pentameric Flag-COMPcc-SHe.

FIG. 3: Vaccination of Balb/c mice with Flag-COMPcc-SHe in combination with LTR192G induces SHe-specific antibodies. Panels A, B and C, ELISA-based determination of the SHe peptide-specific IgG antibodies titers present in the pooled sera of mice after the first, second or third immunization with the indicated vaccines. Panel D, SHe peptide-specific IgG, IgG1 and IgG2a antibodies present in the pooled sera of mice that were vaccinated with PBS, M2e-tGCN4/LTR192G or Flag-COMPcc-SHe/LTR192G.

FIG. 4: Flag-COMPcc-SHe vaccination, as in legend of FIG. 3, induces antibodies that can recognize the SH-ectodomain on the surface of cells. Panel A, Flow cytometric analysis of GFP and RSV SH-expressing HEK293T cells stained by different dilutions of serum of Flag-COMPcc-SHe vaccinated mice. Panel B, Flow cytometric analysis of GFP and RSV SH-expressing HEK cells stained by serum from Flag-COMPcc-SHe or M2e-tGCN4 (negative control) vaccinated mice. Panel C, Flow cytometric analysis of GFP and Luciferase-expressing HEK cells stained by serum from Flag-COMPcc-SHe or M2e-tGCN4 vaccinated mice.

FIG. 5: Flag-COMPcc-SHe vaccination inhibits RSV replication. Four days after challenge, mice of the indicated groups were sacrificed to determine viral lung titer by plaque assay. The graph shows the number of plaque-forming units per lung of each mouse. The detection limit of the plaque assay is 10 PFU per lung. The difference in RSV lung titer between the Flag-COMPcc-SHe-vaccinated and the M2e-tGCN4-vaccinated mice was highly significant (*** $p \leq 0.0005$).

FIG. 6: Flag-COMPcc-SHe vaccination does not induce enhanced disease upon RSV infection. The graph shows the relative body weight of each mouse, calculated as the ratio between the weight at the day of sacrifice (four days after infection) and the weight at the day of viral infection, multiplied by 100.

Figure 7:
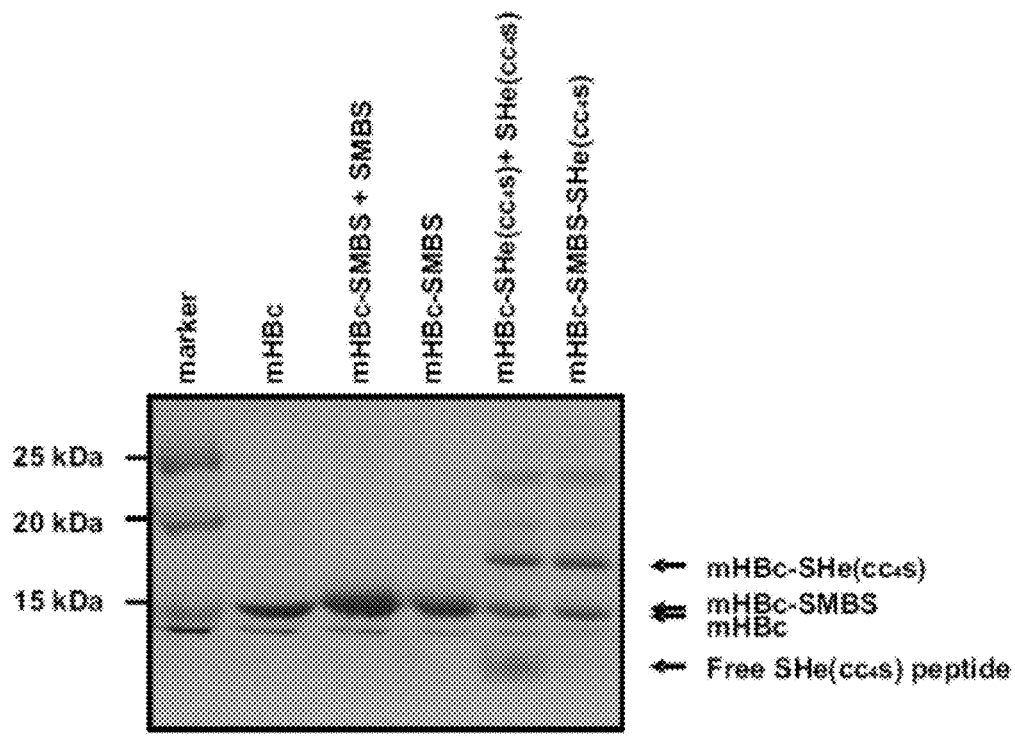

FIG. 7: Chemical linkage of SHe(cc4s) peptides to the immunodominant loops of mHBc virus-like particles. Coomassie blue stained SDS-PAGE analysis of mHBc at the different stages of chemical linkage as indicated above the gel: mHBc=purified mHBc, mHBc-SMBS+sMBS=mHBc after addition of the chemical linker Sulfo-MBS, mHBc-SMBS=mHBc-SMBS after size exclusion chromatography, mHBC-SHe(cc$_4$s)+SHe(cc$_4$s)=purified mHBc-SMBS after incubation with SHe(cc$_4$s) peptide, mHBC-SHe(cc$_4$s)=SHe linked to mHBc VLPs after purification by size exclusion chromatography.

Figure 8:
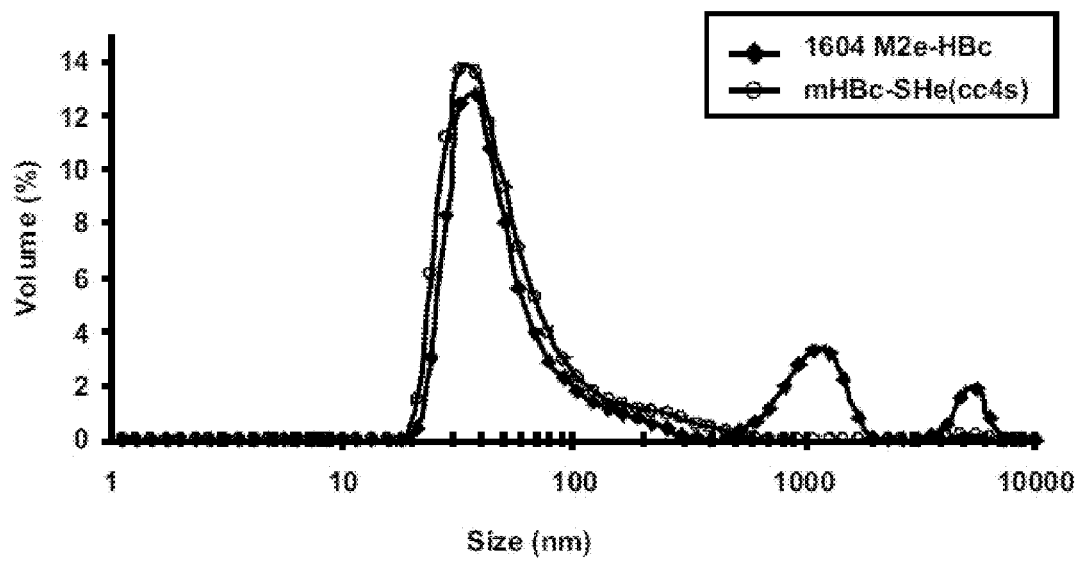

FIG. 8: mHBc-SHe(cc4s) retains its VLP conformation. The graph represents the size distribution of mHBc-SHe (cc4s) and the well-described M2e-mBHc VLP 1604 as determined by dynamic light scattering. The size distribution is expressed in function of the Volume.

Figure 9:
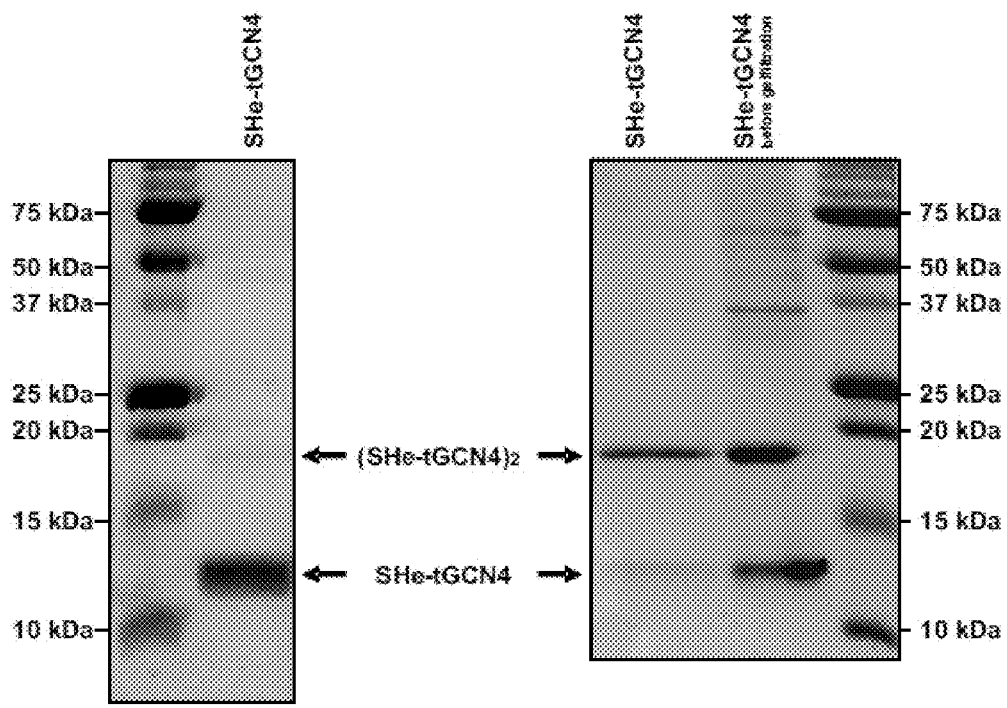

FIG. 9: Purification of SHe-tGCN4. SDS-PAGE analysis followed by Coomassie blue staining of SHe-tGCN4 after purification by a series of column chromatographic steps: anion exchange, hydrophobic interaction and gel filtration chromatography. The left and right panels represent SDS-PAGE analysis under reducing (in the presence of beta-mercaptoethanol) or non-reducing (in the absence of beta-mercaptoethanol), respectively. The arrows indicate monomeric and dimeric SHe-tGCN4 proteins.

Figure 10:
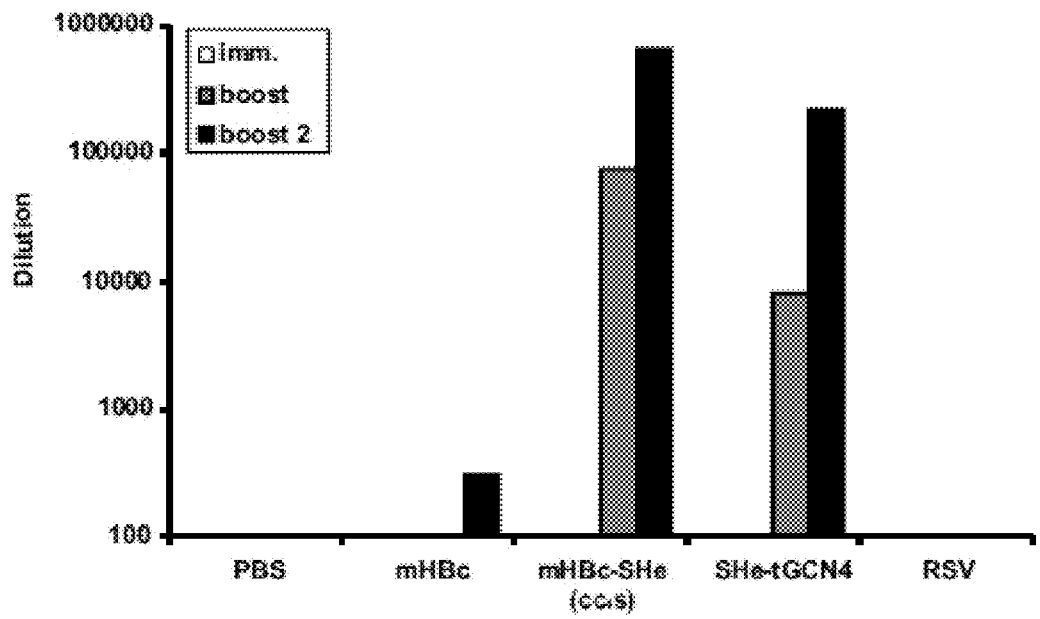
Figure 10:
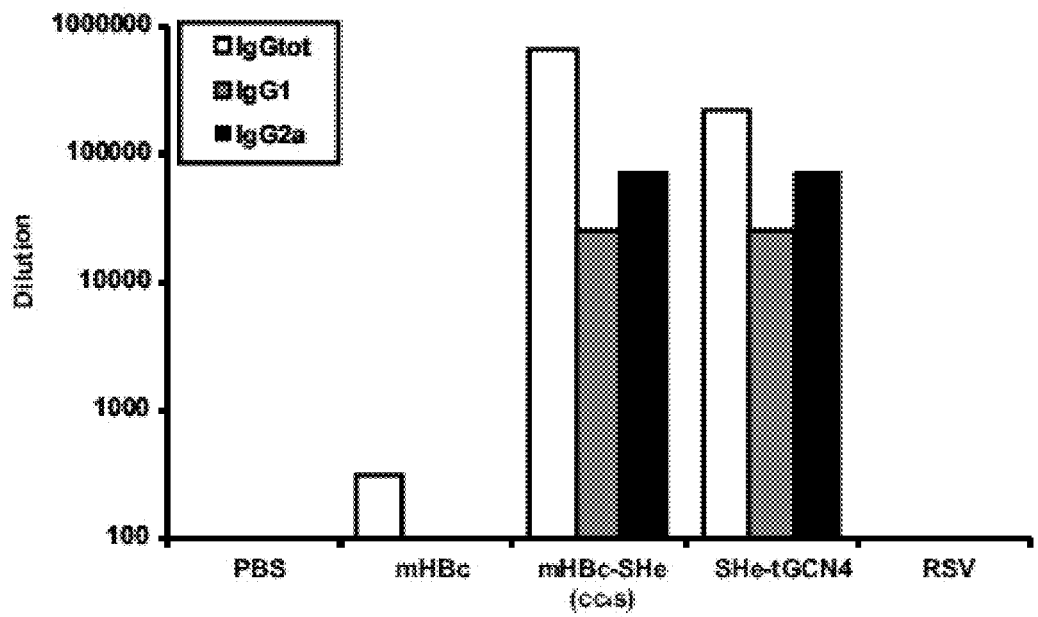

FIG. 10: Both SHe-tGCN4 and mHBc-SHe(cc$_4$s) vaccination induce SHe peptide-specific antibodies. Panel A, The figure represents the titers of SHe-specific IgG antibodies present in the pooled sera of mice of the indicated groups after the first immunization, the first boost immunization (boost) and the second boost immunization (boost 2), as analyzed by SHe peptide ELISA. Panel B, The figure represents the titers of SHe-specific IgG, IgG1 and IgG2a antibodies present in the pooled sera of mice of the indicated groups after the second boost immunization, as determined by peptide ELISA.

Figure 11:
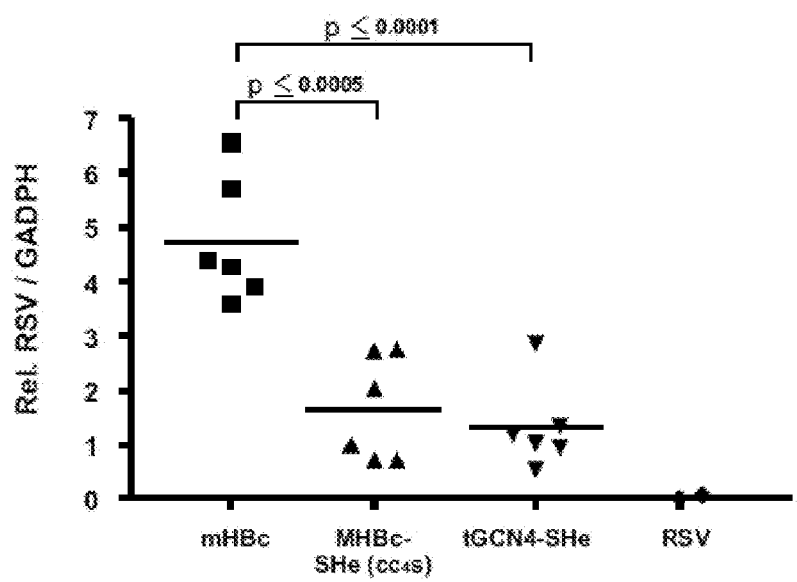
Figure 11:
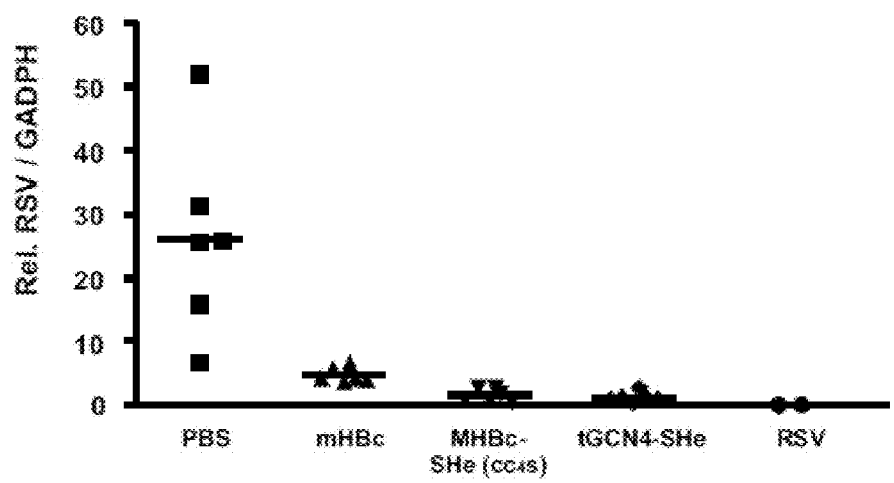

FIG. 11: Both SHe-tGCN4 and mHBc-SHe(cc$_4$s) vaccination decrease pulmonary RSV replication. Three days after challenge, the mice were sacrificed to determine the viral lung titer by QRt-PCR. The upper graph represents the relative expression of genomic RSV RNA, normalized to the GADPH mRNA levels present in the samples of each mouse in the indicated groups. The statistical differences between the vaccinated groups are indicated. The lower panel (B) is identical to the upper panel (A) but also includes the results from the PBS-vaccinated mice.

Figure 12:
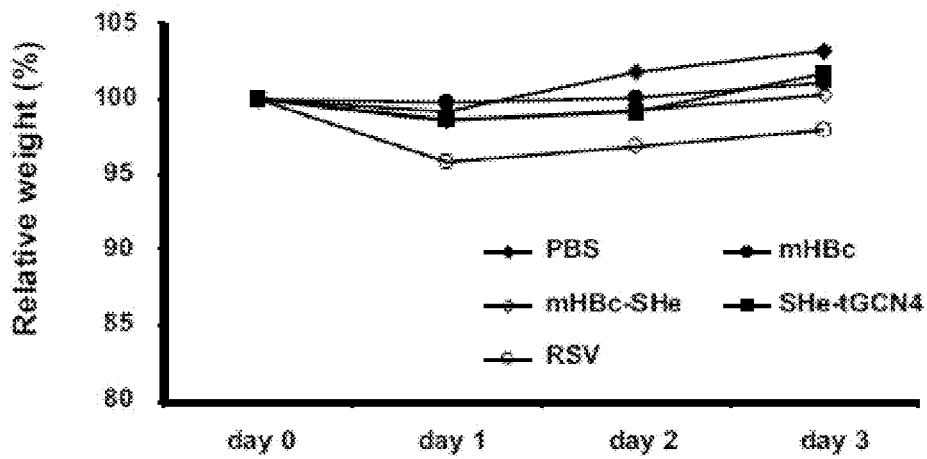

FIG. 12: Neither mHBc-SHe(cc$_4$s) nor tGCN4-SHe vaccination induces enhanced disease upon RSV infection. The figure shows the average relative bodyweight of each indicated group of mice, calculated as the ratio between the weight at the indicated day and the weight at the day of infection (day 0), multiplied by 100.

Figure 13:
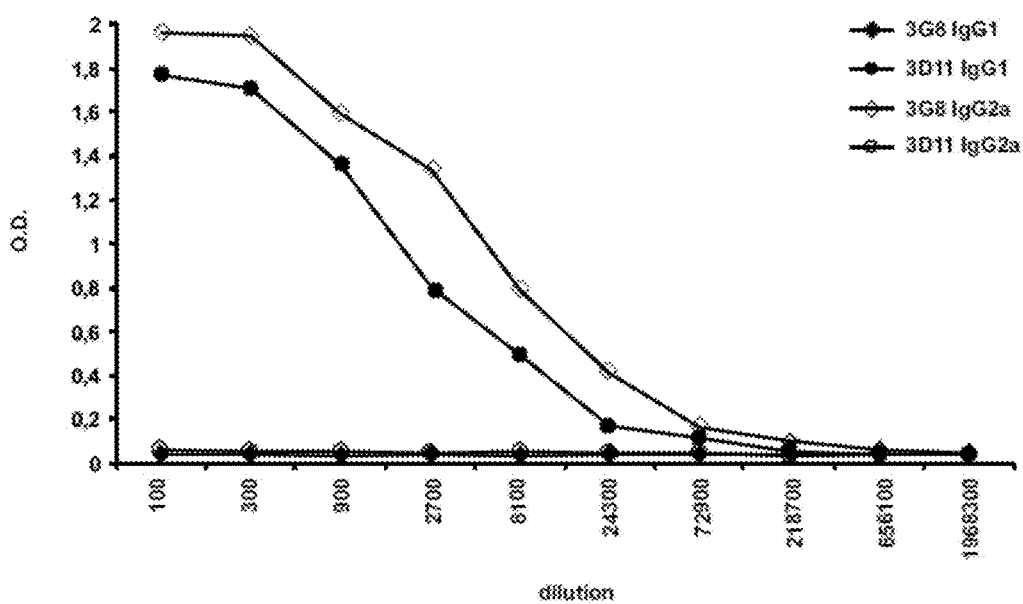

FIG. 13: 3D11 and 3G8 are two SHe-specific monoclonal Abs of, respectively, the IgG1 and IgG2a subtype. The graph shows the binding of dilution series of 1 µg/µl of the 3D11 and 3G8 monoclonal antibodies to SHe peptide in an ELISA assay detected by either mouse IgG1- or mouse IgG2a-specific secondary antibodies.

Figure 14:
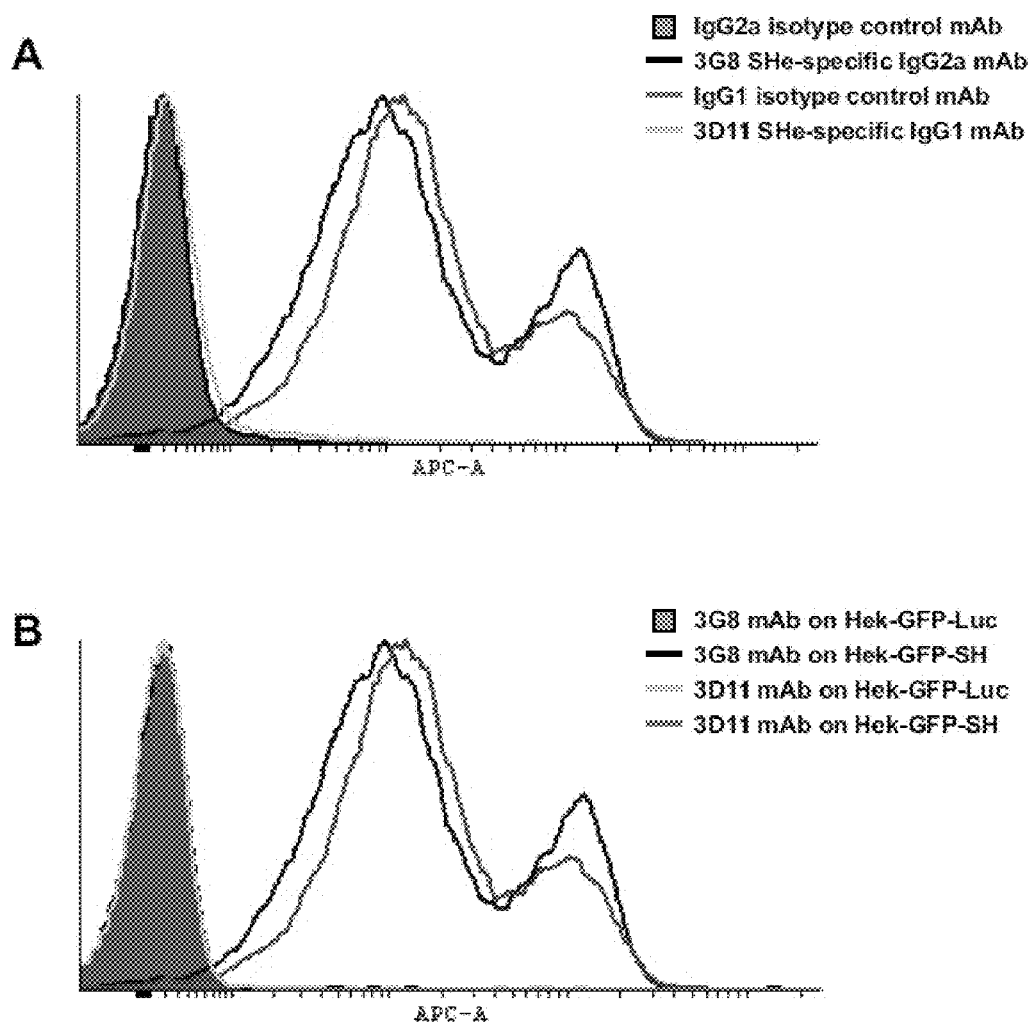

FIG. 14: 3D11 and 3G8 mAbs bind to the RSV SH ectodomain on living cells expressing the RSV SH protein on their cell surface. Panel A, Flow cytometric analysis of the binding of 3D11 and 3G8 mAbs and respective isotype matched control antibodies to Hek293T cells expressing GFP and the RSV SH protein. Panel B, Flow cytometric analysis of the binding of 3D11 and 3G8 mAbs to Hek293T cells expressing GFP in combination with either the RSV SH protein or a control protein (luciferase).

Figure 15:
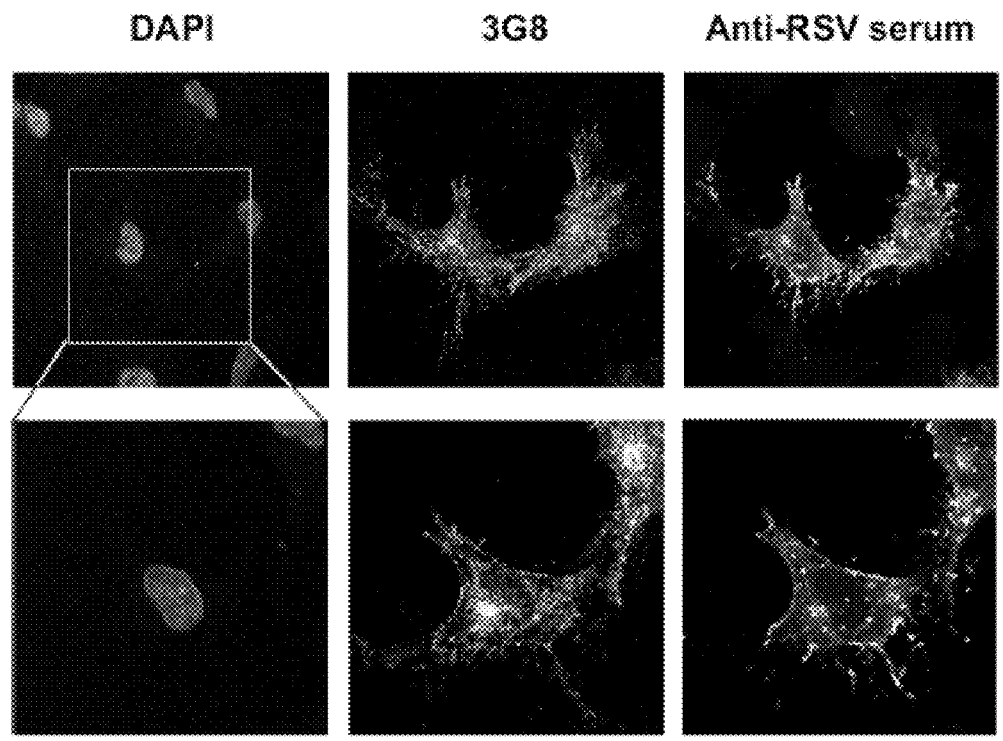

FIG. 15: Binding of 3D11 and 3G8 mAbs to the cell surface of RSV-infected cells. Vero cells were infected with 0.5 MOI of RSV A2. Twenty hours after transfection, the cells were fixed, permeabilized and stained with 3D11 or 3G8 in combination with a polyclonal anti-RSV serum to identify the infected and non-infected cells. The upper panels represent an overview of the immunostaining (DAPI nuclear stain, 3D11 and polyclonal RSV serum), including infected and non-infected cells. The lower panels represent confocal images of an infected cell, indicated in the upper panel.

Figure 16:
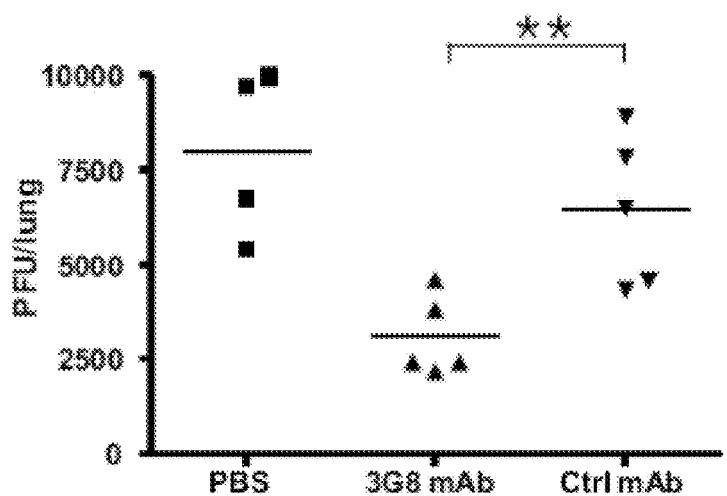

FIG. 16: Passive immunization with SHe-specific monoclonal antibodies reduced RSV infection in mice. Balb/c mice were treated with PBS, SHe-specific 3G8 mAbs or isotype control antibodies via intranasal administration one day before and one day after RSV challenge. Each symbol represents the lung virus titer of individual mice, four days after RSV challenge (** p≤0.01).

Figure 17:
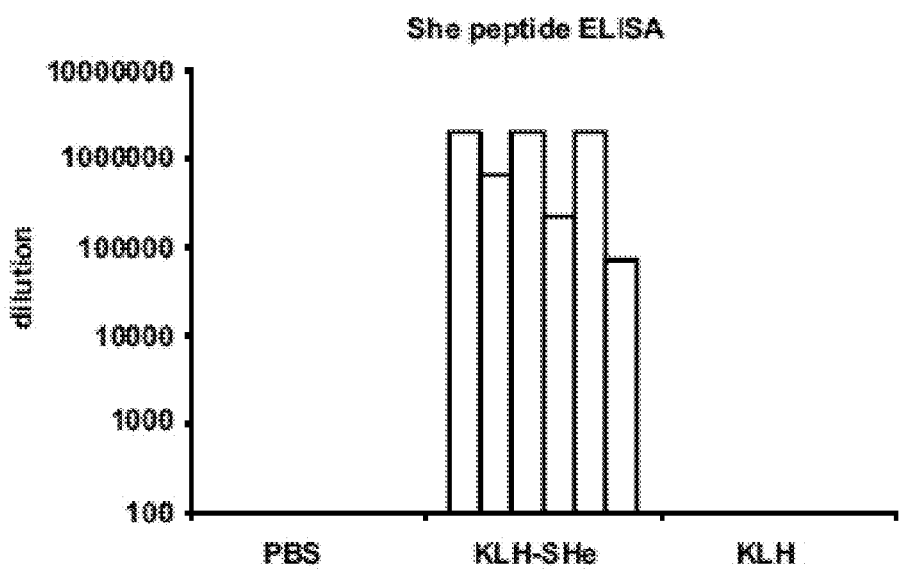
Figure 17:
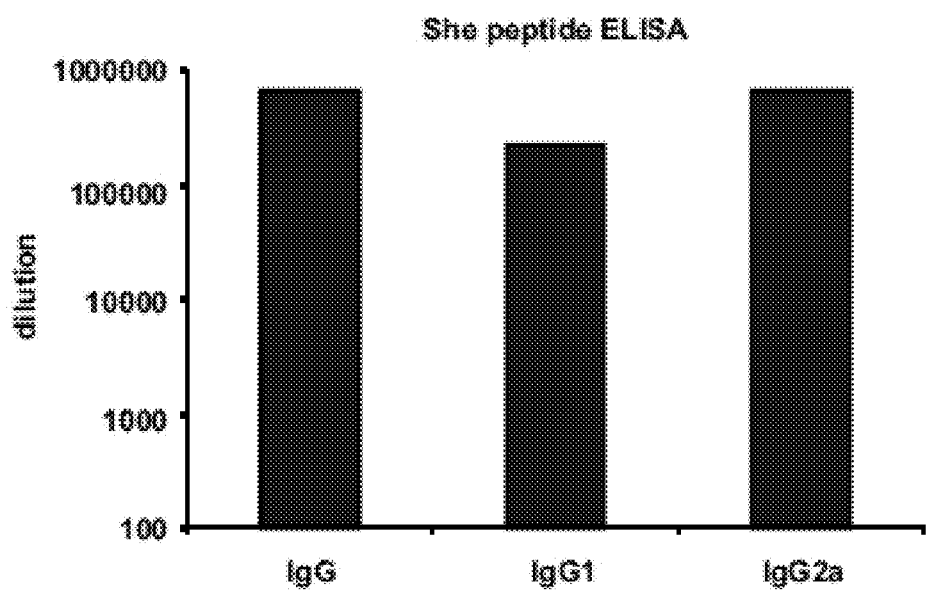
Figure 17:
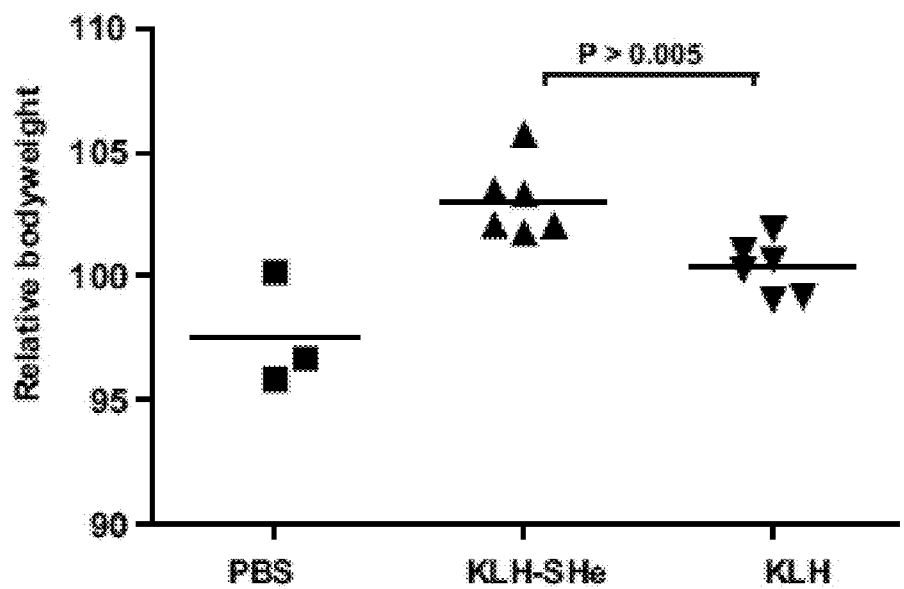
Figure 17:
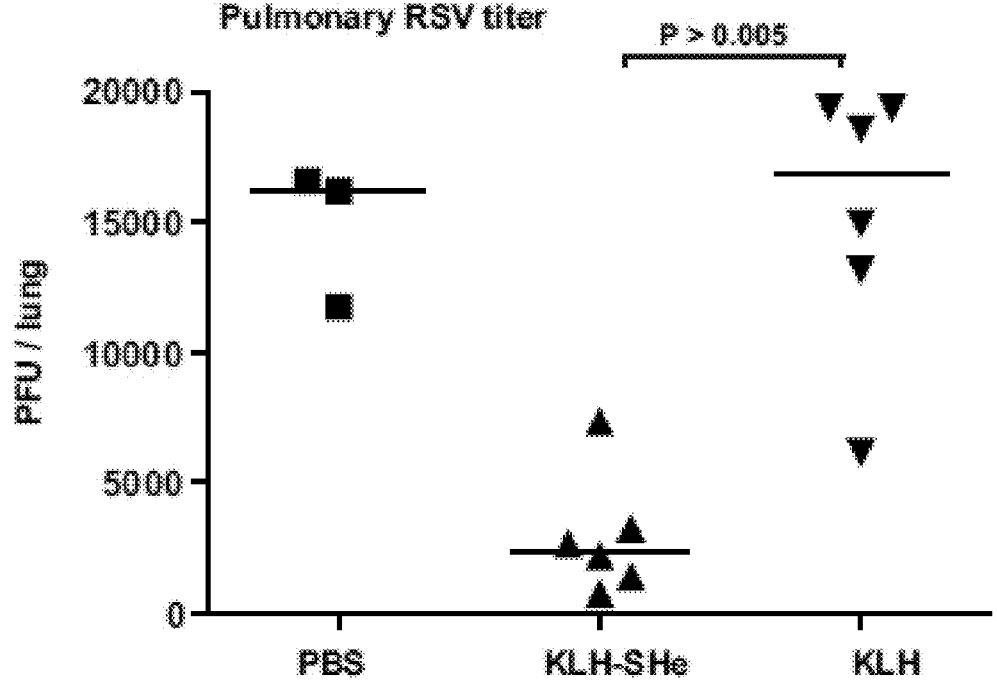
Figure 17:
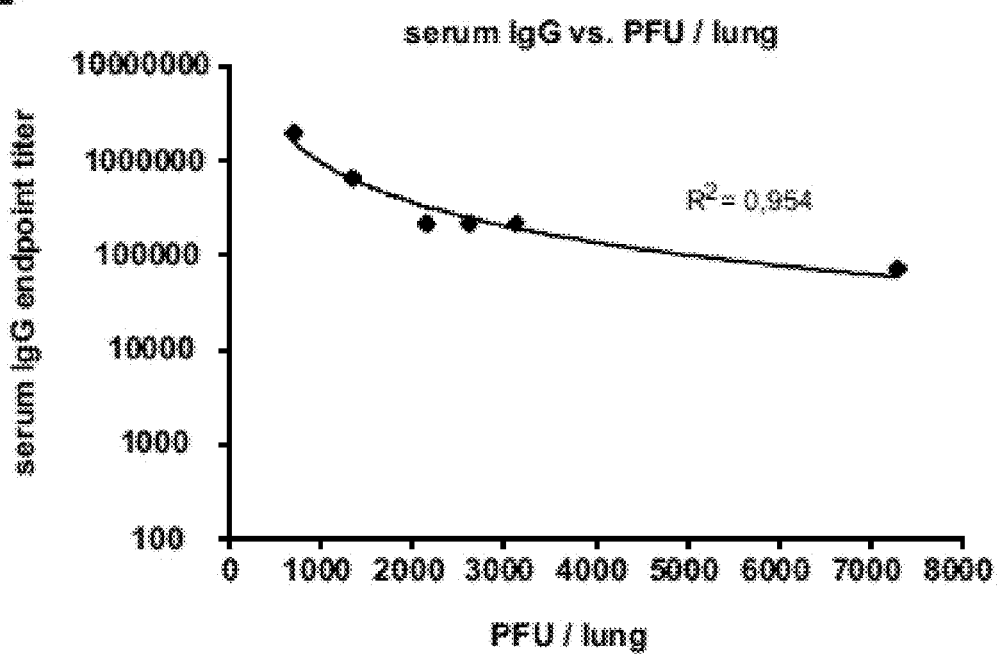

FIG. 17: Intraperitoneal vaccination of Balb/c mice with KLH-SHe in combination with Freund's Incomplete Adjuvant induces SHe-specific antibodies and reduces RSV replication. Panel A, ELISA-based determination of the SHe-specific IgG antibodies present in the sera of individual mice after the third immunization (boost 2) with the indicated vaccines. Panel B, ELISA-based determination of SHe-specific IgG, IgG1 and IgG2a antibodies present in the pooled sera of mice that were vaccinated with the KLH-SHe. Panel C, KLH-SHe vaccination does not induce enhanced disease upon RSV infection. The graph shows the relative body weight of each mouse, calculated as the ratio between the weight on the day of sacrifice (five days after infection) and the weight on the day of viral infection, multiplied by 100. The difference in relative body weight between the KLH-SHe-vaccinated and the KLH-vaccinated mice is significant (p≤0.005, Mann-Whitney U test). Panel D, KLH-SHe vaccination impairs RSV replication. Five days after challenge with $10^6$ PFU RSV, the mice of the indicated groups were sacrificed and lung homogenates were prepared to determine the viral lung titer by plaque assay. The graph shows the number of plaque forming units per lung of each mouse. The detection limit of the plaque assay is 20 PFU per lung. The difference in RSV lung titer between the KLH-SHe-vaccinated and the KLH-vaccinated mice is significant (p≤0.005, Mann-Whitney U test). Panel E, For KLH-SHe-vaccinated mice, high titers of SHe-specific serum antibodies strongly correlate with reduction of RSV replication. The graph shows for each KLH-SHe-vaccinated mouse, the titer of SHe-specific serum IgG antibodies and the number of PFU/lung that could be detected five days after infection. In the graph, the best fitting curve (power) and its R2 (coefficient of determination) are shown.

Figure 18:
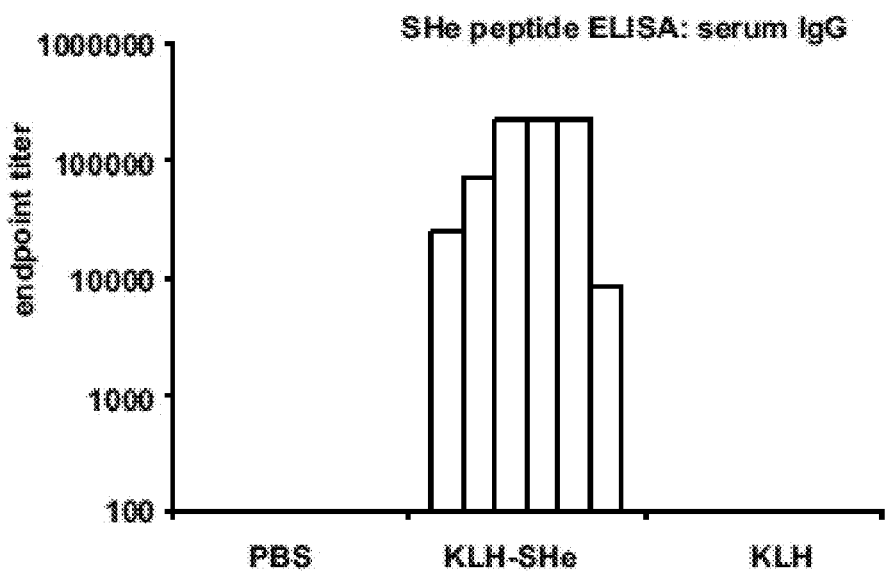
Figure 18:
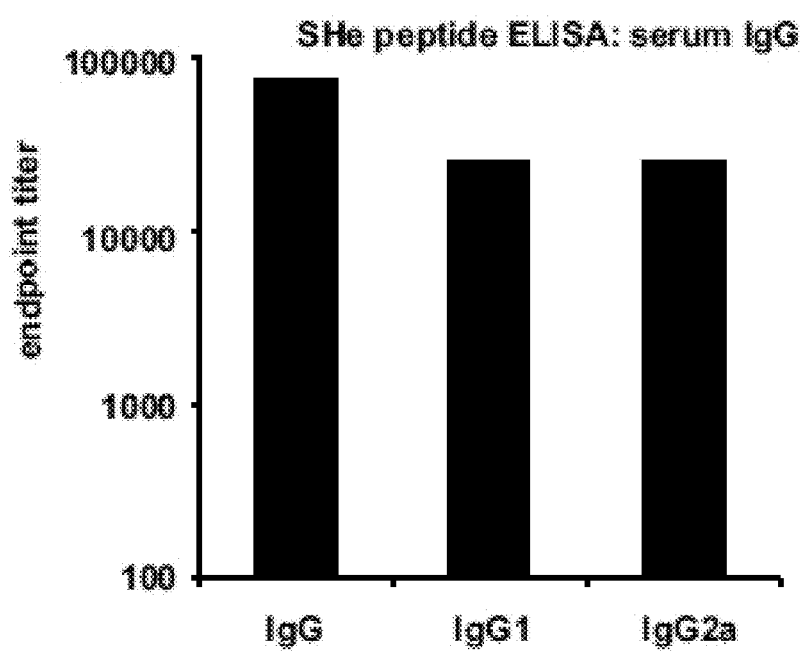
Figure 18:
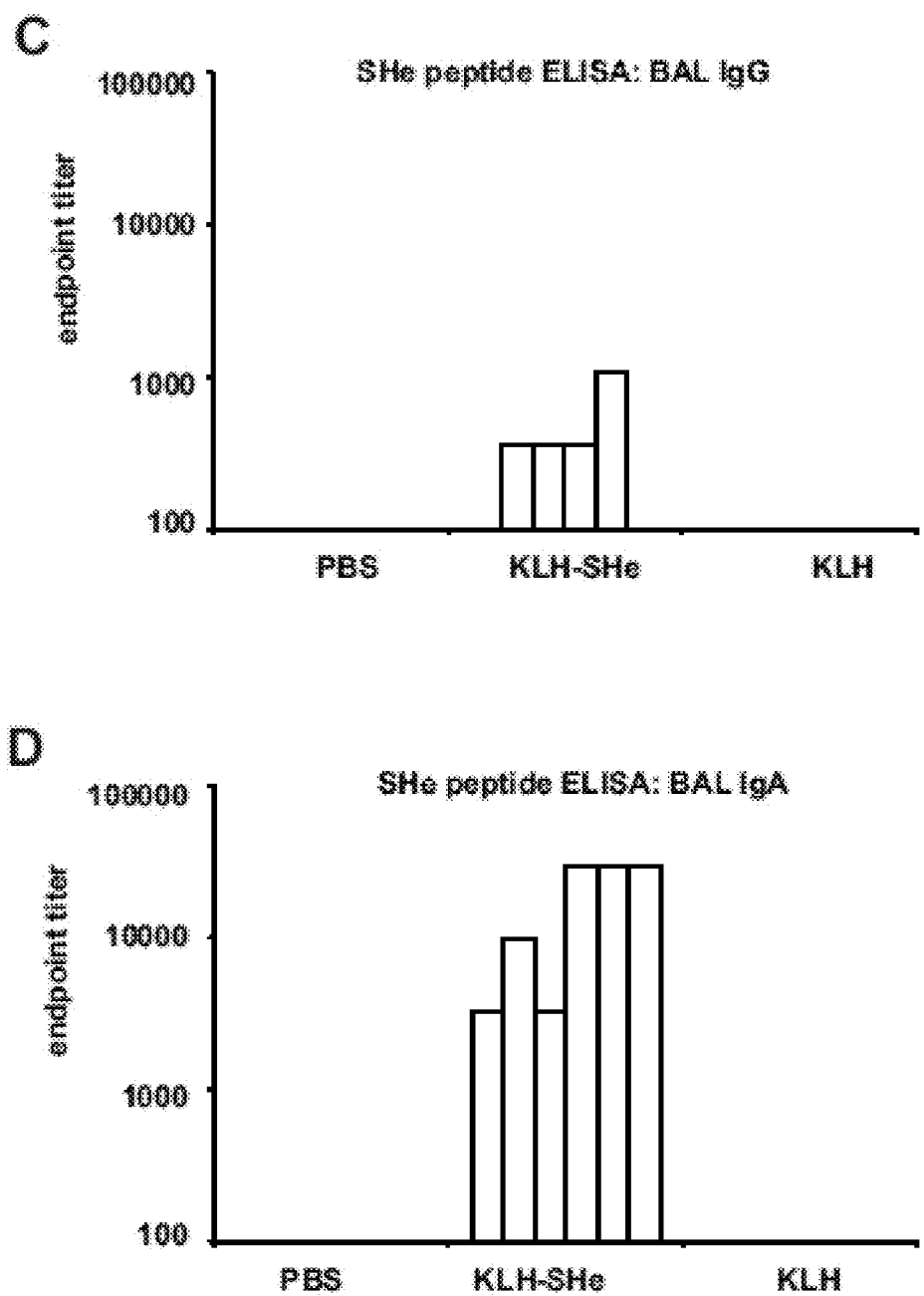
Figure 18:
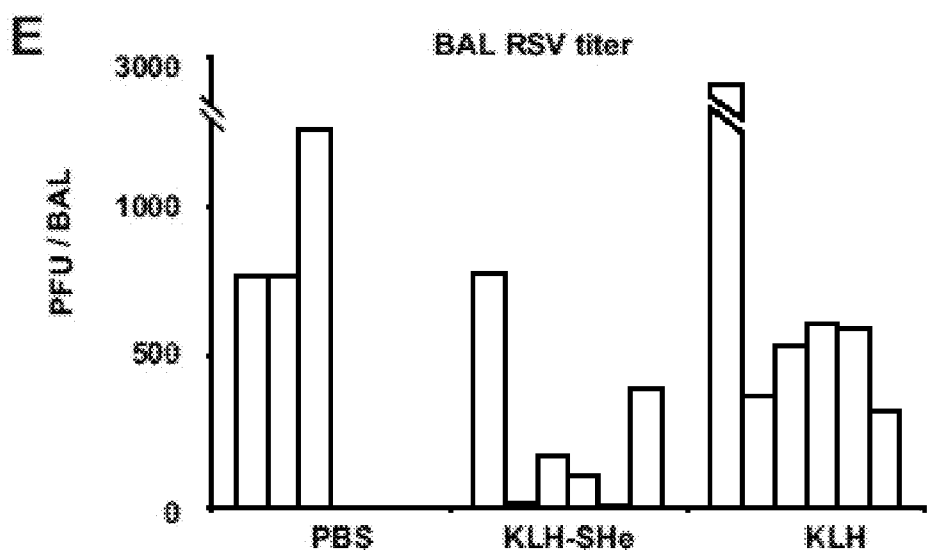
Figure 18:
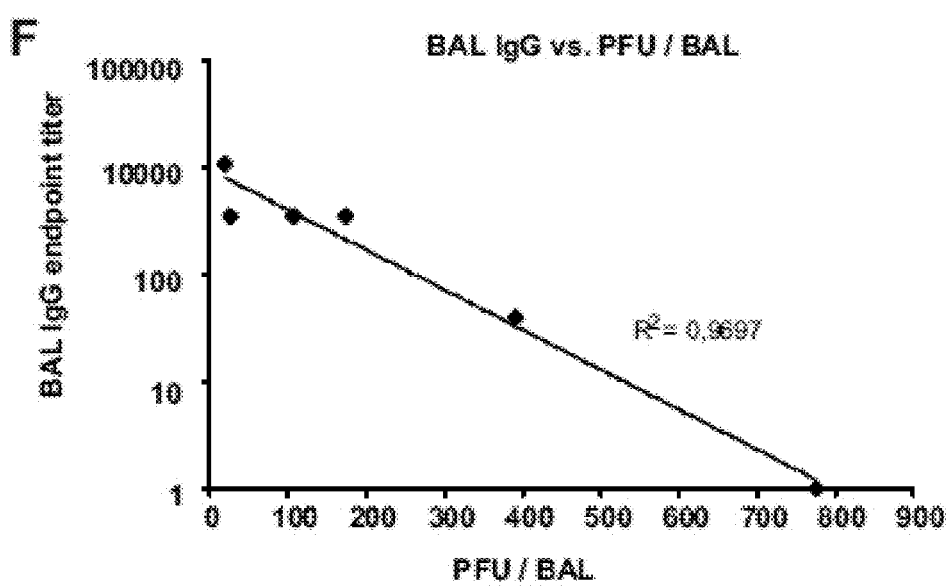

FIG. 18: Intranasal vaccination of Balb/c mice with KLH-SHe in combination with LTR192G induces SHe-specific antibodies and reduces RSV replication. Panel A, ELISA-based determination of the SHe-specific IgG antibodies present in the sera of individual mice after the third immunization (boost 2) with the indicated vaccines. Panel B, ELISA-based determination of the SHe-specific IgG, IgG1 and IgG2a antibodies present in the pooled sera of mice that were vaccinated with KLH-SHe. Panels C and D, ELISA-based determination of the SHe-specific IgG and IgA antibodies present in the BAL fluid of individual mice that were vaccinated with the indicated vaccines and infected with RSV five day before the collection of BAL fluid. Panel E, KLH-SHe vaccination impairs RSV replication. Five days after challenge with 10⁶ PFU RSV, the mice of the indicated groups were sacrificed to determine viral lung titer by plaque assay. The graph shows the number of plaque forming units per lung of each mouse. The detection limit of the plaque assay is 20 PFU per lung. The difference in RSV lung titer between the KLH-SHe-vaccinated and the KLH-vaccinated mice is significant ($p \leq 0.05$, Mann-Whitney U test). Panel F, For KLH-SHe-vaccinated mice, high titers of SHe-specific IgG antibodies present in the BAL fluid strongly correlate with reduction of RSV replication. The graphs show, for each KLH-SHe-vaccinated mouse, the titer of SHe-specific BAL IgG antibodies and the number of PFU/lung that could be detected five days after infection. In the graph, the best fitting curve and its R2 (coefficient of determination) are shown.

Figure 19:
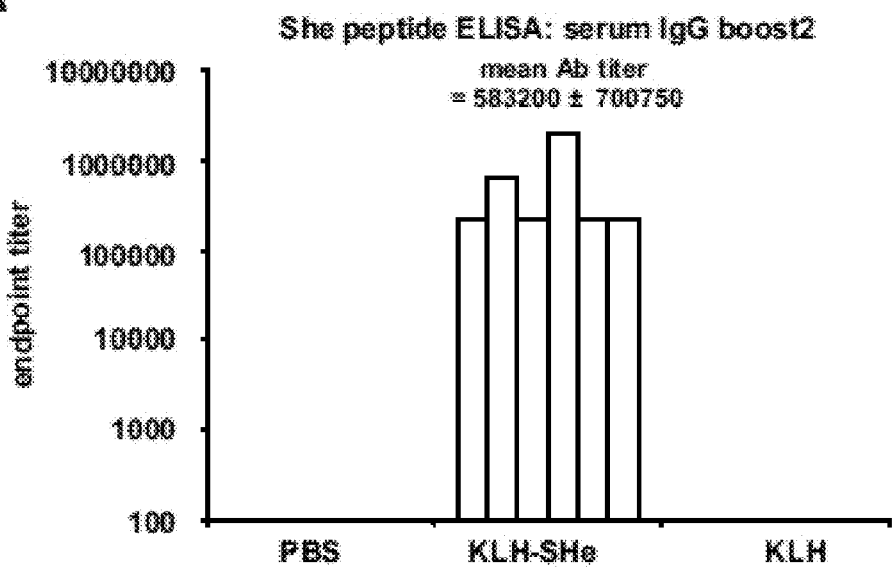
Figure 19:
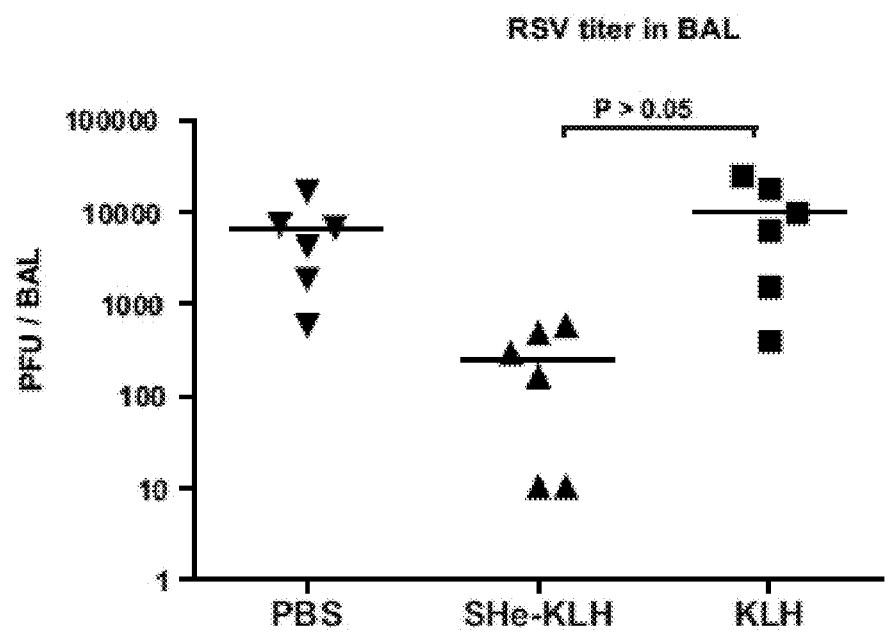
Figure 19:
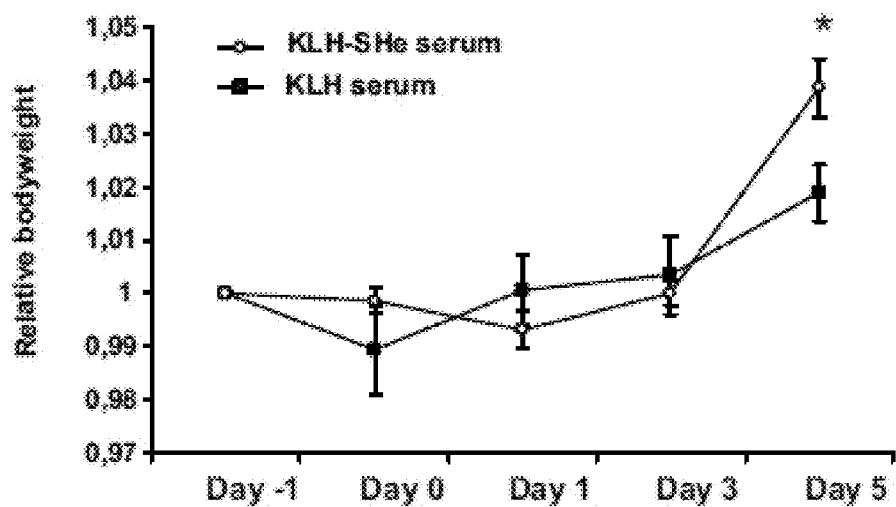

FIG. 19: Passive immunization with KLH-SHe immune serum reduces RSV infection in mice. Panel A, ELISA-based determination of the SHe-specific IgG antibodies present in the sera of individual mice after the third immunization (boost 2) with the indicated vaccines. Panel B, Passive immunization with KLH-SHe immune serum reduces RSV infection in mice. Serum from KLH-SHe- or KLH-vaccinated mice or PBS were administrated intranasally to mice one day before and one day after RSV challenge. Five days after challenge with 10⁶ PFU RSV, the mice of the indicated groups were sacrificed and lung homogenates were prepared to determine the viral lung titer by plaque assay. The graph shows the number of plaque forming units per lung of each mouse. The detection limit of the plaque assay is 20 PFU per lung. The difference in RSV lung titer between the KLH-SHe-vaccinated and the KLH-vaccinated mice is significant ($p \leq 0.05$, Mann-Whitney U test). Panel C, Passive immunization with KLH-SHe serum does not induce enhanced disease upon RSV infection. The graph shows the mean+/−SEM relative body weight of each mouse, calculated as the ratio between the weight at a specific day and the weight at the day of the first passive immunization, multiplied by 100. The difference in relative body weight between the mice that were treated with KLH-SHe serum and the mice that were treated with KLH serum is significant ($p \leq 0.005$, Mann-Whitney U test).

Figure 20:
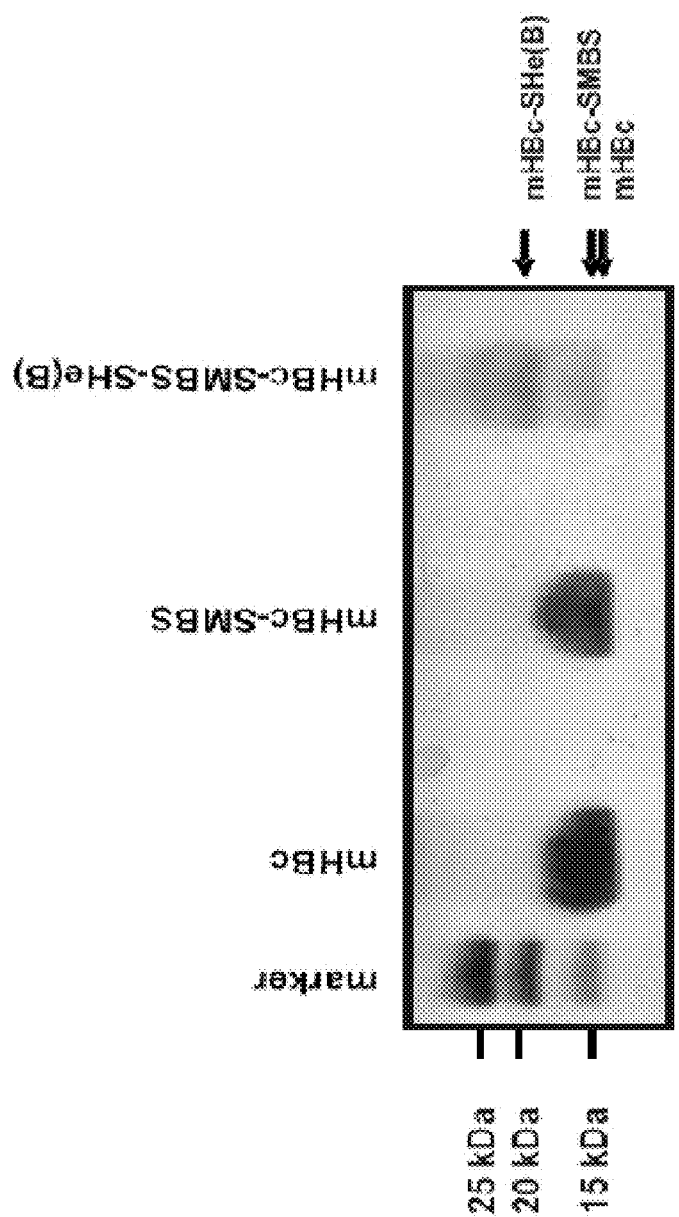

FIG. 20: Chemical linkage of SHeB peptides to the immunodominant loops of mHBc virus-like particles. Coomassie blue stained SDS-PAGE analysis of mHBc VLPs, mHBc VLPs linked to the SMBS heterobifunctional crosslinker (mHBc-SMBS) and purified mHBc-SMBS VLPs with chemically linked SHeB peptides (mHBc-SHeB).

FIG. 21: Binding of Serum of mHBc-SHeB-vaccinated mice to the surface of RSV B infected cells. Vero cells were infected with a RSV B clinical isolate or mock infected. Seventy-two hours after infection, the cells were fixed and either permeabilized or not permeabilized. Infected and mock infected cells were stained with serum of a mHBc-SHeB-vaccinated mouse or with serum of KLH-vaccinated mice, as indicated. Binding of mHBc-B or KLH serum antibodies to the cells was analyzed by using Alexa488 linked anti-mouse IgG antibodies. FIG. 21A, For microscopic analysis, the cells were also stained with the nuclear dye DAPI. FIG. 21B, For flowcytometric analysis, the non-permealized cells were also stained with a goat anti-RSV serum to identify the RSV B infected cells. Binding of goat anti-RSV serum antibodies to the cells was determined by using Alexa633 linked anti-goat IgG antibodies. The graphs represent Alexa488 intensity/Alexa633 intensity contour plots of the indicated cells.

FIG. 22: Vaccination with mHBc-SHeB induces SHeB-specific antibodies and reduces RSV B-induced pulmonary inflammation. Panel A, ELISA-based determination of the SHeB- and SHeA-specific IgG antibodies present in the pooled sera of mice after the first (im.), the second (boost 1) and third mHBc-SHeB immunization (boost 2). Panel B, ELISA-based determination of the SHe-specific IgG, IgG1 and IgG2a antibodies present in the pooled sera of mice that were vaccinated with KLH-SHe. Panels C and D, ELISA-based determination of SHeB- (Panel C) and SHeA-specific (Panel D) IgG antibodies present in the sera of individual mice that were vaccinated with the indicated vaccines. Panel E, The total number of cells present in the BAL fluids of RSV-infected mice that had been vaccinated with the indicated vaccines. There are significantly less cells present in the BAL fluid of mice that had been vaccinated with mHBc-SHe compared to BAL fluid of mice that had been vaccinated with mHBc ($p \leq 0.05$, Maim-Whitney U test). Panel F, The number of CD4+ T cells, CD8+ T cells, monocytes, neutrophils and eosinophils present in the BAL fluids. There are significantly less CD8+ T cells present in the BAL fluid of mice that had been vaccinated with mHBc-SHe compared to the BAL fluid of mice that had been vaccinated with mHBc ($p \leq 0.05$, Mann-Whitney U test).

FIG. 23: Expression and purification of the $LPP_{(5)}$-SHe protein. Panel A, Expression of the $LPP_{(5)}$-SHe protein. pLH36-HisDEVD-$LPP_{(5)}$-SHe transformed *E. coli* cells were either stimulated with 1 mM 1-thio-β-d-galactopryanoside (IPTG) or not. Four hours later, crude extracts were prepared by sonication followed by centrifugation (13 000×g, 30 minutes, 4° C.). The supernatant was analyzed by SDS-PAGE and Western blotting using the SHe-specific 3G8 monoclonal antibody. Panel B, Analysis of purified $LPP_{(5)}$-SHe protein. After purification, the $LPP_{(5)}$-SHe protein was analyzed by SDS-PAGE, Coomassie blue staining (left) and Western blot (right) analysis using the SHe-specific 3G8 monoclonal antibody.

FIG. 24: schedule of the vaccination of the cotton rats. Group numbers refer to: Group 1, six Cotton rats (CR) no vaccine and challenged with RSV on day +63 (infection control); Group 2, six CR inoculated intranasally with RSV-Tracy at $2.04\times10^5$ PFU/CR on Day 0; Group 3, six CR, each vaccinated intraperitoneally (IP) with KLH-SHe+IFA; Group 4, six CR, each vaccinated intraperitoneally (IP) with KLH+IFA (vehicle control); Group 5, six CR, each vaccinated intramuscularly (IM) with 1:10 formalin-inactivated (FI) RSV-Bernett grown in Vero cells (positive control for immune exacerbation upon challenge).

DETAILED DESCRIPTION

Examples

Materials and Methods to the Examples

Cloning and Plasmid Construction

Construction of the pLT32 Flag-COMPcc-SHe Expression Plasmid.

A plasmid containing the coding sequence of Flag-COMPcc-SHe (FIG. 1, Panel B) was ordered at Genscript (SEQ ID NO:31). The Flag-COMPcc-SHe coding sequence was ligated as a NdeI/NotI fragment in a NdeI/NotI opened pLT32H bacterial expression vector (Mertens et al., 1995).

Construction of the pCAGGS-Etag-SH Expression Vector.

Total RNA of RSV A2-infected Hep-2 cells was prepared using the High Pure RNA tissue kit (Roche, Mannheim) according to the manufacturer's instructions. After cDNA synthesis, the RSV A2 SH coding sequence was amplified using the following forward and reverse primers (5'ATAAGAAAGCGGCCGCTATGGAAAATACATCCATAACAATAG3' (SEQ ID NO:36); 5'GAAGATCTCTAT- GTGTTGACTCGAGCTCTTGGTAACTCAAA3' (SEQ ID NO:37)). The PCR product was digested with NotI and BglII and ligated in a NotI/BglII opened pCAGGS-PTB-Etag expression vector (Cornelis et al., 2005). The resulting vector pLT32-Flag-COMPcc-SHe was deposited under the Budapest treaty at BCCM (BCCM/LMBP: Technologiepark 927, 9052 Zwijnaarde, Belgium) under deposit number LMBP 6817 on 8 Nov. 2010.

The construction of the pCAGGS-Luc expression vector was described earlier (Schepens et al., 2005; referred as pCAGGS-HIF-RLuc).

Construction of the pLT32 mHBc Expression Vector.

The coding sequence of mHBc, as described earlier by Jegerlehner et al., as part of the "abi" plasmid, was ordered at Geneart (SEQ ID NO:32) (De Filette et al., 2005; Jegerlehner et al., 2002). This coding sequence was cloned as a NdeI/NotI fragment in a NdeI/NotI opened pLT32H bacterial expression vector.

Construction of the pLT32 SHe-tGCN4-Flag Expression Vector.

To construct pLT32 SHe-tGCN4, the SHe coding sequence was fused to the tGCN4-Flag coding sequence by fusion per. The SHe fragment for fusion per was amplified using the primers: 5'GGAATTCCATATGAACAAGTTATGTGAG-TACAACG3' (SEQ ID NO:38) and 5'GATTTGTTTTAAAC-CTCCTGTATTTACTCGTGCCCGAGGCAA3' (SEQ ID NO:39) and a template plasmid that was ordered at Geneart (SEQ ID NO:33) and that contains the coding sequence of the RSV A2 SH ectodomain (NKLCEYNVFHNKTFEL-PRARVNT) (SEQ ID NO:40). The GCN4 fragment for fusion PCR was amplified using the primers 5'CCCAAGCT-TCTAACATTGAGATTCCCGAGATTGAGA3' (SEQ ID NO:41) and 5'TATTAACCCTCACTAAAGGGAAGG3' (SEQ ID NO:42) and a template plasmid that contains the tGCN4 coding sequence, C-terminally fused to the coding sequence of three successive Flag-tag sequences (SEQ ID NO:34; De Filette et al., 2008). The two PCR fragments were fused using the primers: 5'GGAATTCCATATGAACAAGT-TATGTGAGTACAACG3' (SEQ ID NO:43) and 5'TAT-TAACCCTCACTAAAGGGAAGG3' (SEQ ID NO:44). This fusion PCR product was cloned as a NdeI/HindIII fragment in a NdeI/HindIII opened pLT32H bacterial expression vector. The resulting pLT32 SHe-tGCN4-Flag was deposited under the Budapest treaty at BCCM (BCCM/LMBP: Technologiepark 927, 9052 Zwijnaarde, Belgium) under deposit number LMBP 6818 on 8 Nov. 2010.

The construction of the PLT32 M2e-tGCN4 expression vector was described earlier (De Filette et al., 2008).

Construction of the pLH36-HisDEVD-LPP$_{(5)}$-SHe Expression Plasmid.

A plasmid containing the coding sequence of the LPP$_{(5)}$ tryptophan-zipper fused to the coding sequence of the SH ectodomain separated by the coding sequence of a GlyGly linker was ordered at Genscript. This coding sequence was amplified using the following forward and reverse primers (5'GCGAAATGGGATCAGTGGAGCAGC-3' (SEQ ID NO:53); 5'AATATAGGATCCCTAGGTCGCCCAGT-TATCCCAGCG-3' (SEQ ID NO:54)), phosphorylated and digested with BamHI. The pLH36-HisDEVD-LPP-SHe was constructed by a three-point ligation using the described PCR fragment, BamHI/PstI-digested pLT32 plasmid fragment and EcoRV/PstI-digested pLH36 fragment. The sequence of the constructed pLH36-HisDEVD-LPP$_{(5)}$-SHe plasmid is displayed in SEQ ID NO:49.

Expression and Purification of SHe-tGCN4, M2e-tGCN4, Flag-COMPcc-SHe, mHBc and LPP$_{(5)}$-SHe A 30-ml preculture of pLT32SHe-tGCN4-transformed E. coli was grown at 28° C. in Luria broth and used to inoculate 1 liter of fresh medium. At an A600 of 0.6-0.8, the cells were treated with 1 mm isopropyl 1-thio-β-d-galactopyranoside, incubated for another four hours, and then collected by centrifugation (6000×g, 20 minutes, 4° C.). The bacterial pellet was resuspended in 20 ml Tris-HCl buffer (50 mM Tris-Hcl, 50 mM NaCl and 1 mM EDTA), pH 8, and sonicated. Bacterial debris was pelleted by centrifugation (20,000×g, one hour, 4° C.). The supernatant was applied to a DEAE Sepharose column pre-equilibrated with Tris-HCl buffer containing 50 mM NaCl (buffer A). After washing, the bound proteins were eluted by a two-step gradient going from 0-40% buffer B (50 mM Tris-Hcl, 1 M NaCl) and 40-100% buffer B. Fractions containing SHe-tGCN4 were pooled, adjusted to 25% ammonium sulfate saturation, and applied to a phenyl-Sepharose column pre-equilibrated with 25% ammonium sulfate, 50 mm Tris-HCl, pH 8. Bound proteins were eluted with a two-step gradient. The two-step elution was performed with 0-40% and 40-100% 50 mM Tris-HCl buffer, pH 8 (buffer A). The fractions containing SHe-tGCN4 were loaded on a Superdex 75 column. Gel filtration was performed in phosphate-buffered saline (PBS), and the fractions containing SHe-tGCN4 were pooled and stored at −70° C.

Expression and purification of flag-COMPcc-SHe was identical to SHe-tGCN4 apart from the use of a Q Sepharose column for anion exchange chromatography instead of a DEAE Sepharose column.

The expression and purification of M2e-tGCN4 was described before (De Filette et al., 2008).

Expression and purification of mHBc was identical to SHe-tGCN4 apart from the use of a Sephacryl S400 column for gel filtration chromatography instead of Superdex 75 column.

Expression and Purification of LPP$_{(5)}$-SHe.

A 30-ml preculture of pLH36-HisDEVD-LPP$_{(5)}$-SHe-transformed E. coli cells was grown at 28° C. in Luria broth with ampicillin and used to inoculate 3 liters of fresh medium. At an A$_{600}$ of 0.6-0.8, the cells were treated with 1 mM isopropyl 1-thio-β-d-galactopyranoside, incubated for another four hours, and then collected by centrifugation (6000×g, 20 minutes, 4° C.). The bacterial pellet was resuspended in 300 ml buffer containing 20 mM NaH$_2$PO$_4$/Na$_2$HPO$_4$, 300 mM NaCl and 5 mM imidazole, pH 7.5 and sonicated. Bacterial debris was pelleted by centrifugation (20,000×g, one hour, 4° C.). The supernatant was loaded on a Nickel-Sepharose column pre-equilibrated with buffer containing 5 mM Imidazole. After washing, the bound proteins were eluted by a step-wise (50 mM, 100 mM, 200 mM and 400 mM) imidazole gradient. Fractions containing LPP$_{(5)}$-SHe were pooled, desalted and further purified on a Q-sepharose column. The sample was applied to a DEAE Sepharose column pre-equilibrated with Tris-HCl buffer containing 50 mM NaCl (buffer A). After washing, the bound proteins were eluted by a two-step gradient going from 0-40% buffer B (50 mM Tris-Hcl, 1 M NaCl) and 40-100% buffer. The fractions containing LPP$_{(5)}$-SHe were loaded on a Superdex 75 column. Gel filtration was performed in phosphate-buffered saline (PBS) and the fractions containing LPP$_{(5)}$-SHe.

Adjuvants

A detoxified mutant of heat-labile E. coli enterotoxin, LTR192G, was used for intranasal (i.n.) administration; this preparation was generously provided by Dr. J. Clements (Department of Microbiology and Immunology, Tulane University Medical Center, New Orleans, La., USA) (Norton et al., 2010).

Chemical Linking and Characterization of SHe-HBc Particles

SHe(cc4s), a chemically synthesized, HPLC-purified SHe peptide in which the naturally occurring cysteine was replaced by a serine and to which a cysteine was added at the N-terminus was ordered at Pepscan (Pepscan, Lelystad). The SHe(cc4s) peptide was via its N-terminal cysteine residue fused to a Lysine in the immunodominant loop of mHBc on the surface of HBc VLPs by chemical linkage using the heterobifuctional sulfo-MBS (Pierce), according to the manufacturer's instructions. In short, 400 µg mHBc, dissolved in 200 µl PBS, was incubated with Sulfo-MBS (at a final concentration of 1 mg/ml) for one hour. After removal of unbound Sulfo-MBS molecules by size exclusion chromatography, sulfo-MBS-linked mHBc VLPs were diluted in 2 ml $H_2O$, Subsequently, 100 µl SHe(cc4s) peptide (dissolved in 100 ml PBS) was added and incubated for one hour at room temperature to allow cross-linking of the peptide to the mHBc VLPs. Finally, free SHe(cc4s) peptide was removed by size exclusion chromatography. The purity and cross-linking efficacy was tested via SDS-PAGE followed by Coomassie staining.

Cells

Hep-2 cells (ATCC, CCL-23), Vero cells (ATCC, CCL-81), HEK293T cells (a gift from Dr. M. Hall) and A549 cells (ATCC, CCL-185) were grown in DMEM medium supplemented with 10% heat-inactivated fetal calf serum (FCS), 1% penicillin, 1% streptomycin, 2 mM L-glutamine, non-essential amino acids (Invitrogen, Carlsbad, Calif.), and 1 mM sodium pyruvate.

Mice and Viruses

Specific pathogen-free, female BALB/c mice were obtained from Charles River (Charles River Wiga, Sulzfeld, Germany). The animals were housed in a temperature-controlled environment with 12-hour light/dark cycles; food and water were delivered ad libitum. Mice were immunized at 8 weeks of age after one week adaptation in the animal room.

The animal facility operates under the Flemish Government License Number LA1400091. All experiments were done under conditions specified by law (European Directive and Belgian Royal Decree of Nov. 14, 1993) and authorized by the Institutional Ethical Committee on Experimental Animals.

RSV A2, an A subtype of RSV (ATCC, Rockville), was propagated by infecting monolayers of Vero cells, with 0.1 MOI in the presence of growth medium containing 1% FCS. Five to seven days after infection, the cells and growth medium were collected, pooled and clarified by centrifugation (450×g). To concentrate the virus, the clarified supernatant was incubated for four hours at 4° C. in the presence of 10% polyethylene glycol (PEG6000). After centrifugation (30 minutes at 3000×g), the pellet was resuspended in Hank's balanced salt solution (HBSS), containing 20% sucrose, aliquoted and stored at −80° C.

Intranasal Immunizations and Infections

For intranasal immunization or infection, the mice were slightly anesthetized by isofluorane. The final volume used for administration of vaccine+adjuvant or virus was 50 µl (25 µl per nostril). Vaccines+adjuvant were formulated in PBS, whereas the viral inoculum was formulated in HBSS.

Determination of Lung Viral Titer by Plaque Assay

Three or four days post-challenge, the mice were sacrificed. The mouse lungs were removed aseptically and homogenized with a Heidolph RZR 2020 homogenizer for 30 seconds in 1 ml HBSS containing 10% sucrose. Lung homogenates were subsequently cleared by centrifugation at 4° C. and used for virus titration on Hep-2 cells. Monolayers of Hep-2 cells were infected with 50 µl of serial 1:3 dilutions of the lung homogenates in a 96-well plate in serum-free OPTI-MEM® medium (Invitrogen) supplemented with penicillin and streptomycin. Four hours later, the cells were washed twice with DMEM medium containing 2% FCS and incubated for five days at 37° C. in 50 µl overlay medium (completed DMEM medium containing 1% FCS, 0.5% agarose). The cells were fixed by adding 50 µl of a 4% paraformaldehyde solution on top of the agarose overlay. After overnight fixation at 4° C., the overlay medium and paraformaldehyde solution were removed, the cells were washed twice with PBS and blocked with PBS containing 1% BSA (PBS/BSA). Subsequently, polyclonal goat anti-RSV serum (AB1128, Chemicon International) was added (1/4000). After washing three times with PBS/BSA, the cells were incubated with hrp-conjugated anti-goat IgG antibodies (SC2020, Santa Cruz) for 30 minutes. Non-binding antibodies were removed by washing four times with PBS/BSA containing 0.01% TRITON® X-100 and once with PBS. Finally, the plaques were visualized by the use of TrueBlue peroxidase substrate (KPL, Gaithersburg). The plaques of different dilutions were counted and, for each dilution, the number of PFU per lung (1 ml) was calculated as: number of plaques present in the dilution×the dilution×20 (=1000 µl total supernatant volume/50 µl of the volume of supernatant used to infect the first well of the dilution series). The number of PFU/lung was then calculated as the average number of PFU/lung calculated for the different dilutions. As each supernatant of the homogenized lungs was tested in duplicate, the final number of PFU/lung was calculated as the average of these duplicates.

Determination of Lung Viral Titer by qRT-PCR

To determine the lung RSV load by qRT-PCR, lung homogenates were prepared and clarified as described above. Total RNA from these lung homogenates was prepared by the use of the High Pure RNA tissue kit (Roche, Mannheim) according to the manufacturer's instructions. cDNA was prepared by the use of hexamer primers and the Transcriptor First Strand cDNA synthesis kit (Roche, Mannheim). The relative levels of genomic RSV M cDNA were determined by the use of qRT-PCR using primers specific for the genomic RNA of the RSV A2 M-gene (5'TCACGAAGGCTCCACATACA3' (SEQ ID NO:45) and 5'GCAGGGTCATCGTCTTTTTC3' (SEQ ID NO:46)) and a nucleotide probe (#150 Universal Probe Library, Roche) labeled with fluorescein (FAM) at the 5'-end and with a dark quencher dye near the −3' end. The relative amount of GADPH mRNA was determined by qRT-PCR using primers specific for mouse GADPH (5'TGAAG-CAGGCATCTGAGGG3' (SEQ ID NO:47) and 5'CGAAG-GTGGAAGAGTGGGAG3' (SEQ ID NO:48) and LIGHTCYCLER® 480 SYBR® Green I Master Mix (Roche). The relative amount of genomic RSV RNA per lung homogenate was calculated as the ratio between the relative amount of RSV M-gene RNA and the relative amount of mouse GADPH mRNA.

Peptide ELISA

Two weeks after each immunization, blood samples were collected from the lateral tail vein. The final bleeding was performed by cardiac puncture of animals anesthetized with avertin. Blood was allowed to clot for 30 minutes at 37° C., and serum was obtained by taking the supernatant from two subsequent centrifugations.

Serum antibody titers were determined by ELISA using pooled sera from the group. To determine M2e or SHe-specific antibody titers, microtiter plates (type II F96 MaxiSorp, Nunc) were coated with, respectively, 50 µl of a 2 µg/ml M2e-peptide solution or 2 µg/ml SHe-peptide solution in 50 mM sodium bicarbonate buffer, pH 9.7, and incubated overnight at 37° C. After washing, the plates were blocked for one hour with 200 μl of 1% BSA in PBS. After a one-hour incubation, the plates were washed again. A series of 1/3 dilutions of the different serum samples, starting with a 1/100 dilution, were loaded on the peptide-coated plates. The bound antibodies were detected with a peroxidase-labeled antibody directed against mouse isotypes IgG1 or IgG2a (Southern Biotechnology Associates, Inc., Birmingham, Ala., USA) and diluted 1/6000 in PBS+1% BSA+0.05% TWEEN® 20. After washing, the microtiter plates were incubated for five minutes with TMB substrate (Tetramethylbenzidine, Sigma-Aldrich). The reaction was stopped by addition of an equal volume 1 M H3PO4 and the absorbance at 450 nm was measured. Endpoint titers are defined as the highest dilution producing an O.D. value twice that of background (pre-immune serum).

Flow Cytometric Analysis

Hek293T cells were transfected with the indicated expression vectors. Twenty-four hours later, the cells were detached using enzyme-free dissociation buffer (Invitrogen, Carslbad, Calif.), washed once with PBS and incubated for one hour in PBS containing 1% BSA (PBS/BSA). Subsequently, the cells were incubated with the indicated serum or antibodies at the indicated concentrations. One hour later, the cells were washed three times with PBS/BSA and incubated with the anti-mouse IgG alexa 633 secondary antibodies for 30 minutes. After washing the cells four times with PBS/BSA and once with PBS, the cells were analyzed using a Becton Dickinson LSR II flow cytometer. Single GFP-expressing cells were selected based on the peak surface of the sideward scatter signal, the peak surface and peak height of the forward scatter signal and the peak surface of the green fluorescence signal. Finally, of these GFP-positive single cells, the alexa 633 fluorescence signal was measured.

Immunostaining

Vero cells were either mock infected or infected with 0.5 MOI of RSV A2 in the presence of serum-free medium. Four hours later, the free virus was washed away and the cells were incubated in growth medium containing 1% FCS. Sixteen hours later, the cells were washed once with PBS and fixed with 2% paraformaldehyde for 20 minutes. Subsequently, the cells were washed twice with PBS and permeabilized with 0.2% TRITON® X-100 detergent for five minutes. After washing once with PBS, the cells were blocked in PBS/BSA. One hour later, SHe-specific 3G8 monoclonal antibody or isotype control antibody was added at a final concentration of 5 μg/ml. After washing the cells twice with PBS/BSA, polyclonal anti-RSV goat serum was added. One hour later, the cells were washed three times with PBS/BSA. The binding of the indicated antibodies to the cells was analyzed by the use of anti-mouse and anti-goat IgG antibodies labeled with, respectively, alexa 488 and alexa 568 fluorescent dyes. Confocal images of the stained cells were recorded with a Zeiss confocal microscope.

Generation of SHe mAb Producing Hybridomas

Stable hybridomas cells producing SHe-specific monoclonal antibodies (mAb) were generated by hybridoma technology (Kohler and Milstein 1975). Briefly, SHe-specific hybridomas were derived from individual mice that were immunized i.p. three times at three-week intervals with 10 μg of SHe-tGCN4 vaccine adjuvanted with ALHYDROGEL® (Brenntag Biosector). Three days before fusion, mice were boosted an additional time with the same formulation and splenocytes were isolated then fused to SP2/0-Ag14 myeloma cells in the presence of PEG 1500 (Roche Diagnostics GmbH, Germany). Fused cells were grown in RPMI 1640 medium supplemented with 10% Fetal bovine serum, 10% BM Condimed H1 (Roche Diagnostics GmbH, Germany), 2 mM L-glutamine, and 24 μM beta-mercaptoethanol and 1×HAT supplement (Invitrogen, Carlsbad, Calif.). Hybrids secreting SHe-specific antibodies were identified by SHe peptide ELISA screening and monoclonal antibodies producing hybrids were obtained after two rounds of sub-cloning by limiting dilution procedure. Monoclonal antibodies were purified on a protein A-Sepharose column (electrical engineering biosciences).

The resulting hybridomas were deposited under the Budapest treaty at BCCM (BCCM/LMBP: Technologiepark 927, 9052 Zwijnaarde, Belgium) under deposit numbers LMBP 7795CB for 3G8 on 8 Nov. 2010 and LMBP 7796CB for 3D11 on 10 Nov. 2010, respectively.

Example 1

Design, Expression and Purification of Flag-COMPcc-SHe

The SH protein is expressed at the surface of RSV virions and the plasma membrane of RSV-infected cells as a pentamer. The pentameric organization of SH is organized by the SH transmembrane domain, which oligomerizes as a coiled coil of five parallel alpha-helices. In order to present the C-terminal SH ectodomain (SHe) of RSV A as a pentamer that mimics its natural conformation, SHe was genetically fused to the short pentameric coiled coil domain of the rat cartilage oligomeric matrix protein (COMPcc), which is also composed of five parallel alpha-helices (Malashkevich et al., 1996; FIG. 1). A Flag-tag was fused to the N-terminus of COMP, rendering Flag-COMPcc-SHe. Flag-COMPcc-SHe was cloned in a pLT-32 (Mertens et al., 1995)_expression vector, expressed in *E. coli* and purified. Gel filtration analysis revealed that Flag-COMPcc-SHe eluted as a 55-60 kDa complex, indicating that the 11 kDa Flag-COMPcc-SHe proteins do indeed oligomerize into pentamers (FIG. 2).

Example 2

Flag-COMPcc-SHe Vaccination Induces SHe-Specific Antibodies and Protection Against RSV Infections To test if vaccination with Flag-COMPcc-SHe could evoke protection against RSV infection, we used a BALB/c mouse RSV infection model. BALB/c mice were immunized three times intranasally with 25 μg of Flag-COMPcc-SHe in combination with 1 μg *E. coli* heat-labile enterotoxin LTR192G adjuvant. PBS and the Influenza A M2 ectodomain fused to a tetrameric GNC4 scaffold (M2e-tGNC4) (De Filette et al., 2008) were used as negative controls. Immunizations were performed every fortnight. A single RSV infection ($5\times10^5$ PFU) was used as positive control. Between the first and the second week after each immunization, blood was collected to investigate the induction of SHe-specific IgG antibodies. The presence of SHe-specific antibodies was first tested by SHe peptide ELISA. M2e peptide ELISA was used as negative control. FIG. 3 demonstrates that SHe peptide-specific IgG antibodies are induced and boosted after, respectively, the second and third immunization with Flag-COMPcc-SHe. Three successive Flag-COMPcc-SHe/LTR192G immunizations resulted in high levels of IgG2a SHe-specific antibodies but only low levels of IgG1 SHe-specific antibodies, indicating a Th1-oriented/driven immune response. No SHe-specific IgG antibodies could be detected in PBS or M2e-tGCN4/LTR192G vaccinated mice (FIG. 3, Panels A, B and C). As expected, no M2e-specific antibodies could be detected in the sera of Flag-COMPcc-SHe/LTR192G or PBS vaccinated mice data. Mice that were immunized with M2e-tGCN4 accumulated a high titer of M2e-specific IgG2a antibodies, in accordance with previous results (De Filette et al., 2008).

Figure 4:
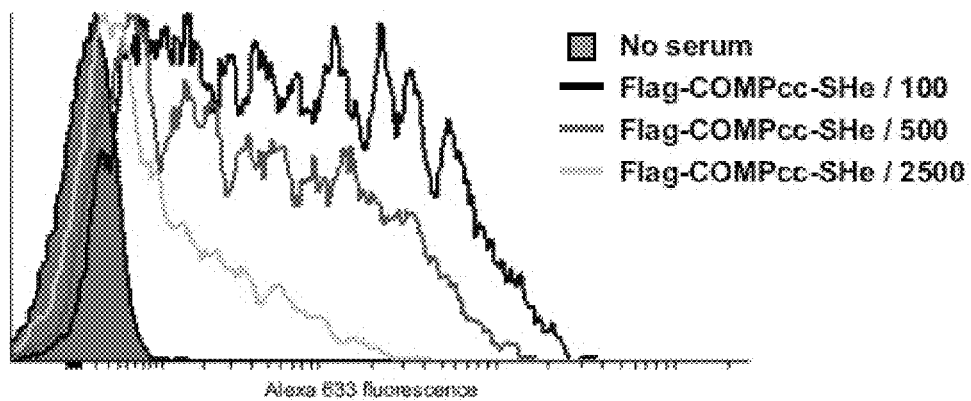
Figure 4:
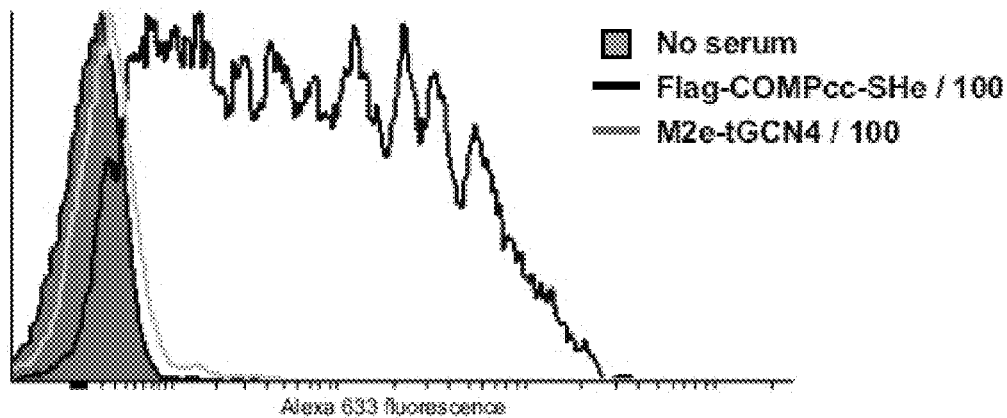
Figure 4:
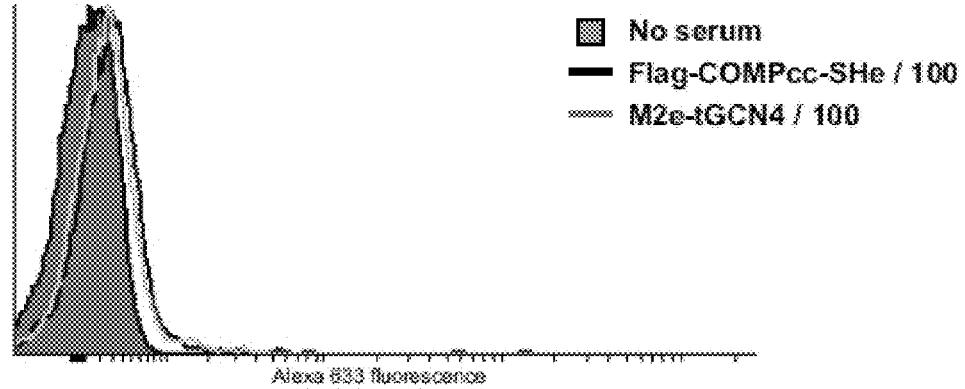

Next, we investigated if SHe-specific antibodies present in the Flag-COMPcc-SHe immune serum could bind to cells expressing the RSV-SH protein at their surface by flow cytometry. HEK-293T cells were transfected with a GFP expression vector, in combination with either a SH expression vector (pCAGGS-Etag-SH) or a Luciferase expression vector (pCAGGS-Luc) as negative control. Twenty-four hours after transfection, the cells were detached, stained with different dilutions of Flag-COMPcc-SHe or M2e-tGCN4 immune serum and analyzed by flow cytometry. FIG. 4 illustrates that, in contrast to M2e-tGCN4 immune serum, serum from Flag-COMPcc-SHe-vaccinated mice specifically binds SH protein expressed at the surface of living cells.

Figure 5:
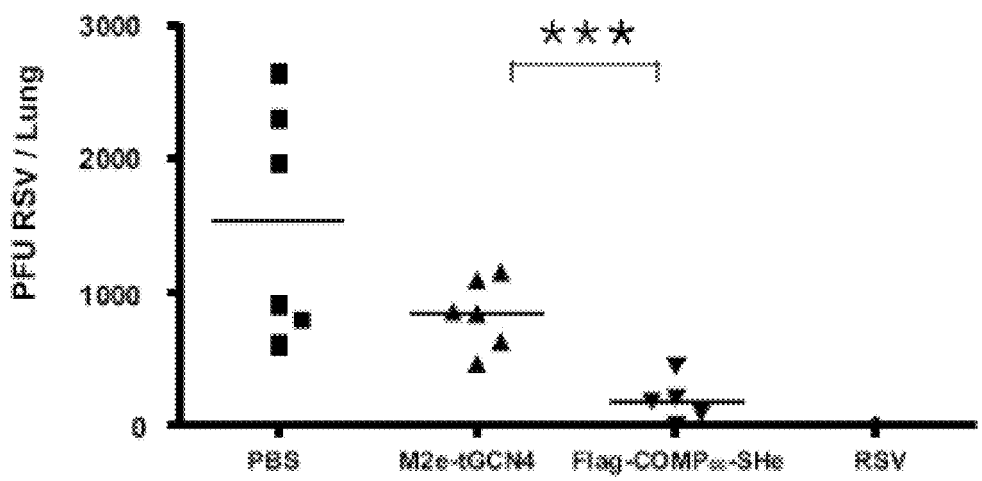

To test if Flag-COMPcc-SHe/LTR192G vaccination can elicit protection against RSV infection, the mice were challenged with $1\times10^6$ PFU RSV A2 nine weeks after the last immunization. Four days after infection, the mice were sacrificed to determine the viral lung titer by plaque assay. FIG. 5 illustrates that compared to PBS- and M2e-tGCN4-vaccinated mice, vaccination with Flag-COMPcc-SHe lowered RSV replication. No virus was detected in the mouse that was infected with living RSV before challenge.

Figure 6:
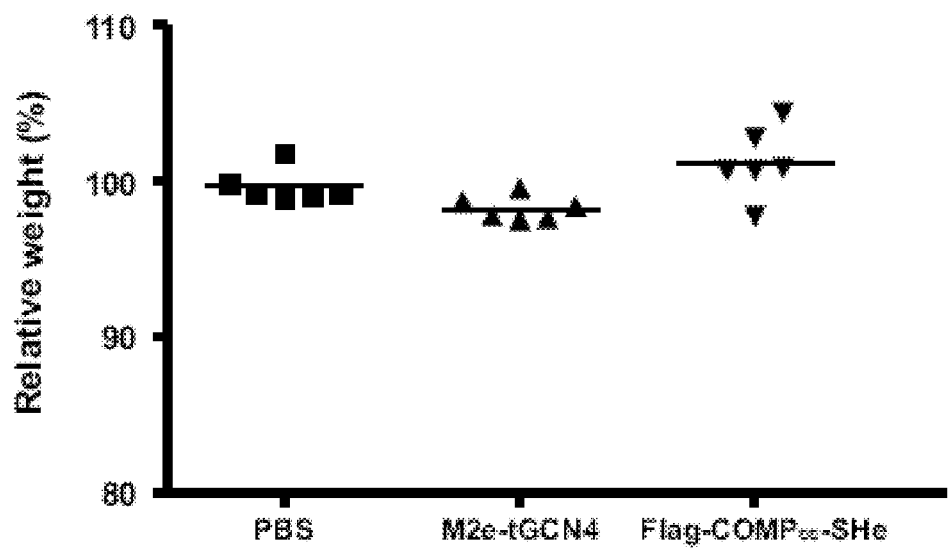

Vaccination with formalin-inactivated virus or the RSV G protein can induce enhancement of disease upon infection, resulting in significant morbidity, by the induction of an unbalanced Th2 immune response (Prince et al., 1986). To test if Flag-COMPcc-SHe vaccination might also induce enhancement of disease, we monitored the body weight before and after RSV challenge (FIG. 6). No weight loss was observed in any of the mouse groups after RSV challenge. This strongly suggests that Flag-COMPcc-SHe vaccination does not result in enhancement of disease upon RSV infection.

Example 3

Design, Construction and Purification of mHBc-SHe

The Hepatitis B virus core protein (HBc) virus-like particle (VLP) can present antigens as a dense array. In this way, HBc-VLPs can induce a strong humoral immune response toward the presented antigen (Boisgerault et al., 2002). Therefore, as an alternative to presenting SHe as a pentamer, the SH ectodomain was presented in the immunodominant region loop of mHBc-VLPs. HBc-SHe-VLPs were obtained by chemical linkage of SHe peptides to mHBc, a mutant of HBc in which a lysine was introduced in the top of the HBc immunodominant region (De Filette et al., 2005). To enable chemical linking, a cysteine residue was added to the N-terminus of SHe. In addition, the cysteine residue, present at position 4 of the SHe peptide, was replaced by a serine residue. This peptide was called SHe-CC4S. After purification of the mHBc-SHe-VLPs, by size exclusion chromatography, the degree of cross-linking was examined by SDS PAGE. FIG. 7 illustrates that approximately 50% of the HBc proteins is chemically linked to a SHe-CC4S peptide. The slower migrating bands likely represent mHBc monomers to which two or three SHe(cc4s) peptides were linked. To test if SHeCC4S-linked mHBc proteins still assemble into VLPs of the expected size (30-34 nm), Dynamic Light Scattering analyses was performed on the generated mHBc-SHe particles and the 1604 M2e-HBc VLP as fully functional reference. FIG. 8 illustrates that the size distribution of mHBc-SHe-CC4S overlaps with that of the 1604 M2e-HBc control, with a maximum at 30 nm, which corresponds with the reported size of HBc VLPs (Clarke et al., 1987).

Example 4

Design, Construction and Purification of SHe-tGCN4-Flag

Next to presenting the SHe peptide at the surface of mHBc VLPs, SHe was also fused to tGCN4, which is known to induce a strong humoral response toward fused peptides (Ref marina GCN4). SHe and a Flag-tag were genetically linked to, respectively, the 5'-end and the –3' end of the tGCN4 coding sequence and cloned into a PLT32 expression vector. After expression in *E. coli*, recombinant SHe-tGCN4-Flag was purified by anion exchange, hydrophobic interaction and gel filtration chromatography (FIG. 9).

Example 5 mHBc-SHe(CC4S) and SHe-tGCN4 Vaccination Induces SHe-Specific Antibodies and Protection Against RSV Infections To test if vaccination with mHBc-SHe(CC4S) and SHe-tGCN4 can evoke protection against RSV infections, Balb/c mice were vaccinated three times intranasally with 10 mHBc-SHe(CC4S) and SHe-tGCN4 in combination with 1 μg LTR192G adjuvant. PBS and empty mHBc, the latter in combination with 1 μg LTR192G, were used as negative controls. Immunizations were performed every three weeks. A single RSV infection ($5\times10^5$ PFU) was used as positive control. Between the second and the third week after each immunization, blood was collected to investigate the induction of SHe-specific IgG antibodies. The presence of SHe-specific antibodies was tested by SHe peptide ELISA. FIG. 10, Panel A, demonstrates that SHe peptide-specific IgG antibodies are induced and boosted after, respectively, the second and third immunization with mHBc-SHe(CC4S) and SHe-tGCN4. Three successive Flag-COMPcc-SHe/LTR192G immunizations resulted in high levels of IgG2a SHe-specific antibodies and somewhat lower levels of IgG1 SHe-specific antibodies, indicating a Th1-oriented/driven immune response (FIG. 10, Panel B).

To test if vaccination with mHBc-SHe(CC4S) or SHe-tGCN4 can hamper RSV infection, the mice were challenged with $5\times10^6$ PFU RSV A2 three weeks after the last boost immunization. Three days after challenge, the mice were sacrificed to determine the pulmonary RSV A2 levels by QPCR. FIG. 11 shows that all mice that were vaccinated with mHBc-SHe(CC4S) or SHe-tGCN4 or mice that were infected beforehand with RSV, have lower pulmonary levels of genomic RSV RNA than mice that were vaccinated with mHBc. These data confirm our previous observation that mucosal SHe-based vaccination can partially protect mice against RSV replication. Remarkably, all mice that were vaccinated with an empty mHBc in combination with the LTR192G adjuvant, displayed lower levels of RSV than mice that were immunized with PBS without LTR192G adjuvant. This might be explained by the effect of LTR192G on the mouse innate immune system. The *E. coli* heat labile enterotoxin has been shown to provide generic protection against lung viral infections, including RSV, via innate imprinting (ref Williams and Hussel 2004). The effect of innate imprinting by LTR192G on lung viral replication appears to be transient as the impact of TLR192R on RSV replication is strongly reduced when viral infection occurs nine weeks after the last LTR192G administration. Again, none of the mice showed significant body weight loss, indicating that vaccination with SHe when presented by VLPs or tGCN4 is not inducing enhancement of disease upon challenge (FIG. 12).

Example 6

Production and Testing of SHe-Specific Monoclonal Antibodies

To investigate if SHe-specific antibodies that can interact with infected cells can provide protection against RSV infections, we developed RSV SHe-specific monoclonal antibodies based on SHe-TGCN4 immunized mice. One IgG1 (3D11) and one IgG2a (3G8) subtype hybridoma that produced antibodies that efficiently bound to SHe peptide in an ELISA were selected, subcloned and used for antibody production. The 3D11 and 3G8 were purified via protein A affinity chromatography and tested for binding efficacy to SHe via an ELISA. FIG. 13 shows that 3D11 and 3G8 can bind to coated SHe peptide and are, respectively, of the IgG1 and IgG2a subtype.

As antibodies can protect against viral infections via recognition and killing of infected cells by (ADCC) or CDC, we investigated if the SHe-specific mAbs 3D11 and 3G8 can recognize SH at the surface of cells. Therefore, Hek293T cells were transfected with an RSV SH expression vector or with a control Firefly luciferase vector (Schepens et al., 2005), both in combination with a GFP expression vector. Twenty-four hours after transfection, live cells were stained with different concentrations of the SHe-specific monoclonal antibodies (3D11 and 3G8) or isotype matched Influenza M2e-specific antibodies (14C2 IgG1 and a IG2a M2e-specific mAb). Polyclonal serum from Flag-COMPcc-SHe-immunized mice was used as positive control. FIG. 14 demonstrates that Flag-COMPcc-SHe polyclonal serum, along with both 3D11 and 3G8 mAbs, can readily bind to SH-expressing cells but not to control cells. In contrast, the IgG1 and IgG2a Influenza M2e-specific antibodies could not bind to SH-expressing cells. These data clearly demonstrate that both 3D11 and 3G8 can recognize the ectodomain of SH expressed at the surface of cells.

During infection, the RSV SH protein is mainly expressed at the ER, golgi and cell membrane. In order to more directly investigate whether the RSV SH-specific antibodies can recognize infected cells via SH expressed at the surface of these cells, we performed immunostaining of RSV-infected and mock-infected cells. Human A594 lung epithelial cells were either infected with 0.05 MOI of RSV or mock infected. Twenty-four hours after infection, the cells were fixed and stained with the SHe-specific mAbs 3D11 or 3G8 in combination with polyclonal anti-RSV immune serum. FIG. 15 illustrates that the SHe-specific mABs 3D11 and 3G8 can readily recognize SH at the cell membrane and near the nucleus (likely corresponding to ER and Golgi) of infected cells. This indicates that SHe mAbs protect against RSV infection by recognizing RSV-infected cells. In this way, the herein-described SHe mAbs 3D11 and 3G8 can be used as prophylactic or therapeutic treatment.

Example 7

Passive Immunization Using SHe-Specific mAB 3G8 Reduces RSV Replication

To test if SHe-specific antibodies can reduce RSV replication in vivo, mice were passively immunized with SHe-specific monoclonal antibodies. SHe-specific 3G8 monoclonal antibodies, isotype control antibodies or PBS were intranasally administered to mice one day before and one day after RSV Challenge. Three days after RSV challenge, blood was collected to test for the presence of mAbs in the serum of the treated mice. Four days after RSV challenge, the mice were sacrificed to determine the viral titer in the lungs. Peptide ELISA demonstrated the presence of low concentrations of SHe-specific and isotype control antibodies in the serum of mice treated with the respective antibodies (data not shown). FIG. 16 illustrates that mice that received SHe-specific monoclonal antibodies have reduced lung RSV titers as compared with mice that were treated with PBS or isotype control monoclonal antibodies. These data suggest that intranasal administration of SHe-specific antibodies can reduce RSV infection in mice.

Example 8

Construction of SHe-KLH

To test if SHe-based vaccines can also protect against RSV infections when this vaccine is administered via an alternative route with an alternative adjuvant and with a different carrier, the vaccine was tested intraperitoneally, with keyhole limpet hemocyanin (KLH) as a carrier. Maleimide-activated KLH (Pierce) was chemically linked to the peptide (CGGGS NKLSEYNVFHNKTFELPRARVNT (SEQ ID NO:50); the sequence corresponding to the RSV A SH ectodomain (SHe) is underlined) corresponding to the RSV A SH ectodomain. To promote directional chemical linking, a CysGlyGlyGly-Ser (SEQ ID NO:55) linker was added to the N-terminus of the RSV A SHe peptide. In addition, the cysteine residue present in the natural RSV A SHe was substituted by a serine residue. Chemical linkage was performed according to the manufacturer's instructions (Pierce). Cross-linked KLH-SHe proteins were isolated by size exclusion chromatography.

Example 9

Intraperitoneal Vaccination with KLH-SHe Reduces RSV Replication in Mice

To test if intraperitoneal (I.P.) vaccination with a SHe-based vaccine can evoke protection against RSV infections, Balb/c mice (six mice per group) were vaccinated three times intraperitoneally with 20 μg of KLH-SHe or KLH, each in combination with 50 μl of Freund's Incomplete Adjuvant (Millipore). PBS vaccination without adjuvant was used as an additional negative control. Between the second and third week after vaccination, blood was collected to determine the induction of SHe-specific IgG antibodies. The presence of SHe-specific antibodies was determined and quantified by SHe peptide ELISA. FIG. 17 (Panels A and B) demonstrate that three successive vaccinations with KLH-SHe induces high levels of SHe-specific IgG antibodies of both the IgG1 and IgG2a subtype. No SHe-specific IgG antibodies could be detected in sera from PBS- or KLH-vaccinated mice. In addition, flow cytometric analysis revealed that serum derived from mice that had been vaccinated intraperitoneally with KLH-SHe can specifically bind to HEK293T cells that express the RSV SH protein at their surface, whereas preimmune serum did not.

To test whether intraperitoneal KLH-SHe vaccination can reduce RSV infection, the vaccinated mice were infected with 1×10$^6$ PFU of RSV A2 four weeks after the last vaccination. Five days after challenge, the mice were sacrificed to determine the pulmonary RSV A2 titer by plaque assay. FIG. 17, Panel D, illustrates that significantly less virus could be detected in the lungs of SHe-KLH-vaccinated than in the lungs of KLH-vaccinated mice (P>0.005, Mann-Whitney U test). The observation that among KLH-SHe-vaccinated mice, higher titers of serum SHe-specific IgG antibodies strongly correlated ($R^2$=0.95) with lower levels of pulmonary RSV at day 5 post-infection, suggests that reduction of RSV replication by KLH-SHe vaccination is mediated by SHe-specific antibodies (FIG. 17, Panel E). The body weight of all mice was monitored at the day of infection and the day of sacrifice. FIG. 17, Panel C, illustrates that mice that were vaccinated with KLH-SHe gained significantly more weight than mice that were vaccinated with KLH (P>0.005, Mann-Whitney U test). These data demonstrate that intraperitoneal vaccination with a SHe-based vaccine can reduce RSV replication without inducing morbidity. In addition, these data illustrate that next to mHBc, tGCN4 and COMPcc, KLH can also be used as a protein carrier for SHe peptide-based vaccines. Moreover, these data illustrate that next to TITER-MAX®, also Freunds' Incomplete Adjuvant can also be used as an appropriate adjuvant to induce SHe-specific immunity.

Example 10

Intranasal Vaccination with KLH-SHe Reduces RSV Replication in Mice

To test if intranasal vaccination with KLH-SHe can evoke protection against RSV infections, Balb/c mice (six mice per group) were vaccinated three times intranasally with 20 μg of KLH-SHe or KLH, each in combination with 1 μg of LTR192G adjuvant. PBS vaccination without adjuvant was used as an additional negative control. Between the second and third week after vaccination, blood was collected to investigate the induction of SHe-specific IgG antibodies. The presence of SHe-specific antibodies was tested by SHe peptide ELISA. FIG. 18 (Panels A and B) demonstrate that three successive vaccinations with KLH-SHe induce SHe-specific IgG antibodies of both the IgG1 and IgG2a subtype. No SHe-specific IgG antibodies could be detected in sera from PBS- or KLH-vaccinated mice. In addition, flow cytometric analysis revealed that serum derived from mice that were vaccinated intranasally with KLH-SHe serum, but not pre-immune serum, can specifically bind to HEK293T cells that express the RSV SH protein at their surface.

To test whether intraperitoneal KLH-SHe vaccination can reduce RSV infection, the vaccinated mice were infected with $1\times10^6$ PFU of RSV A2 nine weeks after the last vaccination. Five days after challenge, the mice were sacrificed to collect BAL (Broncho Alveolar Lavage) fluid (3 ml). The RSV A2 titer in the collected BAL fluids was determined by plaque assay. FIG. 18, Panel E, illustrates that significantly less virus could be detected in the lungs of KLH-SHe-vaccinated mice than in the lungs of KLH-vaccinated mice ($P>0.05$, Mann-Whitney U test). The presence of SHe-specific IgA and IgG antibodies in the collected BAL fluids was analyzed by SHe peptide ELISA. This analysis revealed that in contrast to PBS- and KLH-vaccinated mice, the BAL fluids of mice vaccinated with KLH-SHe contained both IgG and IgA SHe-specific antibodies (FIG. 18, Panels C and D). The levels of IgG SHe-specific antibodies present in the BAL fluid of KLH-SHe-vaccinated mice correlated with the levels of IgG SHe-specific antibodies in the serum of the respective mice. The observation that among KLH-SHe-vaccinated mice, higher titers of SHe-specific IgG antibodies present in the BAL fluid strongly correlate ($R^2=0.97$) with lower levels of pulmonary RSV titers on day 5 post-infection, suggests that reduction of RSV replication by KLH-SHe vaccination is mediated by SHe-specific antibodies (FIG. 18, Panel F). These data demonstrate that intranasal vaccination with a SHe-based vaccine can reduce RSV replication without inducing morbidity. In addition, these data confirm that next to mHBc, tGCN4 and COMPcc, KLH can also be used as a protein carrier for SHe peptide-based vaccines.

Example 11

Passive Transfer of KLH-SHe Immune Serum Protects Against RSV Infection in Mice To further investigate if the reduction in RSV replication in mice that have been vaccinated with a SHe-based vaccine can be mediated by RSV SHe-specific antibodies, passive transfer experiments were performed. Balb/c mice were vaccinated intraperitoneally with 20 μg of either KLH-SHe or KLH, both in combination with 75 μl of Freund's Incomplete Adjuvant. As an additional negative control, mice were vaccinated with PBS without adjuvant. SHe peptide ELISA illustrated that the sera of all mice that had been vaccinated with KLH-SHe contains high levels of SHe-specific IgG antibodies. After final bleeding, the sera of the mice of each group were pooled and heat inactivated at 56° C. for 30 minutes. To test if KLH-SHe sera can protect against RSV infections, 40 μl of KLH or KLH-SHe sera were administered to mice intranasally one day before (day −1) and one day after (day 1) RSV challenge ($2\times10^5$ PFU) (day 0). Mice that were treated with PBS were included as additional controls. The weight of all mice was monitored daily (FIG. 19, Panel C). Five days post-infection, the mice were sacrificed to prepare lung homogenates. Plaque assay analysis demonstrated that the lung homogenates of mice that had been treated with KLH-SHe serum contained about 40 times less (ratio of means of viral titers) replicating virus than the lung homogenates originating from mice treated with KLH serum (FIG. 19, Panel B). The observation that the pulmonary RSV titer of mice that were treated with KLH serum did not differ from the pulmonary RSV titer of mice that were treated with PBS, illustrates that administration of control serum does not impact pulmonary RSV replication in mice.

Example 12

Construction of mHBc-SHeB

Although highly conserved within their subtype, the SHe amino acid sequences of RSV B viruses differs from that of the RSV A subtype viruses. Therefore, to protect against RSV B viruses, a SHe-based vaccine most likely needs to include the RSV B SHe amino acid sequence.

A RSV B SHe vaccine was constructed by chemically linking the consensus RSV B SHe peptide (SHeB: CGGGSNKLSEHKTFSNKTLEQGQMYQINT (SEQ ID NO:51) to the mHBc virus-like particles. To promote chemical linking, a CysGlyGlyGlySer (SEQ ID NO:55) linker was added to the N-terminus of the RSV B SHe peptide. In addition, the cysteine residue present in the natural RSV B SHe was substituted by a serine residue. The immunogen resulting from chemical linkage of the RSV B SHe peptide to mHBc was named mHBc-SHeB. After purification of the mHBc-SHeB VLPs by size exclusion chromatography, the degree of cross-linking was analyzed by SDS-PAGE gel electrophoresis and Coomassie staining. FIG. 20 illustrates that more than half of the HBc monomers are cross-linked to at least one SHe peptide.

Example 13

Figure 21A:
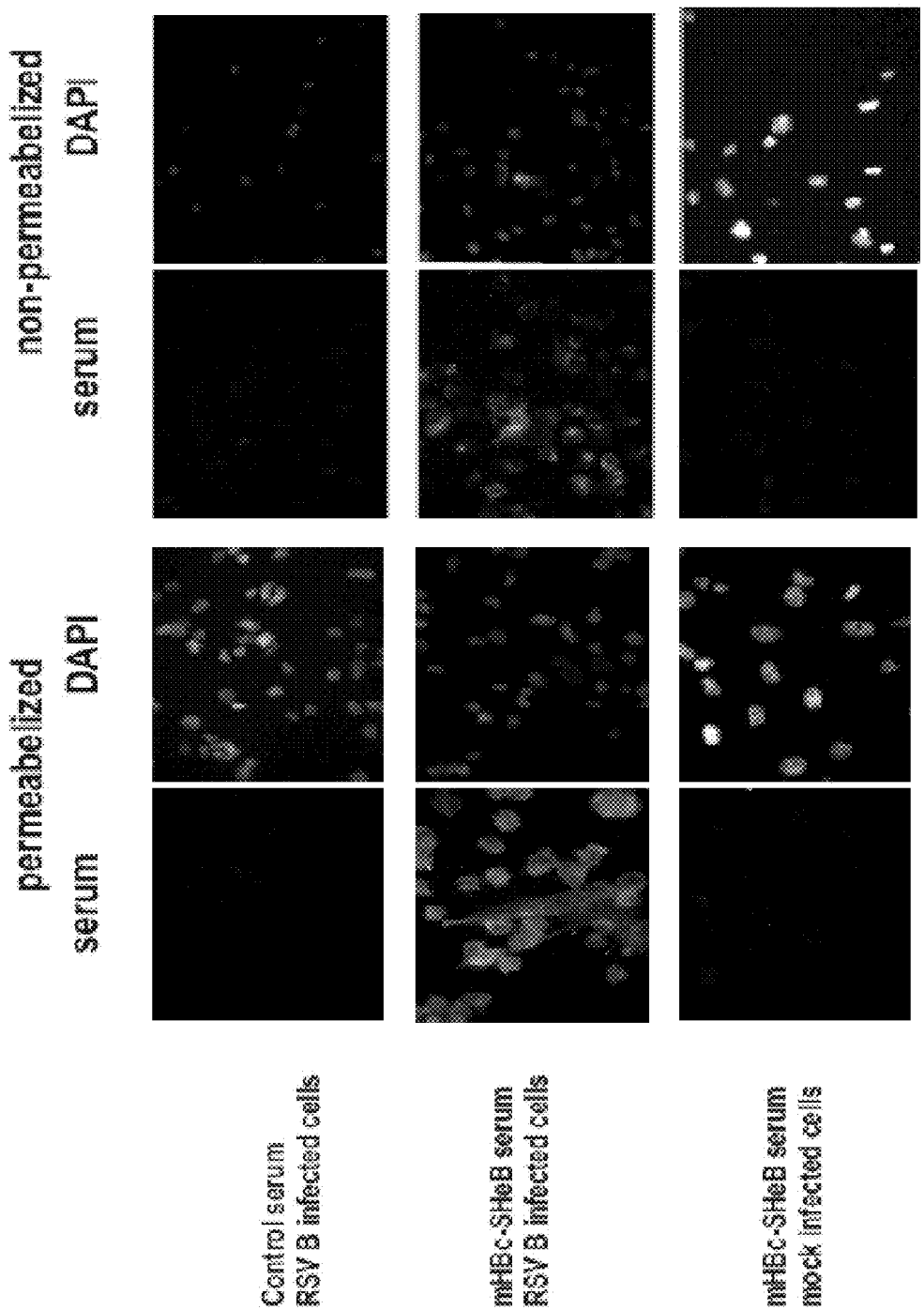
Figure 21B:
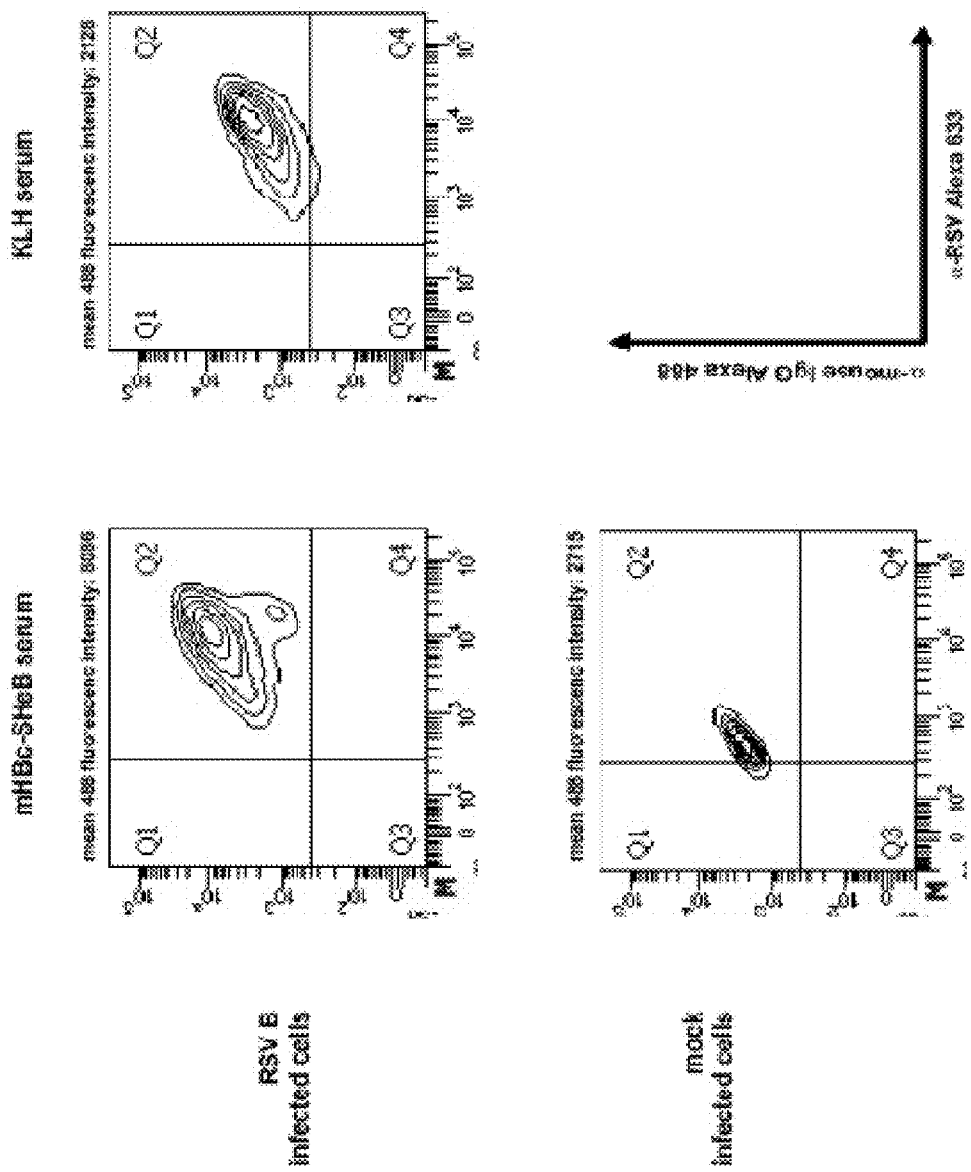

Immunization of Mice with mHBc-SHeB Induces SHeB-Specific Abs that Bind to the Surface of RSV B-Infected Cells To test whether mHBc-SHeB VLPs were immunogenic, one BALB/c mouse was immunized three times subcutaneously with 20 µg of mHBc-SHeB combined with 50 TITER-MAX® (Sigma). The three immunizations were performed with two-week intervals. Bleedings were performed one day before each immunization and two weeks after the final immunization. To test whether mHBc-SHeB immune serum can recognize RSV B SH proteins expressed on the surface of infected cells, Vero cells were either mock infected or infected with a clinical isolate of RSV B virus (kindly provided by Dr. Marc van Ranst, University of Leuven, Leuven, Belgium). Seventy-two hours after infection, the cells were fixed and either permeabilized using 0.2% TRITON® X-100 or not permeabilized. The cells were then stained with either mHBc-SHeB immune serum (1/100 dilution) or control immune serum (1/100 dilution) derived from BALB/c mice that had been vaccinated with KLH (KLH serum) in combination with Freund's Incomplete Adjuvant. The samples were analyzed by immunofluorescent microscopy or flow cytometry. FIG. 21, Panels A and B, illustrate that mHBc-SHeB immune serum can bind to both permeabilized and non-permeabilized RSV B-infected cells but not to non-infected cells. In contrast, control immune serum did not bind to RSV B-infected cells. This demonstrates that vaccination of mice with mHBc-SHeB induces serum antibodies that can recognize RSV B-infected cells, most likely by binding to the RSV B SH protein that is expressed at the surface of RSV B-infected cells.

Example 14 mHBc-SHeB Immunization Reduces RSV Replication in Mice

Figure 22:
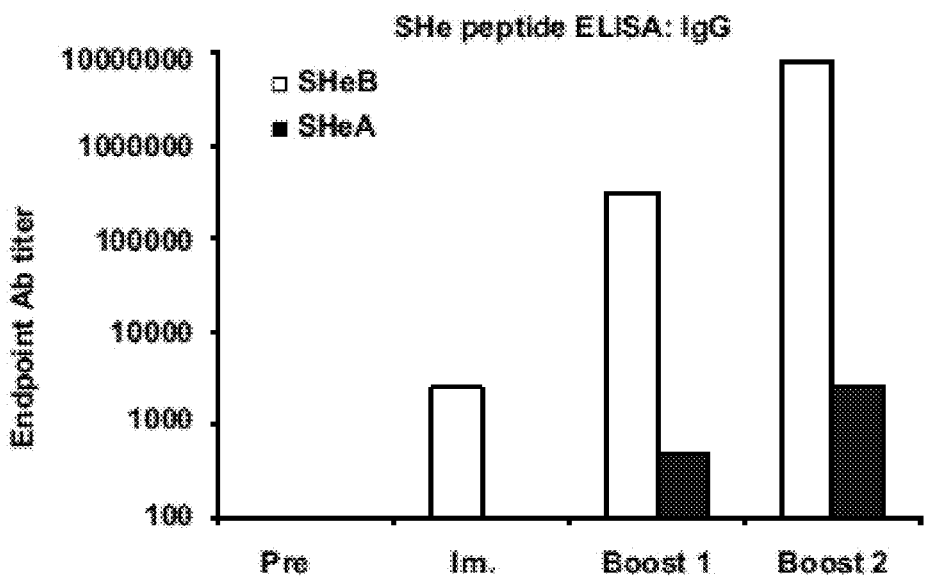
Figure 22:
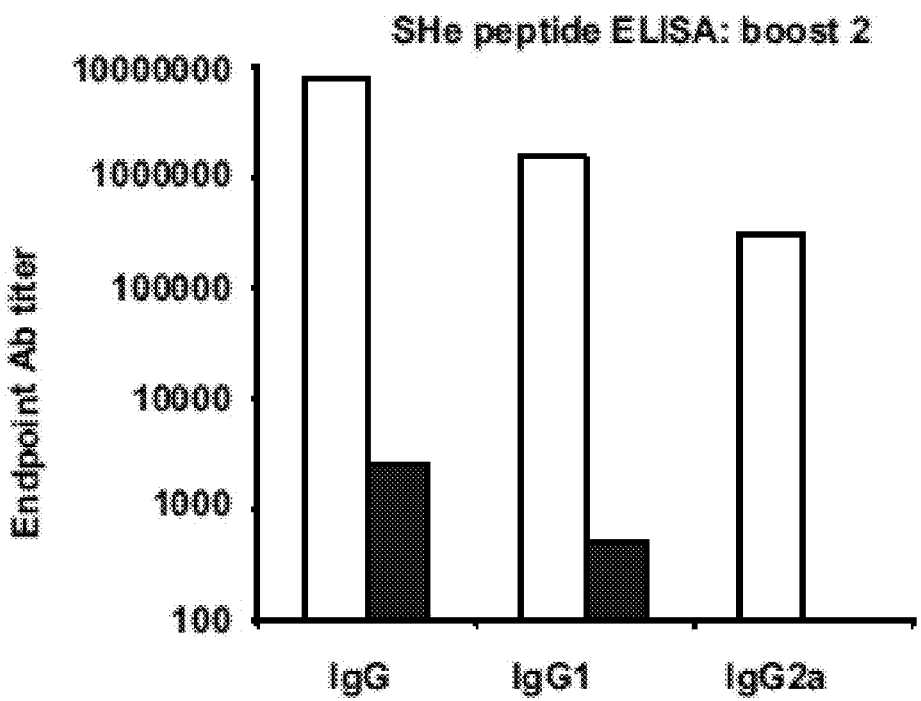
Figure 22:
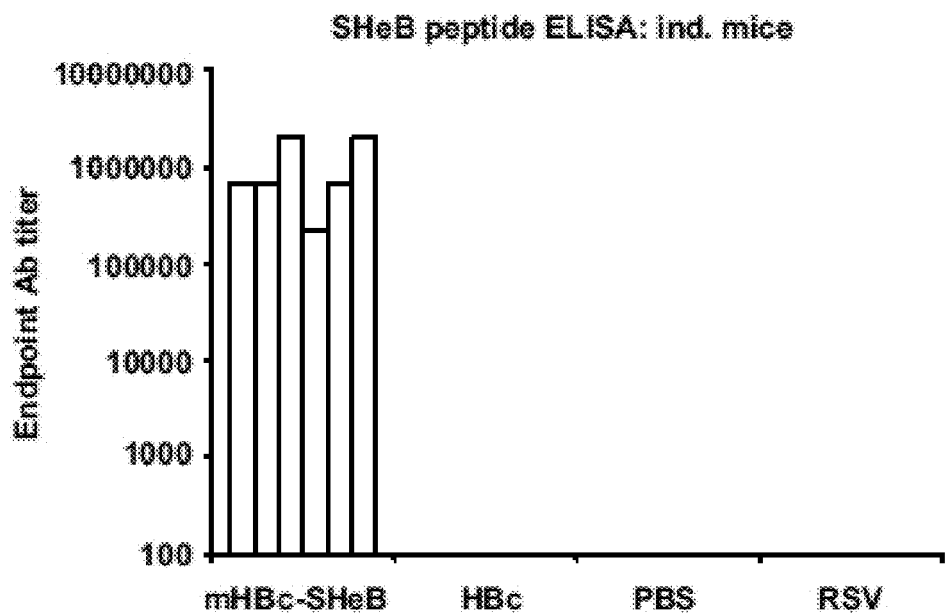
Figure 22:
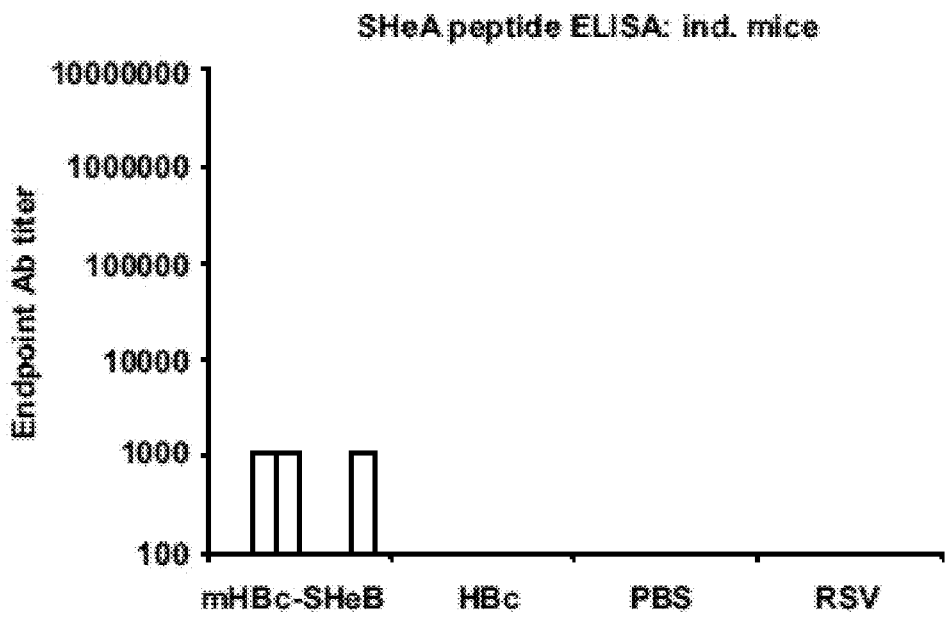
Figure 22:
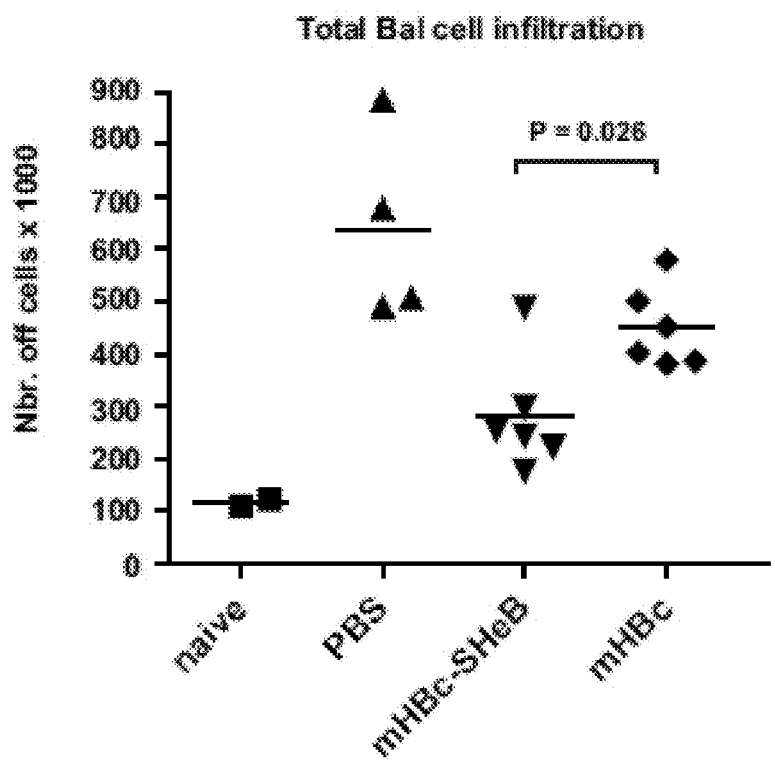
Figure 22:
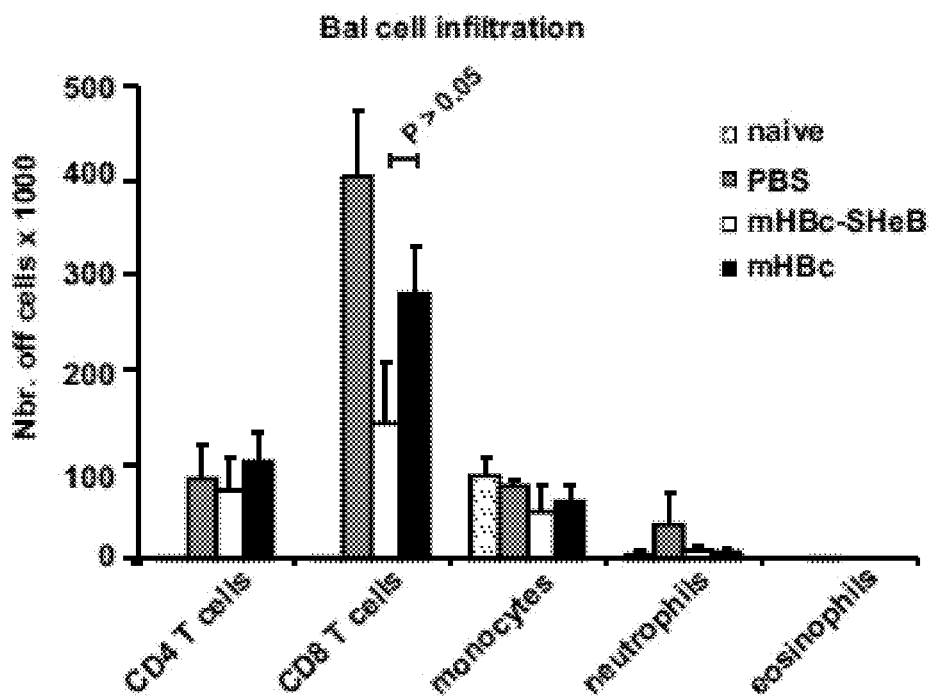

To test whether mHBc-SHeB vaccination can protect mice from RSV B infection, two groups of six mice were immunized with mHBc or mHBc-SHeB VLPs, adjuvanted with 50 µl of Freund's Incomplete Adjuvant. As additional controls, six mice were vaccinated with PBS. Vaccinations were performed intraperitoneally, three times with three-week intervals. Bleedings were performed two weeks after each immunization. The induction of SHe-specific antibodies was determined by peptide ELISA using SHeA or SHeB as coating peptides. This analysis demonstrated that in all mice, three successive mHBc-SHeB immunizations induced high titers of RSV B SHe-specific IgG antibodies of both IgG1 and IgG2a subtype (FIG. 22, Panels A-C). mHBc-SHeB immune serum also bound to the SHeA peptide but to a much lower extent (FIG. 22, Panels A, B and D).

Previous experiments in our and other laboratories have illustrated that no or very little replicating virus can be rescued from RSV B-infected mice. Nevertheless, we could observe that infections with clinical RSV β isolates induce pulmonary inflammation and weight loss in BALB/c mice (data not shown). Therefore, we tested whether mHBc-SHeB vaccination could protect mice from RSV B-induced pulmonary inflammation. Six days after intranasal challenge of mice with $2 \times 10^6$ PFU of an RSV B clinical isolate, Broncho Alveolar Lavage (BAL) was performed. Mock-infected mice were used as negative control for analysis of BAL cell infiltration. The BAL fluid was analyzed for immune cell infiltration by flow cytometry as described in Bogaert et al., 2011. FIG. 22, Panels E and F, show that RSV B infection results in pulmonary infiltration of immune cells, especially $CD8^+$ T lymphocytes, which are known to be responsible for RSV-induced morbidity in mice. However, compared to PBS- or mHBc-vaccinated mice, mHBc-SHeB-vaccinated mice displayed significantly lower pulmonary cell infiltration. These data demonstrate that mHBc-SHeB vaccination reduces RSV-related immune pathology.

Example 15

Design, Expression and Purification of the $LPP_{(5)}$-SHe Protein

Figure 23:
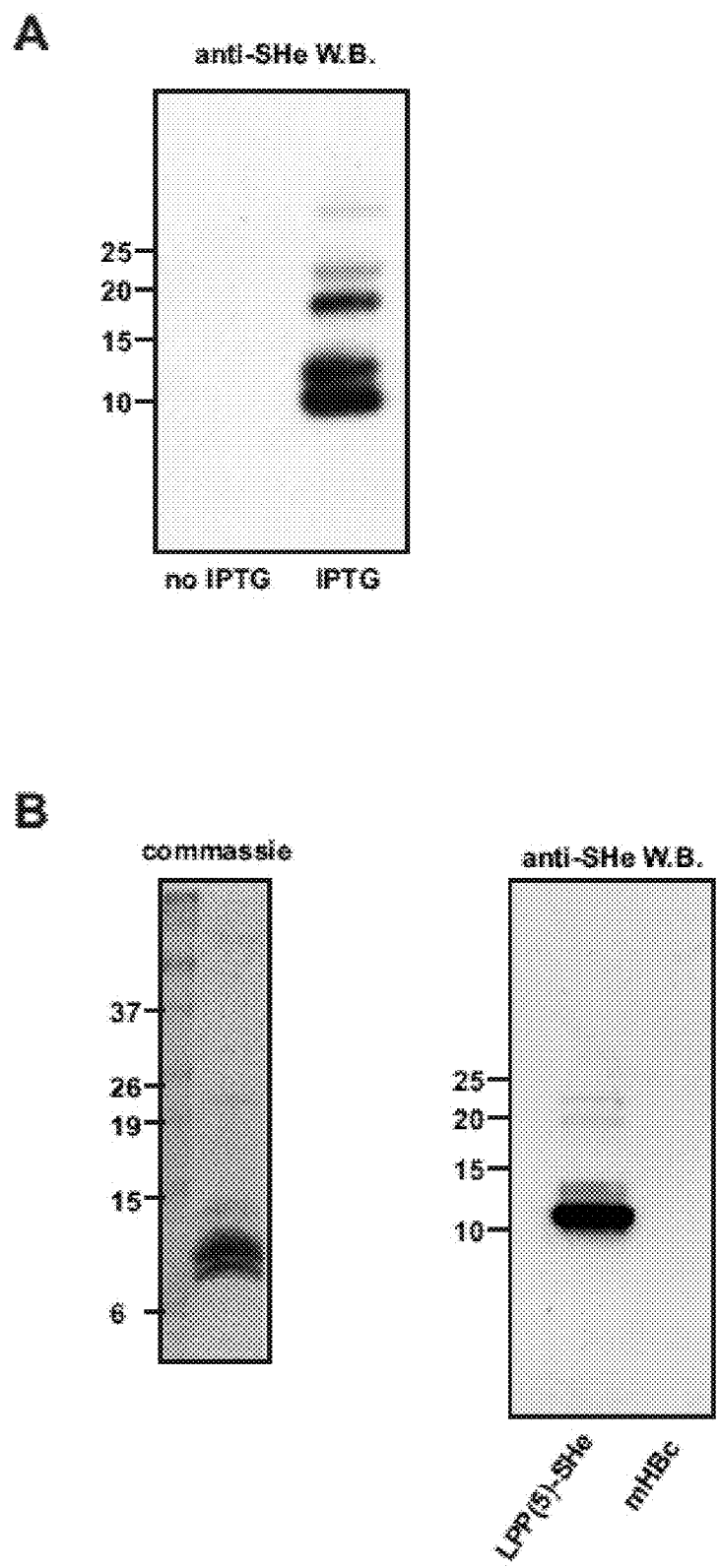

As an alternative protein scaffold to present SHe as a pentamer, we used the pentameric tryptophan-zipper described by Liu et. al. ($LPP_{(5)}$), which is derived from the *E. coli* LPP-56 lipoprotein (Liu et al., 2004). The coding sequence of the $LPP_{(5)}$ tryptophan-zipper was genetically fused to the SHe coding sequence and cloned into an *E. coli* expression vector (pLH36) containing a hexahistidine peptide and a caspase cleavage site as described by Mertens et al., 1995. This expression plasmid was named pLH36-HisDEVD-LPP-SHe (SEQ ID NO:49). Expression from this plasmid renders the chimeric $LPP_{(5)}$-SHe protein (SEQ ID NO:52) (M HHHHHHPGGS*DEVD*AKWDQWSSDW-QTWNAKWDQWSNDWNAWRSDWQAWK DDWAR-WNQRWDNWATGGN*KLCEYNVFHNKTFEL-PRARVNT* (SEQ ID NO:52), His-tag sequence is underlined, linkers are in italic, DEVD caspase cleavage site is in italic+underlined, pentameric LPP tryptophan-zipper is in bold and the RSV A SH ectodomain is in bold+italic). After induction of expression in *E. coli*, the $LPP_{(5)}$-SHe protein was purified by subsequent Nickel affinity, anion-exchange and gel filtration chromatography. FIG. 23 demonstrates that the $LPP_{(5)}$-SHe protein can be recognized by SHe-specific 3G8 monoclonal antibodies, both in a crude cell extract (FIG. 23, Panel A) and as a purified protein (FIG. 23, Panel B).

Example 16

Cotton Rat Immunization

Figure 24:
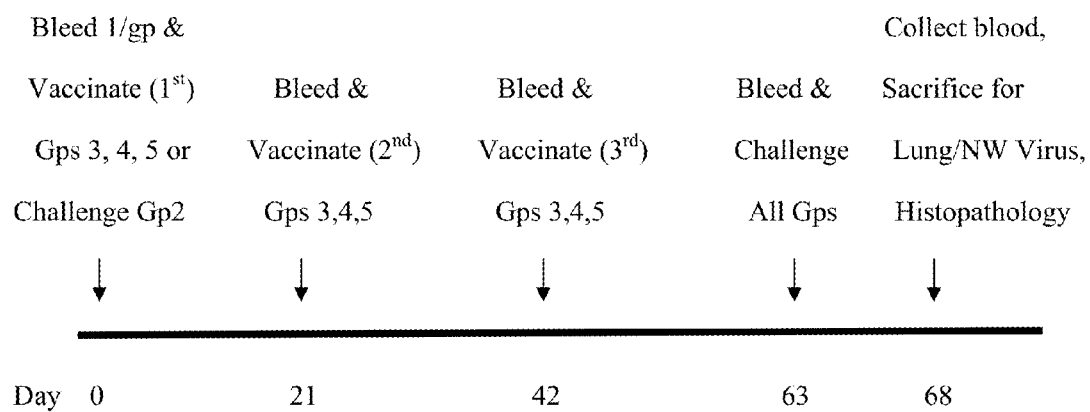

In order to prove the efficacy of the vaccine in an independent animal model, cotton rats are used. Cotton rats (*Sigmondon hispidus*) are susceptible to RSV infection (Prince et al., 1978). Five groups of six cotton rats each are used. Two groups of animals are immunized intraperitoneally (i.p.) with 100 µg of KLH (vehicle control) or 100 µg of KLH-SHe (i.e., a chemical conjugate of SHe peptide derived from RSV-A with KLH as a carrier). KLH and KLH-SHe vaccine antigens are formulated with Freund's Incomplete Adjuvant and used to immunize cotton rats on days 0, 21, and 42. A third group of animals is immunized intramuscularly with formalin-inactivated RSV (FI-RSV) in the presence of alum adjuvant. The latter group serves as a positive control for the induction of vaccine-enhanced disease that becomes apparent upon subsequent challenge with RSV. A fourth group is infected with $2.04 \times 10^5$ plaque forming units per cotton rat of RSV-Tracy on day 0 and serves as positive control for protection against subsequent challenge. A fifth group of cotton rats remains untreated until the day of challenge and served as control for the challenge with RSV. The schedule of the vaccination is shown in FIG. 24.

Sera are collected before each immunization and on the day of challenge. On day 63, cotton rats are challenged intranasally with $2.04 \times 10^5$ plaque forming units of RSV-Tracy. The challenge virus is administered intranasally in a volume of 100 microliters while the animals are lightly anesthetized with isofluorane. On day 68, serum is collected and all animals are sacrificed to collect lungs for virus titration and histopathological analysis. Each lung is divided in two to perform histopathological analysis and virus titration. The left lungs are tied off and used for histopathological analysis. The lobes of the right lung are lavaged using 3 ml of Iscove's media with 15% glycerin. The lavage fluid is stored on ice until titration. In addition, nasal lavages are prepared with 2 ml (1 ml for each nare) in the same medium.

The viral load in the lung and nasal lavages is determined by plaque assay on HEp2 cells. Cells are infected for 90 minutes with a serial dilution of the lavage samples. After removal of the inoculum, the cells are overlaid with 2% methylcellulose in MEM-containing antibiotics. After six days of incubation at 37° C. in a $CO_2$-incubator, plaques are counterstained with 0.1% crystal violet/10% formalin solution and left at room temperature for 24 hours.

For histopathological analysis, the left lung is perfused with 10% neutral buffered formalin. Fixed lung tissue is subsequently processed with a microtome to produce sections that are stained with hematoxilin and eosin and scored for the degree of histopathological lesions.

Serum samples are assayed for the presence of anti-SHe- and anti-RSV-neutralizing antibodies by peptide ELISA and by a microneutralization assay. For peptide ELISA, plates are coated overnight at 37° C. with 2 μg of SHe-peptide in 50 μl of 0.1 M carbonate buffer pH 9.6. After coating, plates are blocked with 3% (w/v) milk powder in PBS, followed by application of three-fold serial dilutions on cotton rat sera. Retained SHe-specific cotton rat IgG are detected using horseradish peroxidase conjugated secondary antibodies and tetramethylbenzidine substrate. The endpoint anti-SHe peptide IgG titer in the samples is defined as the highest dilution for which the absorbance is at least twice as high as that of the pre-immune serum.

Neutralizing antibody titers are determined for RSV-A and -B in 96-well microtiter plates with HEp2 cells. Serial dilutions of serum samples are mixed with a fixed amount of inoculum virus. The neutralizing antibody titer is defined as the serum dilution at which >50% reduction is cytopathic effect is observed. This cytopathic effect refers to the destruction of cells and is determined visually after the cells are fixed with 10% neutral buffered formalin and stained with crystal violet. The results show that the animals, vaccinated with KLH-SHe in Freund's Adjuvant develop neutralizing antibodies and are clearly protected, whereas the vehicle control shows no protection at all.

REFERENCES

Altschul S. F., T. L. Madden, A. A. Schäffer, J. Zhang, Z. Zhang, W. Miller, and D. J. Lipman (1997). Gapped BLAST and PSI-BLAST: a new generation of protein database search programs. *Nucleic Acids Res.* 25:3389-3402.

Beeler J. A. and K. van Wyke Coelingh (1989). Neutralization epitopes of the F glycoprotein of respiratory syncytial virus: effect of mutation upon fusion function. *J. Virol.* 63:2941-2950.

Bocchini Jr., J. A., H. H. Bernstein, J. S. Bradley, M. T. Brady, C. L. Byington, M. C. Fisher, M. P. Glode, M. A. Jackson, H. L. Keyserling, D. W. Kimberlin, W. A. Orenstein, G. E. Schutze, R. E. Willoughby, P. H. Dennehy, R. W. Frenck Jr., B. Bell, R. Bortolussi, R. D. Clover, M. A. Fischer, B. Gellin, R. L. Gorman, R. D. Pratt, L. Lee, J. S. Read, J. R. Starke, J. Swanson, C. J. Baker, S. S. Long, L. K. Pickering, E. O. Ledbetter, H. C. Meissner, L. G. Rubin, and J. Frantz (2009). From the American Academy of Pediatrics: Policy statements—Modified recommendations for use of palivizumab for prevention of respiratory syncytial virus infections. *Pediatrics* 124:1694-16701.

Boisgerault F., G. Moron, and C. Leclerc (2002). Virus-like particles: a new family of delivery systems. *Expert Rev. Vaccines* 1:101-109.

Bogaert P., T. Naessens, S. De Koker, B. Hennuy, J. Hacha, M. Smet, D. Cataldo, E. Di Valentin, J. Piette, K. G. Tournoy, and J. Grooten (2011). Inflammatory signatures for eosinophillic vs. neutrophillic allergic pulmonary inflammation reveal critical regulatory checkpoints. *Am. J. Physiol. Lung Cell Mol. Physiol.* 300: L679-690.

Clarke B. E., S. E. Newton, A. R. Carroll, M. J. Francis, G. Appleyard, A. D. Syred, et al. (1987). Improved immunogenicity of a peptide epitope after fusion to hepatitis B core protein. *Nature* 330:381-384.

De Filette M., W. M M Jou, A. Birkett, K. Lyons, B. Schultz, A. Tonkyro, et al. (2005). Universal influenza A vaccine: optimization of M2-based constructs. *Virology* 337:149-161.

De Filette M., W. Martens, K. Roose, T. Deroo, F. Vervalle, M. Bentahir, J. Vandekerckhove, W. Fiers, and X. Saelens (2008). An influenza A vaccine based on tetrameric ectodomain of matrix protein 2. *J. Biol. Chem.* 283:11382-11387.

Falsey A. R., C. K. Cunningham, W. H. Barker, R. W. Kouides, J. B. Yuen, M. Menegus, L. B. Weiner, C. A. Bonville, and R. F. Betts (1995). Respiratory syncytial virus and influenza A infection in the hospitalized elderly. *J. Infect. Dis.* 172:389-394.

Falsey A. R. and E. E. Walsh (1996). Safety and immunogenicity of a respiratory syncytial virus subunit vaccine (PFP-2) in ambulatory adults over age 60. *Vaccine* 14:1214-1218.

Falsey A. R. and W. W. Walsh (1997). Safety and immunogenicity of a respiratory syncytial virus subunit vaccine (PFP-2) in the institutionalized elderly. *Vaccine* 15:1130-1132.

Gimenez H. B., H. M. Keir, and P. Cash (1987). Immunoblot analysis of the human antibody response to respiratory syncytial virus infection. *J. Gen. Virol.* 68:1267-1275.

Groothuis J. R., S. J. King, D. A. Hogerman, P. R. Paradiso, and E. A. Simoes (1998). Safety and immunogenicity of a purified F protein respiratory syncytial virus (PFP-2) vaccine in seropositive children with bronchopulmonary dysplasia. *J. Infect. Dis.* 177:467-469.

Hacking D. and J. Hull (2002). Respiratory Syncytical virus—viral biology and the host response. *J. Infection* 45:18-24.

Hermanson G. T. (1996). *Bioconjugate Techniques*. Academic Press, Inc. 525 B street, San Diego, Calif. and Academic Press Limited, Oval Road, London, UK. ISBN-0-12-342335-X.

Jegerlehner A., A. Tissot, F. Lechner, P. Sebbel, I. Erdmann, T. Kundig, T. Bachi, T. Storni, G. Jennings, P. Pumpens, W. A. Renner, and M. F. Bachmann (2002). A molecular assembly system that renders antigens of choice highly repetitive for induction of protective B cell responses. *Vaccine* 20:3104-12.

Kapikian A. Z., R. H. Mitchell, R. M. Chanock, R. A. Shvedoff, and C. E. Stewart (1969). An epidemiologic study of altered clinical reactivity to respiratory syncytial (RS) virus infection in children previously vaccinated with an inactivated RS virus vaccine. *Am. J. Epidemiol.* 89:405-421.

Karron R. A., P. F. Wright, R. B. Belshe, B. Thumar, R. Casey, F. Newman, F. P. Polack, V. B. Randolph, A. Deatly, J. Hackell, W. Gruber, B. R. Murphy, and P. L. Collins (2005). Identification of a recombinant live attenuated respiratory syncytial virus vaccine candidate that is highly attenuated in infants. *J. Inf. Dis.* 191:1093-1104.

Liu J., W. Yong, Y. Deng, N. R. Kallenbach, and M. Lu (2004). Atomic structure of a tryptophan-zipper pentamer. *Proc. Natl. Acad. Sci. U.S.A.* 101:16156-61.

Liu J., Q. Zheng, Y. Deng, N. R. Kallenbach, and M. Lu (2006). Conformational transition between four- and five-stranded phenylalanine zippers determined by a local packing interaction. *J. Mol. Biol.* 361:168-79.

Malashkevich V. N., R. A. Kammerer, V. P. Efimov, T. Schulthess, and J. Engel (1996). The crystal structure of a five-stranded coiled coil in COMP: a prototype ion channel? *Science* 274:761-765.

McFarlane A. A., G. L. Orriss, and J. Stetefeld (2009). The use of coiled-coil proteins in drug delivery systems. *Eur. J. Pharmacol.* 625:101-107.

Mertens N., E. Remaut, and W. Fiers (1995). Versatile, multi-featured plasmids for high-level expression of heterologous genes in *Escherichia coli*: overproduction of human and murine cytokines. *Gene* 164:9-15.

Meyer G., M. Deplanche, and F. Schelcher (2008). Human and bovine respiratory syncytial virus vaccine research and development. *Comp. Immunol. Microbiol. Infect. Dis.* 31:191-225.

Murata Y. (2009). Respiratory Syncytial Virus vaccine development. *Clin. Lab. Med.* 29:725-739.

Neirynck S., T. Deroo, X. Saelens, P. Vanlandschoot, W. M. Jou, and W. Fiers (1999). A universal influenza A vaccine based on the extracellular domain of the M2 protein. *Nat. Med.* 5:1157-63.

Norton E. B., J. D. Clements, T. G. Voss, and L. Cardenas-Freytag (2010). Prophylactic administration of bacterially derived immunomodulators improves the outcome of influenza virus infection in a murine model. *J. Virol.* 84:2983-95.

Orga P. L. (2004). Respiratory syncytial virus: the virus, the disease and the immune response. *Pediatric Respiratory Reviews* 5, suppl. A, S119-S126.

Olmsted R. A. and P. L. Collins (1989). The 1A protein of respiratory syncytial virus is an integral membrane protein present as multiple, structurally distinct species. *J. Virol.* 63:2019-29.

Power U. F., T. N. Nguyen, E. Rietveld, R. L. de Swart, J. Groen, A. D. Osterhaus, R. de Groot, N. Corvaia, A. Beck, N. Bouveret-le-Cam, and J. Y. Bonnefoy (2001). Safety and immunogenicity of a novel recombinant subunit Respiratory Syncytial Virus vaccine (BBG2Na) in healthy young adults. *J. Infect. Dis.* 184:1456-1460.

Prescott, Jr., W. A., F. Doloresco, J. Brown and J. A. Paladino (2010). Cost effectiveness of respiratory syncytial virus prophylaxis: a critical and systematic review. *Pharmacoeconomics* 28:279-293.

Prince G. A., A. B. Jenson, R. L. Horswood, E. Camargo, and R. M. Chanock (1978). The pathogenesis of respiratory syncytial virus infection in cotton rats. *American Journal of Pathology* 93:771-791.

Prince G. A., A. B. Jenson, V. G. Hemming, B. R. Murphy, E. E. Walsh, R. L. Horswood, et al. (1986). Enhancement of respiratory syncytial virus pulmonary pathology in cotton rats by prior intramuscular inoculation of foimalin-inactivated virus. *J. Virol.* 57:721-728.

Schepens B., S. A. Tinton, Y. Bruynooghe, R. Beyaert, and S. Cornelis (2005). The polypyrimidine tract-binding protein stimulates HIF-1alpha IRES-mediated translation during hypoxia. *Nucleic Acids Res.* 33:6884-94.

Schmidt A. C., D. R. Wenzke, J. M. McAuliffe, M. St Claire, W. R. Elkins, B. R. Murphy, and P. L. Collins (2002). Mucosal immunization of rhesus monkeys against respiratory syncytial subgroups A and B and human parainfluenza virus type 3 by living cDNA-derived vaccine based on a host-range attenuated bovine parainfluenza virus type 3 vector backbone. *J. Virol.* 76:1089-1099.

Shu W., J. Liu, H. Ji, and M. Lu (2000). Core structure of the outer membrane lipoprotein from *Escherichia coli* at 1.9 A resolution. *J. Mol. Biol.* 299:1101-1112.

Slütter B., P. C. Soema, Z. Ding, R. Verheul, W. Hennink, and W. Jiskoot (2010). Conjugation of ovalbumin to trimethul chitosan improves immunogenicity of the antigen. *J. Controlled Release* 143:207-214.

Timmerman P, W. C. Puijk, and R. H. Meloen (2007). Functional reconstruction and synthetic mimicry of a conformational epitope using CLIPS™ technology. *L. Mol. Recognition.* 20:283-299.

Tsutsumi H., T. Honjo, K. Nagai, Y. Chiba, S. Chiba, and S. Tsuguwa (1989). Immunoglobulin A antibody response to respiratory syncytial virus structural proteins in colostrums and milk. *J. Clinical Microbiol.* 27:1949-1951.

Whitacre D. C., B. O. Lee, and D. R. Milich (2009). Use of hepadnavirus core proteins as vaccine platforms. *Expert Rev. Vaccines* 8:1565-1573.

Schepens B., S. A. Tinton, Y. Bruynooghe, R. Beyaert, and S. Cornelis (2005). The translation during hypoxia. *Nucleic Acids Res.* 33:6884-94.

Williams J. P., D. C. Smith, B. N. Green, B. D. Marsden, K. R. Jennings, L. M. Roberts, and J. H. Scrivens (2006). Gas phase characterization of the noncovalent quaternary structure of cholera toxin and the cholera toxin B subunit pentamer. *Biophys. J.* 90:3246-54.

The invention claimed is:

1. A method of evoking protective immunity in a subject against Respiratory Syncytial Virus infection, the method comprising:
    administering to a subject in need thereof an immunogenic composition comprising the ectodomain of the small hydrophobic protein of a Respiratory Syncytial Virus, wherein the ectodomain comprises SEQ ID NO: 1, wherein the composition comprises a carrier heterologous to the ectodomain, and wherein the cysteine residue at position 4 is optionally replaced with a serine residue.

2. The method of claim 1, wherein said ectodomain is presented as an oligomer.

3. The method of claim 1, wherein the ectodomain is genetically linked to the carrier.

4. The method of claim 1, wherein the ectodomain is chemically linked to the carrier.

5. The method of claim 1, wherein the carrier is an oligomer.

6. The method of claim 5, wherein said oligomer is a pentamer.

7. The method of claim 1, wherein the carrier is selected from the group consisting of Cartilage Oligomeric Matrix Protein (comp), Lpp-56, and a virus-like particle.

8. The method of claim 1, wherein the ectodomain comprises SEQ ID NO: 1.

9. The method of claim 1, wherein the ectodomain comprises SEQ ID NO: 1 with the cysteine residue at position 4 replaced with a serine residue.

10. The method of claim 1, comprising administering the immunogenic composition to the subject prior to exposure of the subject to Respiratory Syncytial Virus.

11. The method of claim 1, wherein the carrier is a non-proteinaceous carrier.

12. The method of claim 11, wherein the non-proteinaceous carrier is a liposome.

* * * * *

SEQUENCE LISTING

<160> NUMBER OF SEQ ID NOS: 55

<210> SEQ ID NO 1
<211> LENGTH: 23
<212> TYPE: PRT
<213> ORGANISM: respiratory syncytial virus

<400> SEQUENCE: 1

```
Asn Lys Leu Cys Glu Tyr Asn Val Phe His Asn Lys Thr Phe Glu Leu
1               5                   10                  15

Pro Arg Ala Arg Val Asn Thr
            20

<210> SEQ ID NO 2
<211> LENGTH: 24
<212> TYPE: PRT
<213> ORGANISM: respiratory syncytial virus

<400> SEQUENCE: 2

Asn Lys Leu Ser Glu His Lys Thr Phe Cys Asn Asn Thr Leu Glu Leu
1               5                   10                  15

Gly Gln Met His Gln Ile Asn Thr
            20

<210> SEQ ID NO 3
<211> LENGTH: 9
<212> TYPE: PRT
<213> ORGANISM: Artificial Sequence
<220> FEATURE:
<223> OTHER INFORMATION: Variant of ectodomain
<220> FEATURE:
<221> NAME/KEY: MISC_FEATURE
<222> LOCATION: (4)..(4)
<223> OTHER INFORMATION: Xaa can be Cys or Ser
<220> FEATURE:
<221> NAME/KEY: MISC_FEATURE
<222> LOCATION: (6)..(6)
<223> OTHER INFORMATION: Xaa can be Tyr or His
<220> FEATURE:
<221> NAME/KEY: MISC_FEATURE
<222> LOCATION: (7)..(7)
<223> OTHER INFORMATION: Xaa can be Asn or Lys
<220> FEATURE:
<221> NAME/KEY: misc_feature
<222> LOCATION: (8)..(8)
<223> OTHER INFORMATION: Xaa can be any naturally occurring amino acid

<400> SEQUENCE: 3

Asn Lys Leu Xaa Glu Xaa Xaa Xaa Phe
1               5

<210> SEQ ID NO 4
<211> LENGTH: 23
<212> TYPE: PRT
<213> ORGANISM: respiratory syncytial virus

<400> SEQUENCE: 4

Asn Lys Leu Cys Glu Tyr Asn Ile Phe His Asn Lys Thr Phe Glu Leu
1               5                   10                  15

Pro Arg Ala Arg Val Asn Thr
            20

<210> SEQ ID NO 5
<211> LENGTH: 23
<212> TYPE: PRT
<213> ORGANISM: respiratory syncytial virus

<400> SEQUENCE: 5

Asn Lys Leu Cys Glu Tyr Asn Val Phe His Asn Lys Thr Phe Glu Leu
1               5                   10                  15

Pro Lys Ala Arg Val Asn Thr
            20
```

-continued

```
<210> SEQ ID NO 6
<211> LENGTH: 23
<212> TYPE: PRT
<213> ORGANISM: respiratory syncytial virus

<400> SEQUENCE: 6

Asn Lys Leu Cys Glu Tyr Asn Val Phe Tyr Asn Lys Thr Phe Glu Leu
1               5                   10                  15

Pro Arg Ala Arg Val Asn Thr
            20

<210> SEQ ID NO 7
<211> LENGTH: 23
<212> TYPE: PRT
<213> ORGANISM: respiratory syncytial virus

<400> SEQUENCE: 7

Asn Lys Leu Cys Glu Tyr Asn Ala Phe His Asn Lys Thr Phe Glu Leu
1               5                   10                  15

Pro Arg Ala Arg Ile Asn Thr
            20

<210> SEQ ID NO 8
<211> LENGTH: 24
<212> TYPE: PRT
<213> ORGANISM: respiratory syncytial virus

<400> SEQUENCE: 8

Asn Lys Leu Ser Glu His Lys Thr Phe Cys Asn Lys Thr Leu Glu Leu
1               5                   10                  15

Gly Gln Met Tyr Gln Ile Asn Thr
            20

<210> SEQ ID NO 9
<211> LENGTH: 24
<212> TYPE: PRT
<213> ORGANISM: respiratory syncytial virus

<400> SEQUENCE: 9

Asn Lys Leu Ser Glu His Lys Thr Phe Cys Asn Lys Thr Leu Glu Gln
1               5                   10                  15

Gly Gln Met Tyr Gln Val Asn Thr
            20

<210> SEQ ID NO 10
<211> LENGTH: 24
<212> TYPE: PRT
<213> ORGANISM: respiratory syncytial virus

<400> SEQUENCE: 10

Asn Lys Leu Ser Glu His Lys Ala Phe Cys Asn Lys Thr Leu Glu Gln
1               5                   10                  15

Gly Gln Met Tyr Gln Ile Asn Thr
            20

<210> SEQ ID NO 11
<211> LENGTH: 24
<212> TYPE: PRT
<213> ORGANISM: respiratory syncytial virus

<400> SEQUENCE: 11

Asn Lys Leu Ser Glu His Lys Ile Phe Cys Asn Lys Thr Leu Glu Gln
1               5                   10                  15
```

```
Gly Gln Met Tyr Gln Ile Asn Thr
            20

<210> SEQ ID NO 12
<211> LENGTH: 24
<212> TYPE: PRT
<213> ORGANISM: respiratory syncytial virus

<400> SEQUENCE: 12

Asn Lys Leu Ser Glu His Lys Pro Phe Cys Asn Lys Thr Leu Glu Gln
1               5                   10                  15

Gly Gln Met Tyr Gln Ile Asn Thr
            20

<210> SEQ ID NO 13
<211> LENGTH: 24
<212> TYPE: PRT
<213> ORGANISM: respiratory syncytial virus

<400> SEQUENCE: 13

Asn Lys Leu Ser Glu His Lys Thr Phe Cys Asn Lys Thr Leu Glu Gln
1               5                   10                  15

Gly Gln Val Tyr Gln Ile Asn Thr
            20

<210> SEQ ID NO 14
<211> LENGTH: 24
<212> TYPE: PRT
<213> ORGANISM: respiratory syncytial virus

<400> SEQUENCE: 14

Asn Lys Leu Ser Glu His Lys Thr Phe Tyr Asn Lys Thr Leu Glu Gln
1               5                   10                  15

Gly Gln Met Tyr Gln Ile Asn Thr
            20

<210> SEQ ID NO 15
<211> LENGTH: 24
<212> TYPE: PRT
<213> ORGANISM: respiratory syncytial virus

<400> SEQUENCE: 15

Asn Lys Leu Ser Glu His Lys Ile Phe Cys Asn Lys Thr Leu Glu Gln
1               5                   10                  15

Gly Gln Met Tyr Gln Ile His Thr
            20

<210> SEQ ID NO 16
<211> LENGTH: 24
<212> TYPE: PRT
<213> ORGANISM: respiratory syncytial virus

<400> SEQUENCE: 16

Asn Lys Leu Ser Glu His Lys Thr Phe Phe Asn Lys Thr Leu Glu Gln
1               5                   10                  15

Gly Gln Met Tyr Gln Ile Asn Thr
            20

<210> SEQ ID NO 17
<211> LENGTH: 40
<212> TYPE: PRT
<213> ORGANISM: respiratory syncytial virus
```

<400> SEQUENCE: 17

Asn Lys Leu Cys Asp Phe Asn Asp His His Thr Asn Ser Leu Asp Ile
1               5                   10                  15

Arg Thr Arg Leu Arg Asn Asp Thr Gln Leu Ile Thr Arg Ala His Glu
            20                  25                  30

Gly Ser Ile Asn Gln Ser Ser Asn
        35                  40

<210> SEQ ID NO 18
<211> LENGTH: 14
<212> TYPE: PRT
<213> ORGANISM: Artificial Sequence
<220> FEATURE:
<223> OTHER INFORMATION: Variant of ectodomain
<220> FEATURE:
<221> NAME/KEY: misc_feature
<222> LOCATION: (5)..(9)
<223> OTHER INFORMATION: Xaa can be any naturally occurring amino acid

<400> SEQUENCE: 18

Asn Lys Leu Cys Xaa Xaa Xaa Xaa Xaa His Thr Asn Ser Leu
1               5                   10

<210> SEQ ID NO 19
<211> LENGTH: 40
<212> TYPE: PRT
<213> ORGANISM: respiratory syncytial virus

<400> SEQUENCE: 19

Asn Lys Leu Cys Asp Phe Asn Asp Arg His Thr Asn Ser Leu Asp Ile
1               5                   10                  15

Arg Thr Arg Leu Arg Asp Asp Thr Gln Leu Ile Thr Arg Ala His Glu
            20                  25                  30

Gly Ser Ile Asn Gln Ser Ser Asn
        35                  40

<210> SEQ ID NO 20
<211> LENGTH: 40
<212> TYPE: PRT
<213> ORGANISM: respiratory syncytial virus

<400> SEQUENCE: 20

Asn Lys Leu Cys Asp Leu Asn Asp His His Thr Asn Ser Leu Asp Ile
1               5                   10                  15

Arg Thr Arg Leu Arg Asn Asp Thr Gln Leu Thr Thr Arg Ala His Glu
            20                  25                  30

Gly Pro Ile Asn Gln Ser Ser Asn
        35                  40

<210> SEQ ID NO 21
<211> LENGTH: 40
<212> TYPE: PRT
<213> ORGANISM: respiratory syncytial virus

<400> SEQUENCE: 21

Asn Lys Leu Cys Asp Leu Asn Asn His His Thr Asn Ser Leu Asp Ile
1               5                   10                  15

Arg Thr Arg Leu Arg Asn Asp Thr Gln Ser Ile Thr Arg Ala His Glu
            20                  25                  30

Gly Ser Ile Asn Gln Ser Ser Asn
        35                  40

<210> SEQ ID NO 22
<211> LENGTH: 40
<212> TYPE: PRT
<213> ORGANISM: respiratory syncytial virus

<400> SEQUENCE: 22

Asn Lys Leu Cys Asp Leu Asn Asp His His Thr Asn Ser Leu Asp Ile
1               5                   10                  15

Arg Thr Lys Leu Arg Ser Asp Thr Gln Leu Ile Thr Ala His Glu
            20                  25                  30

Glu Ser Ile Asn Gln Ser Ser Asn
        35                  40

<210> SEQ ID NO 23
<211> LENGTH: 40
<212> TYPE: PRT
<213> ORGANISM: respiratory syncytial virus

<400> SEQUENCE: 23

Asn Lys Leu Cys Asp Leu Asn Asn His His Thr Asn Ser Leu Asp Ile
1               5                   10                  15

Lys Thr Arg Leu Arg Asn Asp Thr Gln Ser Ile Thr Arg Ala His Glu
            20                  25                  30

Gly Ser Ile Asn Gln Ser Ser Asn
        35                  40

<210> SEQ ID NO 24
<211> LENGTH: 40
<212> TYPE: PRT
<213> ORGANISM: respiratory syncytial virus

<400> SEQUENCE: 24

Asn Lys Leu Cys Asp Leu Asn Asn His His Thr Asn Ser Leu Asp Ile
1               5                   10                  15

Lys Thr Arg Leu Lys Asn Asp Thr Gln Ser Ile Thr Arg Ala His Glu
            20                  25                  30

Gly Ser Ile Asn Gln Ser Ser Asn
        35                  40

<210> SEQ ID NO 25
<211> LENGTH: 40
<212> TYPE: PRT
<213> ORGANISM: respiratory syncytial virus

<400> SEQUENCE: 25

Asn Lys Leu Cys Val Leu Asn Asn His His Thr Asn Ser Leu Asp Ile
1               5                   10                  15

Arg Thr Arg Leu Arg Asn Asp Thr Gln Ser Ile Thr Arg Ala His Glu
            20                  25                  30

Gly Ser Ile Asn Gln Ser Ser Asn
        35                  40

<210> SEQ ID NO 26
<211> LENGTH: 40
<212> TYPE: PRT
<213> ORGANISM: respiratory syncytial virus

<400> SEQUENCE: 26

Asn Lys Leu Cys Asp Leu Asn Asn His His Thr Asn Ser Leu Glu Ile
1               5                   10                  15

```
Lys Thr Arg Leu Arg Asn Asp Thr Gln Ser Ile Thr Lys Ala His Glu
            20                  25                  30

Gly Ser Ile Asn Gln Ser Ser Asn
        35                  40

<210> SEQ ID NO 27
<211> LENGTH: 40
<212> TYPE: PRT
<213> ORGANISM: respiratory syncytial virus

<400> SEQUENCE: 27

Asn Lys Leu Cys Asp Leu Asn Asn His His Thr Asn Ser Leu Asp Ile
1               5                   10                  15

Lys Thr Arg Leu Arg Asn Asp Thr Gln Ser Thr Thr Arg Ala His Glu
            20                  25                  30

Gly Ser Ile Asn Gln Ser Ser Asn
        35                  40

<210> SEQ ID NO 28
<211> LENGTH: 40
<212> TYPE: PRT
<213> ORGANISM: respiratory syncytial virus

<400> SEQUENCE: 28

Asn Lys Leu Cys Val Leu Ser Asn His His Thr Asn Ser Leu Asp Ile
1               5                   10                  15

Arg Thr Arg Leu Arg Asn Asp Thr Gln Ser Ile Thr Arg Ala His Glu
            20                  25                  30

Gly Ser Ile Asn Gln Ser Ser Asn
        35                  40

<210> SEQ ID NO 29
<211> LENGTH: 36
<212> TYPE: PRT
<213> ORGANISM: respiratory syncytial virus

<400> SEQUENCE: 29

Asn Lys Leu Cys Val Leu Asn Asn His His Thr Asn Ser Leu Asp Ile
1               5                   10                  15

Arg Thr Arg Leu Arg Asn Asp Thr Gln Ser Ile Thr Arg Ala His Glu
            20                  25                  30

Gly Ser Ile Asn
        35

<210> SEQ ID NO 30
<211> LENGTH: 31
<212> TYPE: PRT
<213> ORGANISM: respiratory syncytial virus

<400> SEQUENCE: 30

Asn Lys Leu Cys Asp Leu Asn Asp His His Thr Asn Ser Leu Asp Ile
1               5                   10                  15

Arg Thr Gly Leu Arg Asn Asp Thr Gln Ser Ile Thr Arg Ala His
            20                  25                  30

<210> SEQ ID NO 31
<211> LENGTH: 2973
<212> TYPE: DNA
<213> ORGANISM: Artificial Sequence
<220> FEATURE:
<223> OTHER INFORMATION: Plasmid puc57-comp5SHe
```

```
<220> FEATURE:
<221> NAME/KEY: misc_feature
<222> LOCATION: (440)..(442)
<223> OTHER INFORMATION: Startcodon reading frame Flag-COMPcc-SHe
<220> FEATURE:
<221> NAME/KEY: misc_feature
<222> LOCATION: (671)..(673)
<223> OTHER INFORMATION: Stopcodon reading frame Flag-COMPcc-SHe

<400> SEQUENCE: 31
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta cgccagggt      360 tttcccagtc acgacgttgt aaaacgacgg ccagtgaatt cgagctcggt acctcgcgaa     420
tgcatctaga tattggcata tggattacaa agatgatgat gataaagatc tggccccaca     480
gatgctgcgt gaactgcagg aaaccaatgc agccctgcag gatgttcgtg aactgctgcg     540
tcaccgtgtg aaagaaatta ccttcctgaa aaatacggtc atggaatgtg acgcttgcgg     600
caacaaactg tgcgaatata tgttttttca ataaaaaacc tttgaactgc ctcgtgcacg     660
tgtgaacacc taaaagctta tgcatgcggc cgcattggga tcccgggccc gtcgactgca     720
gaggcctgca tgcaagcttg gcgtaatcat ggtcatagct gtttcctgtg tgaaattgtt     780
atccgctcac aattccacac aacatacgag ccggaagcat aaagtgtaaa gcctggggtg     840
cctaatgagt gagctaactc acattaattg cgttgcgctc actgcccgct ttccagtcgg     900
gaaacctgtc gtgccagctg cattaatgaa tcggccaacg cgcggggaga ggcggtttgc     960
gtattgggcg ctcttccgct tcctcgctca ctgactcgct gcgctcggtc gttcggctgc    1020
ggcgagcggt atcagctcac tcaaaggcgg taatacggtt atccacagaa tcaggggata    1080
acgcaggaaa gaacatgtga gcaaaaggcc agcaaaaggc caggaaccgt aaaaaggccg    1140
cgttgctggc gtttttccat aggctccgcc cccctgacga gcatcacaaa aatcgacgct    1200
caagtcagag gtggcgaaac ccgacaggac tataaagata ccaggcgttt ccccctggaa    1260
gctccctcgt gcgctctcct gttccgaccc tgccgcttac cggatacctg tccgcctttc    1320
tcccttcggg aagcgtggcg ctttctcata gctcacgctg taggtatctc agttcggtgt    1380
aggtcgttcg ctccaagctg ggctgtgtgc acgaaccccc cgttcagccc gaccgctgcg    1440
ccttatccgg taactatcgt cttgagtcca acccggtaag acacgactta tcgccactgg    1500
cagcagccac tggtaacagg attagcagag cgaggtatgt aggcggtgct acagagttct    1560
tgaagtggtg gcctaactac ggctacacta agaacagt atttggtatc tgcgctctgc    1620
tgaagccagt taccttcgga aaagagttgg tagctcttg atccggcaaa caaccaccg    1680 ctggtagcgg tggttttttt gtttgcaagc agcagattac gcgcagaaaa aaggatctc    1740 aagaagatcc tttgatcttt tctacggggt ctgacgctca gtggaacgaa aactcacgtt    1800
aagggatttt ggtcatgaga ttatcaaaaa ggatcttcac ctagatcctt ttaaattaaa    1860
aatgaagttt taaatcaatc taaagtatat atgagtaaac ttggtctgac agttaccaat    1920
gcttaatcag tgaggcacct atctcagcga tctgtctatt tcgttcatcc atagttgcct    1980
gactccccgt cgtgtagata actacgatac gggagggctt accatctggc cccagtgctg    2040
```

```
caatgatacc gcgagaccca cgctcaccgg ctccagattt atcagcaata aaccagccag    2100
ccggaagggc cgagcgcaga agtggtcctg caactttatc cgcctccatc cagtctatta    2160
attgttgccg ggaagctaga gtaagtagtt cgccagttaa tagtttgcgc aacgttgttg    2220
ccattgctac aggcatcgtg gtgtcacgct cgtcgtttgg tatggcttca ttcagctccg    2280
gttcccaacg atcaaggcga gttacatgat cccccatgtt gtgcaaaaaa gcggttagct    2340
ccttcggtcc tccgatcgtt gtcagaagta agttggccgc agtgttatca ctcatggtta    2400
tggcagcact gcataattct cttactgtca tgccatccgt aagatgcttt tctgtgactg    2460
gtgagtactc aaccaagtca ttctgagaat agtgtatgcg gcgaccgagt tgctcttgcc    2520
cggcgtcaat acgggataat accgcgccac atagcagaac tttaaaagtg ctcatcattg    2580
gaaaacgttc ttcggggcga aaactctcaa ggatcttacc gctgttgaga tccagttcga    2640
tgtaacccac tcgtgcaccc aactgatctt cagcatcttt tactttcacc agcgtttctg    2700
ggtgagcaaa aacaggaagg caaaatgccg caaaaaaggg aataagggcg acacggaaat    2760
gttgaatact catactcttc cttttcaat attattgaag catttatcag ggttattgtc    2820
tcatgagcgg atacatattt gaatgtattt agaaaaataa acaaataggg gttccgcgca    2880
catttccccg aaaagtgcca cctgacgtct aagaaaccat tattatcatg acattaacct    2940
ataaaaatag gcgtatcacg aggccctttc gtc                                2973

<210> SEQ ID NO 32
<211> LENGTH: 525
<212> TYPE: DNA
<213> ORGANISM: Artificial Sequence
<220> FEATURE:
<223> OTHER INFORMATION: mHBc expression vector

<400> SEQUENCE: 32
gggcgaattg ggtaccggaa ttccatatgg atatcgatcc gtacaaagaa tttggcgcga     60
ccgtggaact gctgtctttt ctgccgagcg attttttttcc gagcgtgcgt gatctgctgg    120
ataccgcgag cgcgctgtat cgtgaagcgc tggaaagccc ggaacatagc agcccgcatc    180
ataccgcgct gcgtcaggcg attctgtgct ggggcgaact gatgaccctg gccacctggg    240
tgggcgtgaa cctggaagat ggcggcaaag cggcagccg tgatctggtg gtgagctatg    300
tgaacaccaa catgggcctg aaatttcgtc agctgctgtg gtttcatatc agcagcctga    360
cctttggccg tgaaaccgtg ctggaatatc tggtgagctt tggcgtgtgg attcgtactc    420
cgccggcata tcgtccgccg aacgcgccga ttctgagcac cctgccggaa accaccgtgg    480
tgtgctagcg gccgcaaaag gaaaagagct ccagcttttg ttccc                    525

<210> SEQ ID NO 33
<211> LENGTH: 358
<212> TYPE: DNA
<213> ORGANISM: Artificial Sequence
<220> FEATURE:
<223> OTHER INFORMATION: SHe expression vector

<400> SEQUENCE: 33
gggcgaattg ggtaccctgc agaaccacgt gggtgggtgt taacttggaa gatggcggca     60
gcaacaaact gtgcgaatat aacgtgttcc acaataaaac ctttgaactg ccgcgtgcgc    120
gtgtgaatac cagcggcggc agcggtggtt cgaataaact gtgtgaatac aatgtctttc    180
ataacaagac gttcgaactg ccacgtgccc gcgtcaacac ctctggtggt agcggcggct    240
ctaacaagtt atgtgagtac aacgtattcc acaacaagac atttgagttg cctcgggcac    300
```
gagtaaatac atctggtggt gctagcaggg acctggtaga gctccagctt ttgttccc      358

<210> SEQ ID NO 34
<211> LENGTH: 3250
<212> TYPE: DNA
<213> ORGANISM: Artificial Sequence
<220> FEATURE:
<223> OTHER INFORMATION: Template plasmid
<220> FEATURE:
<221> NAME/KEY: misc_feature
<222> LOCATION: (3150)..(3150)
<223> OTHER INFORMATION: n is a, c, g, or t

<400> SEQUENCE: 34

```
atgaacaatg ctaccttcaa ctatacaaac gttaaccctc tttctcacat caggggaggt      60
ttaaaacaaa tcgaagacaa gctggaagaa atcctttcga aactgtacca catcgaaaac     120
gagctggcca ggatcaagaa actgctgggc gaagaattcg aaggaatgga ctacaaggat     180
catgatggtg attataaaga ccacgacatt gactataagg atgatgatga caaataggaa     240
gcttatgcat gcggccgcat ctagagggcc cggatccctc gaggtcgacg aattcgagct     300
cggccgactt ggccttccct ttagtgaggg ttaataaact tggtgagcaa taactagcat     360
aaccccttgg ggcctctaaa cgggtcttga ggggttttt gctgaaagga ggaactatat      420
gcgctcatac gatatgaacg ttgagactgc cgctgagtta tcagtgagca ataactagca     480
taaccccttg gggcctctaa acgggtcttg aggggttttt tgctgaaagg aggaactata     540
tccggccgga tagcttatcg ctagaggtcg aaattcacct cgaaagcaag ctgataaacc     600
gatacaatta aaggctcctt ttggagcctt ttttttgga dttttcaac gtgaaaaaat      660
tattattcgc aattccaagc taattcacct cgaaagcaag ctgataaacc gatacaatta     720
aaggctcctt ttggagcctt ttttttgga dttttcaac gtgaaaaaat tattattcgc      780
aattccaagc tctgcctcgc gcgttttcggt gatgacggtg aaaacctctg acacatgcag     840
ctcccctagc aattgcatgt gagcaaaagg ccagcaaaag gccaggaacc gtaaaaaggc     900
cgcgttgctg gcgttttcc ataggctccg ccccctgac gagcatcaca aaaatcgacg      960
ctcaagtcag aggtggcgaa acccgacagg actataaaga taccaggcgt ttccccctgg    1020
aagctccctc gtgcgctctc ctgttccgac cctgccgctt accggatacc tgtccgcctt    1080
tctcccttcg ggaagcgtgg cgctttctca gctcacgc tgtaggtatc tcagttcggt      1140
gtaggtcgtt cgctccaagc tgggctgtgt gcacgaaccc cccgttcagc ccgaccgctg    1200
cgccttatcc ggtaactatc gtcttgagtc caacccggta agacacgact tatcgccact    1260
ggcagcagcc actggtaaca ggattagcag agcgaggtat gtaggcggtg ctacagagtt    1320
cttgaagtgg tggcctaact acggctacac tagaaggaca gtatttggta tctgcgctct    1380
gctgaagcca gttaccttcg gaaaaagagt tggtagctct tgatccggca acaaaccac     1440
cgctggtagc ggtggttttt ttgtttgcaa gcagcagatt acgcgcagaa aaaaaggatc    1500
tcaagaagat cctttgatct tttctacggg gtctgacgct cagtggaacg aaaactcacg    1560
ttaagggatt ttggtcatga gattatcaaa aaggatcttc acctagatcc ttttaaatta    1620
aaaatgaagt tttaaatcaa tctaaagtat atatgagtaa acttggtctg acagttacca    1680
atgcttaatc agtgaggcac ctatctcagc gatctgtcta tttcgttcat ccatagttgc    1740
ctgactcccc gtcgtgtaga taactacgat acgggagggc ttaccatctg gccccagtgc    1800
tgcaatgata ccgcgagacc cacgctcacc ggctccagat ttatcagcaa taaaccagcc    1860
```

-continued

```
agccggaagg gccgagcgca gaagtggtcc tgcaacttta tccgcctcca tccagtctat   1920
taattgttgc cgggaagcta gagtaagtag ttcgccagtt aatagtttgc gcaacgttgt   1980
tgccattgct gcaggcatcg tggtgtcacg ctcgtcgttt ggtatggctt cattcagctc   2040
cggttcccaa cgatcaaggc gagttacatg atcccccatg ttgtgcaaaa aagcggttag   2100
ctccttcggt cctccgatcg ttgtcagaag taagttggcc gcagtgttat cactcatggt   2160
tatggcagca ctgcataatt ctcttactgt catgccatcc gtaagatgct tttctgtgac   2220
tggtgagtac tcaaccaagt cattctgaga atagtgtatg cggcgaccga gttgctcttg   2280
cccggcgtca acacgggata ataccgcgcc acatagcaga actttaaaag tgctcatcat   2340
tggaaaacgt tcttcggggc gaaaactctc aaggatctta ccgctgttga gatccagttc   2400
gatgtaaccc actcgtgcac ccaactgatc ttcagcatct tttactttca ccagcgtttc   2460
tgggtgagca aaaacaggaa ggcaaaatgc cgcaaaaaag ggaataaggg cgacacggaa   2520
atgttgaata ctcatactct tcctttttca atattatgta agcagacagt tttattgttc   2580
atgatgatat atttttatct tgtgcaatgt aacatcagag atttgagac acaacgtggc   2640 tttgttgaat aaatcgaact tttgctgagt tgaaggatca gatcacgcat cttcccgaca   2700
acgcagaccg ttccgtggca aagcaaaagt tcaaaatcac caactggtcc acctacaaca   2760
aagctctcat caaccgtggc tccctcactt tctggctgga tgatggggcg attcaggcct   2820
ggtatgagtc agcaacacct tcttcacgag gcagacctca gcgccggtga tgccggccac   2880
gatgcgtccg gcgtagagga tctctcacct accaaacaat gcccccctgc aaaaaataaa   2940
ttcatataaa aaacatacag ataaccatct gcggtgataa attatctctg gcggtgttga   3000
cataaatacc actggcggtg atactgagca catcagcagg acgcactgac caccatgaag   3060
gtgacgctct taaaattaag ccctgaagaa gggcagcatt caaagcagaa ggctttgggg   3120
tgtgtgatac gaaacgaagc attggaattn cggatctcga tcccggaaat taatacgact   3180
cactataggg agaccacaac ggtttccctc tagaaataat tttgtttaac tttaagaagg   3240
agatatacat                                                          3250
```

<210> SEQ ID NO 35
<211> LENGTH: 77
<212> TYPE: PRT
<213> ORGANISM: Artificial Sequence
<220> FEATURE:
<223> OTHER INFORMATION: Vaccine Flag-COMPcc-SHe

<400> SEQUENCE: 35

```
Met Asp Tyr Lys Asp Asp Asp Asp Lys Asp Leu Ala Pro Gln Met Leu
1               5                   10                  15

Arg Glu Leu Gln Glu Thr Asn Ala Ala Leu Gln Asp Val Arg Glu Leu
            20                  25                  30

Leu Arg His Gln Val Lys Glu Ile Thr Phe Leu Lys Asn Thr Val Met
        35                  40                  45

Glu Cys Asp Ala Cys Gly Asn Lys Leu Cys Glu Tyr Asn Val Phe His
    50                  55                  60

Asn Lys Thr Phe Glu Leu Pro Arg Ala Arg Val Asn Thr
65                  70                  75
```

<210> SEQ ID NO 36
<211> LENGTH: 42
<212> TYPE: DNA
<213> ORGANISM: Artificial Sequence
<220> FEATURE:

<223> OTHER INFORMATION: Primer

<400> SEQUENCE: 36
ataagaaagc ggccgctatg gaaaatacat ccataacaat ag                42

<210> SEQ ID NO 37
<211> LENGTH: 41
<212> TYPE: DNA
<213> ORGANISM: Artificial Sequence
<220> FEATURE:
<223> OTHER INFORMATION: Primer

<400> SEQUENCE: 37
gaagatctct atgtgttgac tcgagctctt ggtaactcaa a                 41

<210> SEQ ID NO 38
<211> LENGTH: 35
<212> TYPE: DNA
<213> ORGANISM: Artificial Sequence
<220> FEATURE:
<223> OTHER INFORMATION: Primer

<400> SEQUENCE: 38
ggaattccat atgaacaagt tatgtgagta caacg                       35

<210> SEQ ID NO 39
<211> LENGTH: 42
<212> TYPE: DNA
<213> ORGANISM: Artificial Sequence
<220> FEATURE:
<223> OTHER INFORMATION: Primer

<400> SEQUENCE: 39
gatttgtttt aaacctcctg tatttactcg tgcccgaggc aa                42

<210> SEQ ID NO 40
<211> LENGTH: 23
<212> TYPE: PRT
<213> ORGANISM: respiratory syncytial virus

<400> SEQUENCE: 40

Asn Lys Leu Cys Glu Tyr Asn Val Phe His Asn Lys Thr Phe Glu Leu
1               5                   10                  15

Pro Arg Ala Arg Val Asn Thr
20

<210> SEQ ID NO 41
<211> LENGTH: 36
<212> TYPE: DNA
<213> ORGANISM: Artificial Sequence
<220> FEATURE:
<223> OTHER INFORMATION: Primer

<400> SEQUENCE: 41
cccaagcttc taacattgag attcccgaga ttgaga 36

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
tattaaccct cactaaaggg aagg 24

<210> SEQ ID NO 43
<211> LENGTH: 35
<212> TYPE: DNA
<213> ORGANISM: Artificial Sequence
<220> FEATURE:
<223> OTHER INFORMATION: Primer

<400> SEQUENCE: 43
ggaattccat atgaacaagt tatgtgagta caacg                     35

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
tattaaccct cactaaaggg aagg                                 24

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
tcacgaaggc tccacataca                                      20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gcagggtcat cgtcttttc                                       20

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
tgaagcaggc atctgaggg                                       19

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
cgaaggtgga agagtgggag                                      20

<210> SEQ ID NO 49
<211> LENGTH: 3252
<212> TYPE: DNA
<213> ORGANISM: Artificial Sequence
<220> FEATURE:

<223> OTHER INFORMATION: pLH36-HisDEVD-LPP(5)-SHe plasmid

<400> SEQUENCE: 49

```
gctgaaagga ggaactatat ccggccggat agcttatcgc tagaggtcga aattcacctc    60
gaaagcaagc tgataaaccg atacaattaa aggctccttt tggagccttt tttttttggag   120
attttcaacg tgaaaaaatt attattcgca attccaagct aattcacctc gaaagcaagc   180
tgataaaccg atacaattaa aggctccttt tggagccttt tttttggag attttcaacg    240
tgaaaaaatt attattcgca attccaagct ctgcctcgcg cgtttcggtg atgacggtga   300
aaacctctga cacatgcagc tcccaggca attgcatgtg agcaaaaggc cagcaaaagg    360
ccaggaaccg taaaaaggcc gcgttgctgg cgttttttcca taggctccgc ccccctgacg   420
agcatcacaa aaatcgacgc tcaagtcaga ggtggcgaaa cccgacagga ctataaagat   480
accaggcgtt ccccctgga agctccctcg tgcgctctcc tgttccgacc ctgccgctta    540
ccggatacct gtccgccttt ctcccttcgg gaagcgtggc gctttctcat agctcacgct   600
gtaggtatct cagttcggtg taggtcgttc gctccaagct gggctgtgtg cacgaacccc   660
ccgttcagcc cgaccgctgc gccttatccg gtaactatcg tcttgagtcc aacccggtaa   720
gacacgactt atcgccactg gcagcagcca ctggtaacag gattagcaga gcgaggtatg   780
taggcggtgc tacagagttc ttgaagtggt ggcctaacta cggctacact agaaggacag   840
tatttggtat ctgcgctctg ctgaagccag ttaccttcgg aaaaagagtt ggtagctctt   900
gatccggcaa acaaaccacc gctggtagcg gtggtttttt tgtttgcaag cagcagatta   960
cgcgcagaaa aaaggatct caagaagatc ctttgatctt ttctacgggg tctgacgctc   1020
agtggaacga aaactcacgt taagggattt tggtcatgag attatcaaaa aggatcttca   1080
cctagatcct tttaaattaa aaatgaagtt ttaaatcaat ctaaagtata tatgagtaaa   1140
cttggtctga cagttaccaa tgcttaatca gtgaggcacc tatctcagcg atctgtctat   1200
ttcgttcatc catagttgcc tgactccccg tcgtgtagat aactacgata cgggagggct   1260
taccatctgg ccccagtgct gcaatgatac cgcgagaccc acgctcaccg gctccagatt   1320
tatcagcaat aaaccagcca gccggaaggg ccgagcgcag aagtggtcct gcaactttat   1380
ccgcctccat ccagtctatt aattgttgcc gggaagctag agtaagtagt tcgccagtta   1440
atagtttgcg caacgttgtt gccattgctg caggcatcgt ggtgtcacgc tcgtcgtttg   1500
gtatggcttc attcagctcc ggttcccaac gatcaaggcg agttacatga tcccccatgt   1560
tgtgcaaaaa agcggttagc tccttcggtc ctccgatcgt tgtcagaagt aagttggccg   1620
cagtgttatc actcatggtt atggcagcac tgcataattc tcttactgtc atgccatccg   1680
taagatgctt ttctgtgact ggtgagtact caaccaagtc attctgagaa tagtgtatgc   1740
ggcgaccgag ttgctcttgc ccggcgtcaa cacgggataa taccgcgcca catagcagaa   1800
ctttaaaagt gctcatcatt ggaaaacgtt cttcggggcg aaaactctca aggatcttac   1860
cgctgttgag atccagttcg atgtaaccca ctcgtgcacc caactgatct tcagcatctt   1920
ttactttcac cagcgtttct gggtgagcaa aaacaggaag gcaaaatgcc gcaaaaaagg   1980
gaataagggc gacacggaaa tgttgaatac tcatactctt cctttttcaa tattatgtaa   2040
gcagacagtt ttattgttca tgatgatata ttttatctt gtgcaatgta acatcagaga   2100
ttttgagaca caacgtggct tgttgaata atcgaactt ttgctgagtt gaaggatcag   2160
atcacgcatc ttcccgacaa cgcagaccgt tccgtggcaa agcaaaagtt caaaatcacc   2220
aactggtcca cctacaacaa agctctcatc aaccgtggct ccctcacttt ctggctggat   2280
```

-continued

```
gatgggcga ttcaggcctg gtatgagtca gcaacacctt cttcacgagg cagacctcag    2340
cgccggtgat gccggccacg atgcgtccgg cgtagaggat ctctcaccta ccaaacaatg    2400 ccccctgca aaaataaat tcatataaaa aacatacaga taaccatctg cggtgataaa     2460
ttatctctgg cggtgttgac ataaatacca ctggcggtga tactgagcac atcagcagga   2520
cgcactgacc accatgaagg tgacgctctt aaaattaagc cctgaagaag ggcagcattc    2580
aaagcagaag gctttggggt gtgtgatacg aaacgaagca ttggaattcc ggatctcgat    2640
cccggaaatt aatacgactc actataggga gaccacaacg gtttccctct agaaataatt    2700
ttgtttaact ttaagaagga gatatacata tgcatcatca ccatcaccat cccggcggct    2760
cggacgaagt ggatgcgaaa tgggatcagt ggagcagcga ttggcagacc tggaacgcga    2820
aatgggatca gtggagcaac gattggaacg cgtggcgcag cgattggcag gcgtggaaag    2880
atgattgggc gcgctggaac cagcgctggg ataactgggc gaccggcggc aacaaactgt    2940
gcgaatataa cgtgtttcat aacaaaacct ttgaactgcc gcgcgcgcgc gtgaacacct    3000
agggatccct cgaggtcgac gaattcgagc tcggccgact tggccttccc tttagtgagg    3060
gttaataaac ttggtgagca ataactagca taaccccttg gggcctctaa acgggtcttg    3120
aggggttttt tgctgaaagg aggaactata tgcgctcata cgatatgaac gttgagactg    3180
ccgctgagtt atcagtgagc aataactagc ataacccctt ggggcctcta acgggtcttg    3240
gaggggtttt tt                                                        3252
```

<210> SEQ ID NO 50
<211> LENGTH: 28
<212> TYPE: PRT
<213> ORGANISM: respiratory syncytial virus

<400> SEQUENCE: 50

Cys Gly Gly Gly Ser Asn Lys Leu Ser Glu Tyr Asn Val Phe His Asn
1               5                   10                  15

Lys Thr Phe Glu Leu Pro Arg Ala Arg Val Asn Thr
            20                  25

<210> SEQ ID NO 51
<211> LENGTH: 29
<212> TYPE: PRT
<213> ORGANISM: respiratory syncytial virus

<400> SEQUENCE: 51

Cys Gly Gly Gly Ser Asn Lys Leu Ser Glu His Lys Thr Phe Ser Asn
1               5                   10                  15

Lys Thr Leu Glu Gln Gly Gln Met Tyr Gln Ile Asn Thr
            20                  25

<210> SEQ ID NO 52
<211> LENGTH: 90
<212> TYPE: PRT
<213> ORGANISM: Artificial Sequence
<220> FEATURE:
<223> OTHER INFORMATION: chimeric LPP(5)-SHe protein

<400> SEQUENCE: 52

Met His His His His His His Pro Gly Gly Ser Asp Glu Val Asp Ala
1               5                   10                  15

Lys Trp Asp Gln Trp Ser Ser Asp Trp Gln Thr Trp Asn Ala Lys Trp
            20                  25                  30

```
Asp Gln Trp Ser Asn Asp Trp Asn Ala Trp Arg Ser Asp Trp Gln Ala
            35                  40                  45
Trp Lys Asp Asp Trp Ala Arg Trp Asn Gln Arg Trp Asp Asn Trp Ala
        50                  55                  60
Thr Gly Gly Asn Lys Leu Cys Glu Tyr Asn Val Phe His Asn Lys Thr
65                  70                  75                  80
Phe Glu Leu Pro Arg Ala Arg Val Asn Thr
                85                  90

<210> SEQ ID NO 53
<211> LENGTH: 24
<212> TYPE: DNA
<213> ORGANISM: Artificial Sequence
<220> FEATURE:
<223> OTHER INFORMATION: Primer

<400> SEQUENCE: 53
gcgaaatggg atcagtggag cagc                                          24

<210> SEQ ID NO 54
<211> LENGTH: 36
<212> TYPE: DNA
<213> ORGANISM: Artificial Sequence
<220> FEATURE:
<223> OTHER INFORMATION: Primer

<400> SEQUENCE: 54
aatataggat ccctaggtcg cccagttatc ccagcg                             36

<210> SEQ ID NO 55
<211> LENGTH: 5
<212> TYPE: PRT
<213> ORGANISM: Artificial Sequence
<220> FEATURE:
<223> OTHER INFORMATION: synthetic peptide

<400> SEQUENCE: 55

Cys Gly Gly Gly Ser
1               5
```